US012103951B2

(12) United States Patent
Soares

(10) Patent No.: US 12,103,951 B2
(45) Date of Patent: Oct. 1, 2024

(54) USE OF CGRP RECEPTOR ANTAGONISTS IN NEUROPROTECTION AND NEUROLOGICAL DISORDERS

(71) Applicant: Christopher Joseph Soares, La Jolla, CA (US)

(72) Inventor: Christopher Joseph Soares, La Jolla, CA (US)

( * ) Notice: Subject to any disclaimer, the term of this patent is extended or adjusted under 35 U.S.C. 154(b) by 0 days.

(21) Appl. No.: 17/806,834

(22) Filed: Jun. 14, 2022

(65) Prior Publication Data

US 2023/0212248 A1 Jul. 6, 2023

Related U.S. Application Data

(63) Continuation of application No. 16/329,596, filed as application No. PCT/US2017/049460 on Aug. 30, 2017, now Pat. No. 11,390,654.

(60) Provisional application No. 62/383,334, filed on Sep. 2, 2016.

(51) Int. Cl.
| | |
|---|---|
| *C07K 14/435* | (2006.01) |
| *A61K 38/00* | (2006.01) |
| *A61P 3/06* | (2006.01) |
| *C07K 14/57* | (2006.01) |
| *C07K 14/575* | (2006.01) |

(52) U.S. Cl.
CPC .............. *C07K 14/435* (2013.01); *A61P 3/06* (2018.01); *C07K 14/57527* (2013.01); *A61K 38/00* (2013.01)

(58) Field of Classification Search
CPC ... C07K 14/435; C07K 14/57527; A61P 3/06; A61K 38/00
See application file for complete search history.

(56) References Cited

U.S. PATENT DOCUMENTS

| | | | |
|---|---|---|---|
| 3,940,475 A | 2/1976 | Gross | |
| 4,179,337 A | 12/1979 | Davis | |
| 4,301,144 A | 11/1981 | Iwashita | |
| 4,496,689 A | 1/1985 | Mitra | |
| 4,522,752 A | 6/1985 | Sisto | |
| 4,530,838 A | 7/1985 | Evans | |
| 4,640,835 A | 2/1987 | Shimizu | |
| 4,670,417 A | 6/1987 | Iwasaki | |
| 4,743,677 A | 5/1988 | Noda et al. | |
| 4,791,192 A | 12/1988 | Nakagawa | |
| 5,364,934 A | 11/1994 | Drayna | |
| 5,698,401 A | 12/1997 | Fesik | |
| 5,733,569 A | 3/1998 | Azria | |
| 5,804,390 A | 9/1998 | Fesik | |
| 7,812,120 B2 | 10/2010 | Quay | |
| 8,114,958 B2 | 2/2012 | Soares et al. | |
| 8,263,545 B2 | 9/2012 | Levy et al. | |
| 9,193,776 B2 | 11/2015 | Soares | |
| 10,370,425 B2 | 8/2019 | Soares | |
| 11,390,654 B2 | 7/2022 | Soares | |
| 2004/0072809 A1 | 4/2004 | Demopulos et al. | |
| 2006/0094652 A1* | 5/2006 | Levy | A61P 3/06 514/12.6 |
| 2008/0274952 A1 | 11/2008 | Soares et al. | |
| 2008/0312157 A1 | 12/2008 | Levy et al. | |
| 2009/0264368 A1 | 10/2009 | Goldberg | |
| 2010/0016229 A1 | 1/2010 | Sarubbi | |
| 2010/0311705 A1 | 12/2010 | Demopulos et al. | |
| 2014/0235597 A1 | 8/2014 | Demopulos et al. | |
| 2014/0329752 A1* | 11/2014 | Soares | C07K 14/585 514/11.9 |
| 2016/0145315 A1 | 5/2016 | Soares | |
| 2016/0176961 A1 | 6/2016 | Baker | |
| 2017/0204155 A1 | 7/2017 | Soares | |
| 2020/0165305 A1 | 5/2020 | Soares | |

FOREIGN PATENT DOCUMENTS

| | | |
|---|---|---|
| EA | 015526 B1 | 8/2011 |
| EP | 0045665 A1 | 2/1982 |
| EP | 0253464 B1 | 5/1992 |
| EP | 0613683 A1 | 9/1994 |
| EP | 2127676 A2 | 12/2009 |
| JP | S62-129297 | 6/1987 |
| RU | 2385878 C2 | 3/2010 |
| WO | WO 1993/25221 | 12/1993 |
| WO | WO 1994/17784 | 8/1994 |
| WO | WO 1994/21665 | 9/1994 |
| WO | WO 1995/34326 | 12/1995 |
| WO | WO 1997/41223 | 11/1997 |
| WO | WO 2006/083254 | 8/2006 |
| WO | WO 2006/086769 | 8/2006 |
| WO | WO 2006/105345 | 10/2006 |

(Continued)

OTHER PUBLICATIONS

IUBMB—International Union of Biochemistry and Molecular Biology, 1993, Biochemical nomenclature, and enzyme nomenclature, Eur. J. Biochem. 213:1-3.

IUPAC and IUB, 1984, Nomenclature and symbolism for amino acids and peptides, Pure Appl. Chem., 56(5):595-624.

IUPAC-IUB Joint Commission on Biochemical Nomenclature (JCBN), 1984, Nomenclature and symbolism for amino acids and peptides. Recommendations 1983. Eur. J. Biochem, 138:9-37.

Kuwasako et al., 2012. Unique molecular mechanism and circulatory regulation of the type 1 adrenomedulin receptor complex. J Japanese Pharmacol. 140(1): 8-13.

Alajuuma et al., 2002, Effect of simultaneous CGRP and PGF(2alpha) on the outflow facility in the rabbit eye, Ophthalmic Res. 34(5): 309-313.

(Continued)

*Primary Examiner* — Amber D Steele
(74) *Attorney, Agent, or Firm* — Knobbe, Martens, Olson & Bear, LLP

(57) ABSTRACT

Provided herein are treatment methods, including methods of treating nerve damage, methods of neuroprotection, methods of treating glaucoma and methods of lowering LDL levels. The methods generally involve administering to an individual in need thereof an effective amount of a CGRP receptor antagonist peptide or composition.

10 Claims, 5 Drawing Sheets

Specification includes a Sequence Listing.

(56) References Cited

FOREIGN PATENT DOCUMENTS

| WO | WO 2006/105527 | 10/2006 |
|----|----|----|
| WO | WO 2007/054809 | 5/2007 |
| WO | WO 2007/055728 | 5/2007 |
| WO | WO 2007/055743 | 5/2007 |
| WO | WO 2009/064298 | 5/2009 |
| WO | WO 2010/107874 | 9/2010 |
| WO | WO 2013/059336 | 4/2013 |
| WO | WO 2013/112912 | 8/2013 |
| WO | WO 2013/130402 | 9/2013 |
| WO | WO 2015/176017 | 11/2015 |

OTHER PUBLICATIONS

Alajuuma P., 2004, Calcitonin gene-related peptide: Characterization of binding sites and structure-activity relationships in the eye and effects on intraocular pressure, Academic Dissertation University of Tampere, 59 pages.
Alm et al., 1989, Effects of topically applied PGF2α and its isopropylester on normal and glaucomatous human eyes, Prog. Clin. Biol. Res., 312:447-58.
Almquist et al., 1980) "Synthesis and biological activity of a ketomethylene analogue of a tripeptide inhibitor of angiotensin converting enzyme" J. Med. Chem. 23:1392-1398.
Altschul et al. (1996) "Local alignment statistics" Methods in Enzymology, 266:460-480.
Altschul et al., 1997, Gapped BLAST and PSI-BLAST: a new generation of protein database search programs. Nucleic Acids Res., 25(17):3389-3402.
Andreu et al., 1994, Formation of disulfide bonds in synthetic peptides and proteins, Chapter 7; Peptide Synthesis Protocols; Meth. Mol. Bio. 35(7):91-169.
Ashina et al., 2000, Evidence for increased plasma levels of calcitonin gene-related peptide in migraine outside of attacks, Pain 86(1-2):133-138.
Ball et al., 1990, Conformational constraints: nonpeptide β-turn mimics, J Mol Recogn. 3(2):55-64.
Banerjee et al., 2006, Identification of specific calcitonin-like receptor residues important for calcitonin gene-related peptide high affinity binding, BMC Pharmacology, 6(1):9 in 12 pages.
Bannwarth et al., 1996, Global phosphorylation of peptides containing oxidation-sensitive amino acids, Biorg Med Chem Letts. 6(17):2141-2146.
Barker et al. (1992) "Cyclic RGD peptide analogues as antiplatelet antithrombotics" J. Med. Chem. 35:2040-2048.
Bodanszky M., 1993, Principles of Peptide Synthesis, Springer-Verlag; Preface & Table of Contents in 10 pages.
Borsotto et al., 1985, The 1,4-dihydropyridine receptor associated with the skeletal muscle voltage-dependent Ca2+ channel. Purification and subunit composition. J Biol Chem 260(26):14255-14263.
Bundgaard [Ed], 1985, Design of Prodrugs, Elsevier Science Publishers, Amsterdam; Table of Contents.
Castel et al., 2016, Peripheral Neuritis Trauma in Pigs: A Neuropathic Pain Model. J Pain. 17(1):36-49.
Chader et al., 2012, Key Needs and Opportunities for Treating Glaucoma. Invest Ophthalmol Vis Sci. 54(5):2456-2460.
Christopoulos et al., 1999, Multiple amylin receptors arise from receptor activity-modifying protein interaction with the calcitonin receptor gene product. Mol Pharmacol. 56:235-242.
Cone et al., 2012, The Effects of Anesthesia, Mouse Strain, and Age on Intraocular Pressure and an Improved Murine Model of Experimental Glaucoma. Exp Eye Res. 99(1):27-35.
Cumberbatch et al., 1999, Dural vasodilation causes a sensitization of rat caudal trigeminal neurons in vivo that is blocked by a 5-HT1B/1D agonist. Br J Pharmacol. 126(6):1478-1486.
Danaher et al, 2008, Evidence that α-calcitonin gene-related peptide is a neurohormone that controls systemic lipid availability and utilization, Endocrinology 149(1):154-160.

Davies [Ed], (1985) Amino Acids and Peptides, Chapman and Hall, London, pp. 387-410.
De Prado et al., 2007, CGRP receptor antagonists: A new frontier of anti-migraine medications, Drug Discovery Today. 3(4):593-597.
Dhillo et al., 2002, CGRP-alpha inhibits food intake via the paraventricular nucleus (PVN) of the hypothalamus partly through the CGRP-type 1 receptor, Endocrine Abstracts 30C43; ISSN1470-3947, 2 pp.
Durham et al., 2010, CGRP receptor antagonists in the treatment of migraine, CNS Drugs 24(7):539-548.
Edvinsson L., 2001, Calcitonin gene-related peptide (CGRP) and the pathophysiology of headache: therapeutic implications, CNS Drugs 15(10):745-753.
Emerick G.T., 2008, Migraines in the Presence of Glaucoma, Glaucoma Today, Sep./Oct. 2008; pp. 21-23.
Evans et al., 1987, Design of nonpeptical ligands for a peptide receptor: cholecystokinin antagonists, J. Med. Chem. 30:1229-1239, and Supporting Information, 5 pp.
Farmer, P.S., 1980, Drug Design, Ariens E.J. [Ed], Academic Press, New York, vol. 10:119-143.
Fauchère J.-L., 1986, Elements for the rational design of peptide drugs, in Advances in Drug Research, Testa B. [Ed]. vol. 15, pp. 29-69.
Fingl et al., 1975, Section I—Introduction, Chapter 1—General Principles, in The Pharmacological Basis of Therapeutics, Goodman et al., [Eds.], 5th Edition; pp. 1-46.
Fischer et al., 2005, The Nonpeptide Calcitonin Gene-related Peptide Receptor Antagonist BIBN4096BS Lowers the Activity of Neurons with Meningeal Input in the Rat Spinal Trigeminal Nucleus. J Neurosc. 25(25):5877-5883.
Freidinger R.M., 1989, Non-peptide ligands for peptide receptors, Trends Pharmacol. Sci. 10:270-274.
Gallai et al., 1995, Vasoactive peptide levels in the plasma of young migraine patients with and without aura assessed both interictally and ictally, Cephalalgia 15:384-90.
Gante J., 1994, Peptidomimetics—Tailored Enzyme Inhibitors, Angew. Chem. Int. Ed. Engl. 33:1699-1720.
GenBank Database, "Calcitonin Gene Related Protein", Accession No. AAA52011.1, filed on Nov. 1, 1994 in 1 page.
Geneseq Database [Online] Feb. 7, 2003 (Feb. 3, 2003), "Human calcitonin gene-related peptide 1." XP002694858, retrieved from EBI accession No. GSP:ABP55105, Database accession No. ABP55105 in 1 page.
Geneseq Database, "Amylin agonist peptide, SEQ:106.", XP002732366, retrieved from EBI accession No. GSP:AYJ13644 Database accession No. AYJ13644 sequence ID No. 106., Nov. 11, 2010 in 1 page.
Geneseq Database, "Amylin agonist peptide, SEQ:114.", XP002732365, retrieved from EBI accession No. GSP:AYJ13652 Database accession No. AYJ13652 sequence No. 114., Nov. 11, 2010 in 1 page.
Goadsby et al., 1990, Vasoactive peptide release in the extracerebral circulation of humans during migraine headache. Ann Neurol. 28:183-187.
Goodman et al., 1981, The Synthesis and Conformational Analysis of Retro-Inverso Analogues of Biologically Active Molecules, in Perspectives in Peptide Chemistry, Eberle et al., [Eds.]; Karger, Basel, CH; pp. 283-294.
Grant et al., 2002, Evidence of a role for NK1 and CGRP receptors in mediating neurogenic vasodilatation in the mouse ear, Brit J Pharmacol. 135:356-362.
Gupta et al., 2007, Glaucoma as a neurodegenerative disease. Curr Opin Ophthalmol. 18(2):110-114.
Hann, 1982, On the double bond isostere of the peptide bond: preparation of an enkephalin analogue, J. Chem. Soc. Perkin. Trans. I 307-314.
Hay et al., 2001, Knockouts and transgenics confirm the importance of adrenomedullin in the vasculature, Trends Pharmacol. Sci. 22(2):57-59.
Heino et al., 1998, Binding of CGRP Analogs and their Effect on Adenylate Cyclase Activity in Porcine Iris-Ciliary Body, J Ocul Pharmacol Thera., 14(6):543-554.
Holladay et al., 1983, Synthesis of Hydroxyethylene and Ketomethylene Dipeptide Isoteres, Tetrahedron Lett. 24:4401-4404.

(56) References Cited

OTHER PUBLICATIONS

Howitt et al., 1997, The selectivity and structural determinants of peptide antagonists at the CGRP receptor of rat, L6 myocytes, Brit J Pharmacol. 121(5):1000-10004.
Hruby, 1982, Conformational restrictions of biologically active peptides via amino acid side chain groups, Life Sci. 31(3):189-199.
Hruby et al., 1990, Emerging approaches in the molecular design of receptor-selective peptide ligands: conformational, topographical and dynamic considerations, Biochem J. 268(2):249-262.
Hudson et al., 1979, Methionine enkephalin and isosteric analogues. Int J Pept Prot Res. 14:177-185.
IUBMB—International Union of Biochemistry and Molecular Biology, 1993, Biochemical nomenclature, and enzyme nomenclature, Eur. J. Biochem. 213:1-33.
IUPAC-IUB Joint Commission on Biochemical Nomenclature (JCBN), 1984, Nomenclature and symbolism for amino acids and peptides. Recommendations 1983. Biochem. J., 219:345-373.
James et al., 1993, Benzodiazepine peptidomimetics: potent inhibitors of Ras farnesylation in animal cells. Science 260:1937-1942.
Jennings-White et al., 1982, Synthesis of Ketomethylene Analogs of Dipeptides. Tetrahedron Lett. 23:2533-2534.
Joshi A., 1994, Microparticulates for ophthalmic drug delivery. J. Ocul. Pharmacol., 10(1):29-45.
Kahns et al., 1991, Prodrugs of peptides. 13. Stabilization of peptide amides against α-chymotrypsin by the prodrug approach, Pharmaceut Res. 8(12):1533-1538.
Kalesnykas et al., 2007, The expression of heat shock protein 27 in retinal ganglion and glial cells in a rat glaucoma model. Neuroscience 150(3):692-704.
Kalesnykas et al., 2008, Neurodegeneration and cellular stress in the retina and optic nerve in rat cerebral ischemia and hypoperfusion models. Neuroscience. 155(3):937-947.
Kalesnykas et al., 2012, Retinal Ganglion Cell Morphology after Optic Nerve Crush and Experimental Glaucoma. Invest Ophthalmol Vis Sci. 53(7):3847-3857.
Krootilla et al., 1991, Intraocular and Cardiovascular Effects of Calcitonin Gene-Related Peptide (CGRP)-I and II in the Rabbit. Invest Ophthalmol Visual Science. 32(12): 3084-3090.
Lassen et al., 2002, CGRP may play a causative role in migraine. Cephalalgia 22(1):54-61.
Lehninger, Principles of Biochemistry, 2005, 4th Ed, Nelson et al. [Eds.] Freeman and Company, Chapter 4, pp. 120-122.
Luthman et al., 1996, A Textbook of Drug Design and Development, 2nd Ed., Krogsgaard-Larsen et al. [Eds.], Harwood Academic Publishers; 14:386-406.
Ma H., 2004, Calcitonin gene-related peptide (CGRP), Nature and Science 2(3):41-47.
March J. [Ed.], 1992, Advanced Organic Chemistry—Reactions, Mechanisms, and Structure, 4th Ed., John Wiley & Sons, pp. 393-396.
Martinez-Alvarez et al., 2009, Effect of calcitonin gene-related peptide (CGRP), adrenomedullin and adrenomedullin-2/intermedin on food intake in goldfish (*Carassius auratus*), Peptides 30(4):803-807.
Mayer et al., 1996, Efficacy of a Novel Hydrogel Formulation in Human Volunteers. Ophthalmologica 210(2):101-103.
McLatchie et al., 1998, RAMPs regulate the transport and ligand specificity of the calcitonin-receptor-like receptor, Nature 393:333-339.
Merck Updates Status of Clinical Development Programs for Investigational CGRP Receptor Antagonist Treatments for Acute Migraine; MK-3207 Clinical Development Discontinued., Sep. 10, 2009. Merck & Co., Inc. Web. Jun. 1, 2011 in 27 pages.
Merrifield R.B., 1963, Solid phase peptide synthesis. I. The synthesis of a tetrapeptide, J Am Chem Soc. 85:2149-2154.
Mimeault et al., 1992, Structure-activity study of hCGRP8-37, a calcitonin gene-related peptide receptor antagonist. J Med Chem. 35:2163-2168.
Miranda et al., 2008, Identification of potent, selective, and metabolically stable peptide antagonists to the calcitonin gene-related peptide (CGRP) receptor, J Med Chem. 51(24):7889-7897, and Supporting Information, pp. S1-S5.
Miret et al., 2002, Functional expression of heteromeric calcitonin gene-related peptide and adrenomedullin receptors in yeast, JBC 277(9):6881-6887.
Monfardini et al., 1995, A branched monomethoxypoly(ethylene glycol) for protein modification. Biocon Chem. 6:62-69.
Mordenti, 1999, Intraocular Pharmacokinetics and Safety of a Humanized Monoclonal Antibody in Rabbits after Intravitreal Administration of a Solution or a PLGA Microsphere Formulation, Toxicol Sci., 52(1):101-6.
Morgan et al., 1989, Approaches to the discovery of non-peptide ligands for peptide receptors and peptidases, Chapter 26.; Ann Rep Med Chem. 24:243-252.
Morley, 1980, K+ channel openers and suppression of airway hyperreactivity. Trends Pharm Sci. pp. 463-468, (general review).
Morley et al., 1995, Peripherally Administered Calcitonin Gene-related Peptide Decreases Food Intake in Mice, Peptides 17(3):511-516.
Moskowitz, 1992, Neurogenic versus vascular mechanisms of sumatriptan and ergot alkaloids in migraine. Trends Pharmacol Sci. 13:307-311.
Mufson et al., 1999, Distribution and retrograde transport of trophic factors in the central nervous system: functional implications for the treatment of neurodegenerative diseases. Prog Neurobiol. 57(4):451-484.
Mufson et al., 2006, Neuronal gene expression profiling: uncovering the molecular biology of neurodegenerative disease. Prog Brain Res. 158:197-222.
Mulder et al., 2000, Islet amyloid polypeptide (amylin)-deficient mice develop a more severe form of alloxan-induced diabetes, Am J Physiol. 278(4):E684-E691.
Nafissi et al., 2015, Neuroprotective therapies in glaucoma: II. Genetic nanotechnology tools. Front Neurosci. 9:355.
Or et al., 1991, Cysteine alkylation in unprotected peptides: Synthesis of a carbavasopressin analogue by intramolecular cysteine alkylation, J Org Chem. 56:3146-3149.
Pellecchia et al., 2002, NMR in drug discovery. Nature Rev Drug Disc. 1:211-219.
Polska et al., (2002) Effects of Adenosine on Intraocular Pressure, Optic Nerve Head Blood Flow, and Choroidal Blood Flow in Healthy Humans. Invest Ophthalm Visual Science 44(7): 3110-3114.
Poyner D., 1992, Calcitonin gene-related peptide: multiple actions, multiple receptors. Pharmac Ther. 56:23-51.
Poyner et al., 2002, International Union of Pharmacology. XXXII. The Mammalian Calcitonin Gene-Related Peptides, Adrenomedullin, Amylin, and Calcitonin Receptors Pharmacol Rev. 54(2):233-246.
Poyner et al., 2009, CGRP Receptor Antagonists: Design and Screening, Exp Opin Drug Disc. 4(12):1253-1265.
Ragauskas et al., 2014, Early Retinal Function Deficit without Prominent Morphological Changes in the R6/2 Mouse Model of Huntington's Disease. PLoS One. 9(12):e113317.
Rizo et al., 1992, Constrained peptides: models of bioactive peptides and protein substructures. Ann Rev Biochem. 61:387-418.
Roberts et al., 1983, Unusual Amino-Acids in Peptide Synthesis, in The Peptides: analysis, Synthesis, Biology, Gross et al. [Eds], Academic Press, New York, Chapter 6; 5:341-449.
Roh et al., 2004, Intermedin Is a Calcitonin/Calcitonin Gene-related Peptide Family Peptide Acting through the Calcitonin Receptor-like Receptor/Receptor Activity-modifying Protein Receptor Complexes, JBC 279(8):7264-7274.
Rovero et al., 1992, CGRP antagonist activity of short C-terminal fragments of human alpha CGRP, CGRP(23-37) and CGRP(19-37). Peptides 13:1025-1027.
Russo A.F., 2015, Calcitonin gene-related peptide (CGRP): a new target for migraine. Annu Rev Pharmacol Toxicol. 55:533-552.
Russo et al., 2016, Retinal ganglion cell death in glaucoma: Exploring the role of neuroinflammation. Eur J Pharmacol. 787:134-142.
Salmon et al., 1999, Modulation of morphine analgesia in alphaCGRP mutant mice. Neuroreport 10(4):849-854.

(56) References Cited

OTHER PUBLICATIONS

Salmon et al., 2001, Altered neuroadaptation in opiate dependence and neurogenic inflammatory nociception in alpha CGRP-deficient mice. Nat Neurosci. 4: 357-358.

Serra et al., 1999, Activity-dependent slowing of conduction differentiates functional subtypes of C fibres innervating human skin. J Physiol. 515(Pt3):799-811.

Serra et al., 2012, Microneurographic identification of spontaneous activity in C-nociceptors in neuropathic pain states in humans and rats. Pain. 153(1):42-55.

Schellenberger et al., 2009, A recombinant polypeptide extends the in vivo half-life of peptides and proteins in a tunable manner, Nature Biotech. 27(12):1186-1192.

Shedden et al., 2001, Efficacy and tolerability of timolol maleate ophthalmic gel-forming solution versus timolol ophthalmic solution in adults with open-angle glaucoma or ocular hypertension: a six-month, double-masked, multicenter study. Clin Ther., 23(3):440-50.

Shindo et al., 2001, Vascular Abnormalities and Elevated Blood Pressure in Mice Lacking Adrenomedullin Gene. Circulation 104:1964-1971.

Smith et al., 2003, Modifications to the n-terminus but not the c-terminus of calcitonin gene-related peptide(8-37) produce antagonists with increased affinity, J Med Chem, 46(12):2427-2435, and Supporting Information pp. 1-7.

Song et al., 2016, Pharmacological Modulation of Functional Phenotypes of Microglia in Neurodegenerative Diseases. Front Aging Neurosci. 9:139.

Song et al., 2016, Degeneration of Dopaminergic Neurons Due to Metabolic Alterations and Parkinson's Disease. Front Aging Neurosci. 8:65.

Spatola, 1983, Peptide Backbone Modifications: a structure-activity analysis of peptides containing amide bond surrogates, conformational constraints and rela . . . , in Chemistry and Biochemistry of Amino Acids, Peptides and Proteins, Weinstein ed., Marcel Dekker, Inc., New York. Chapter 5, pp. 267-357.

Spatola et al., 1986, Structure-activity relationships of enkephalins containing serially replaced thiomethylene amide bond surrogates, Life Sci. 38:1243-1249.

Tainer et al., 1984, The reactivity of anti-peptide antibodies is a function of the atomic mobility of sites in a protein, Nature 312(5990):127-134.

Taylor et al., 2006, Pharmacological characterization of novel alpha-Calcitonin Gene-Related Peptide (CGRP) receptor peptide antagonists that are selective for human CGRP receptors, J Pharmacol Exp Ther. 319(2):749-757.

Tepper et al., 2008, Clinical and Preclinical Rationale for CGRP-Receptor Antagonists in the Treatment of Migraine, Headache 48(8):1259-1268.

Tice et al., 1992, Parenteral Drug Delivery: Injectables, in Treatise on Controlled Drug Delivery, Kydonieus A. [Ed], Marcel Dekker, N.Y. 1992, Chapter 7, pp. 315-339.

Tilikaratne et al., 2000, Amylin Receptor Phenotypes Derived from Human Calcitonin Receptor/RAMP expression Exhibit Pharmacological Differences Dependent on Receptor Isoform and Host Cell Environment, J Pharmacol Exp Ther. 294(1):61-72.

Veber et al., 1985, The design of metabolically-stable peptide analogs, TINS, pp. 392-396.

Watkins et al., 2013, Structure-activity relationships for α-calcitonin gene-related peptide, Br J Pharmacol. 170:1308-1322.

Weaner et al., 1995, Tritium labeling of n-protected amino acids and peptides containing O-alkyl-tyrosyl residues, in Synthesis and Applications of Isotopically Labelled Compounds 1994, Allen et al., [Eds], pp. 137-140.

Williamson et al., 2001, Neurogenic inflammation in the context of migraine, Microsc Res Tech. 53:167-178.

Wolff M.E. [Ed], 1995, Burger's Medicinal Chemistry and Drug Discovery, 5th Ed., vol. I: Principles and Practice, John Wiley and Sons, Inc.; Table of Contents in 5 pages.

Zalipsky, 1995, Functionalized poly(ethylene glycol) for preparation of biologically relevant conjugates, Bioconj Chem. 6:150-165.

Zhang et al., 2001, Arthritic calcitonin/a calcitonin gene-related peptide knockout mice have reduced nociceptive hypersensitivity, Pain. 89:265-273.

Zhang et al., 2007, Sensitization of Calcitonin Gene-related Peptide Receptors by Receptor Activity-modifying Protein-1 in the Trigeminal Ganglion. J Neurosci. 27(10):2693-2703.

International Search Report and Written Opinion dated Feb. 8, 2018 for Application No. PCT/US2017/049460.

Oksala et al., Effects of Calcitonin Gene-Related Peptide in the Eye. Invest Ophthalmol Visual Science. Jul. 1988;29(7): 1006-1011.

\* cited by examiner

SEQUENCE LISTING

```
<160> NUMBER OF SEQ ID NOS: 58

<210> SEQ ID NO 1
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: C-terminal amine group

<400> SEQUENCE: 1

Ala Cys Asp Thr Ala Ala Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: C-terminal amine group

<400> SEQUENCE: 2

Ala Cys Asp Thr Ala Ser Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 3
<211> LENGTH: 32
<212> TYPE: PRT
<213> ORGANISM: Artificial Sequence
<220> FEATURE:
```

<223> OTHER INFORMATION: Synthetic peptide
<220> FEATURE:
<221> NAME/KEY: misc_feature
<222> LOCATION: (32)..(32)
<223> OTHER INFORMATION: C-terminal amine group

<400> SEQUENCE: 3

Ala Cys Asp Thr Ala Val Cys Val Leu Gly Arg Leu Ser Gln Glu Leu
1               5                   10                  15
His Arg Leu Gln Thr Tyr Pro Arg Thr Asn Val Gly Ser Lys Ala Phe
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: C-terminal amine group

<400> SEQUENCE: 4

Ala Cys Asn Thr Ala Ala Cys Val Leu Gly Arg Leu Ser Gln Glu Leu
1               5                   10                  15
His Arg Leu Gln Thr Tyr Pro Arg Thr Asn Val Gly Ser Lys Ala Phe
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: C-terminal amine group

<400> SEQUENCE: 5

Ala Cys Val Leu Gly Ala Cys Val Leu Gly Arg Leu Ser Gln Glu Leu
1               5                   10                  15
His Arg Leu Gln Thr Tyr Pro Arg Thr Asn Val Gly Ser Lys Ala Phe
            20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: C-terminal amine group

<400> SEQUENCE: 6

Ala Cys Arg Phe Gly Ala Cys Val Leu Gly Arg Leu Ser Gln Glu Leu
1               5                   10                  15
His Arg Leu Gln Thr Tyr Pro Arg Thr Asn Val Gly Ser Lys Ala Phe
            20                  25                  30

<210> SEQ ID NO 7
<211> LENGTH: 32
<212> TYPE: PRT
<213> ORGANISM: Artificial Sequence

```
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: C-terminal amine group

<400> SEQUENCE: 7

Ala Cys Asn Leu Ser Ala Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: C-terminal amine group

<400> SEQUENCE: 8

Cys Ser Asn Thr Ala Ala Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 9
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: C-terminal amine group

<400> SEQUENCE: 9

Ala Cys Asp Thr Ala Leu Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: C-terminal amine group

<400> SEQUENCE: 10

Ala Cys Asp Thr Ala Ile Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 11
<211> LENGTH: 32
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: C-terminal amine group

<400> SEQUENCE: 11

Ala Cys Asn Leu Ser Val Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: C-terminal amine group

<400> SEQUENCE: 12

Cys Ser Asn Thr Ala Val Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (31)..(31)
<223> OTHER INFORMATION: C-terminal amine group

<400> SEQUENCE: 13

Ala Cys Asn Leu Ser Ala Cys Val Leu Gly Arg Leu Ser Gln Glu Leu
1               5                   10                  15

His Arg Leu Gln Thr Tyr Pro Thr Asn Thr Gly Ser Gly Thr Pro
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: C-terminal amine group

<400> SEQUENCE: 14

Ala Cys Val Leu Gly Ala Cys Val Leu Gly Arg Leu Ser Gln Glu Leu
1               5                   10                  15

His Arg Leu Gln Thr Tyr Pro Val Asp Pro Ser Ser Pro His Ser Tyr
            20                  25                  30

<210> SEQ ID NO 15
<211> LENGTH: 37
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (37)..(37)
<223> OTHER INFORMATION: C-terminal amine group

<400> SEQUENCE: 15

Ala Cys Asp Thr Ala Ala Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(1)
<223> OTHER INFORMATION: Xaa = selected from the group consisting Ala,
      Cys, Gly, Ile, Leu, Met, Phe, Pro, Trp, and Val
<220> FEATURE:
<221> NAME/KEY: VARIANT
<222> LOCATION: (2)...(2)
<223> OTHER INFORMATION: Xaa = selected from the group consisting of
      Cys, Ser, and Tyr
<220> FEATURE:
<221> NAME/KEY: VARIANT
<222> LOCATION: (3)...(3)
<223> OTHER INFORMATION: Xaa = selected from the group consisting of
      Arg, Asn, Asp, Cys, Glu, Gln, His, Lys, Ser, Thr, Tyr,
      and Val
<220> FEATURE:
<221> NAME/KEY: VARIANT
<222> LOCATION: (4)...(4)
<223> OTHER INFORMATION: Xaa = selected from the group consisting of
      Arg, Asn, Asp, Glu, Gln, His, Leu, Lys, Phe, Ser, Thr,
      Tyr, and Val
<220> FEATURE:
<221> NAME/KEY: VARIANT
<222> LOCATION: (5)...(5)
<223> OTHER INFORMATION: Xaa = selected from the group consisting of
      Ala, Gly, Ile, Leu, Met, Phe, Ser, Typ, and Val
<220> FEATURE:
<221> NAME/KEY: VARIANT
<222> LOCATION: (6)...(6)
<223> OTHER INFORMATION: Xaa = selected from the group consisting of
      Ala, Gly, Ile, Leu, Met, Phe, Ser, Typ, and Val
<220> FEATURE:
<221> NAME/KEY: VARIANT
<222> LOCATION: (7)...(7)
<223> OTHER INFORMATION: Xaa = Cys

<400> SEQUENCE: 16

Xaa Xaa Xaa Xaa Xaa Xaa Xaa
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17
```

```
Ala Cys Asp Thr Ala Ala Cys
1               5
```

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

```
Ala Cys Asp Thr Ala Ser Cys
1               5
```

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

```
Ala Cys Asp Thr Ala Val Cys
1               5
```

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

```
Ala Cys Asn Thr Ala Ala Cys
1               5
```

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide

<400> SEQUENCE: 21

```
Ala Cys Val Leu Gly Ala Cys
1               5
```

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide

<400> SEQUENCE: 22

```
Ala Cys Arg Phe Gly Ala Cys
1               5
```

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

```
Ala Cys Asp Leu Ser Ala Cys
```

```
1               5
```

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

```
Ala Cys Asn Leu Ser Ala Cys
1               5
```

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide

<400> SEQUENCE: 25

```
Cys Ser Asn Thr Ala Ala Cys
1               5
```

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide

<400> SEQUENCE: 26

```
Ala Cys Asp Thr Ala Leu Cys
1               5
```

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide

<400> SEQUENCE: 27

```
Ala Cys Asp Thr Ala Ile Cys
1               5
```

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide

<400> SEQUENCE: 28

```
Ala Cys Asp Thr Ala Leu Cys
1               5
```

<210> SEQ ID NO 29
<211> LENGTH: 7
<212> TYPE: PRT
<213> ORGANISM: Artificial Sequence
<220> FEATURE:
<223> OTHER INFORMATION: Synthetic peptide

<400> SEQUENCE: 29

```
Ala Cys Asp Thr Ala Ile Cys
1               5
```

```
<210> SEQ ID NO 30
<211> LENGTH: 7
<212> TYPE: PRT
<213> ORGANISM: Artificial Sequence
<220> FEATURE:
<223> OTHER INFORMATION: Synthetic peptide

<400> SEQUENCE: 30

Ala Cys Asp Leu Ser Val Cys
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide

<400> SEQUENCE: 31

Ala Cys Asp Leu Ser Val Cys
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide

<400> SEQUENCE: 32

Ala Cys Asn Leu Ser Val Cys
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide

<400> SEQUENCE: 33

Cys Ser Asn Thr Ala Val Cys
1               5

<210> SEQ ID NO 34
<211> LENGTH: 19
<212> TYPE: PRT
<213> ORGANISM: Artificial Sequence
<220> FEATURE:
<223> OTHER INFORMATION: Synthetic peptide

<400> SEQUENCE: 34

Val Leu Gly Arg Leu Ser Gln Glu Leu His Arg Leu Gln Thr Tyr Pro
1               5                   10                  15

Arg Thr Asn

<210> SEQ ID NO 35
<211> LENGTH: 19
<212> TYPE: PRT
<213> ORGANISM: Artificial Sequence
<220> FEATURE:
<223> OTHER INFORMATION: Synthetic peptide

<400> SEQUENCE: 35

Val Leu Gly Lys Leu Ser Gln Glu Leu His Lys Leu Gln Thr Tyr Pro
```

```
1               5                   10                  15

Arg Thr Asn

<210> SEQ ID NO 36
<211> LENGTH: 19
<212> TYPE: PRT
<213> ORGANISM: Artificial Sequence
<220> FEATURE:
<223> OTHER INFORMATION: Synthetic peptide

<400> SEQUENCE: 36

Val Leu Gly Lys Leu Ser Gln Glu Leu His Lys Leu Gln Thr Tyr Pro
1               5                   10                  15

Arg Thr Asp

<210> SEQ ID NO 37
<211> LENGTH: 19
<212> TYPE: PRT
<213> ORGANISM: Artificial Sequence
<220> FEATURE:
<223> OTHER INFORMATION: Synthetic peptide

<400> SEQUENCE: 37

Val Leu Gly Lys Leu Ser Gln Glu Leu His Lys Leu Gln Thr Phe Pro
1               5                   10                  15

Arg Thr Asn

<210> SEQ ID NO 38
<211> LENGTH: 19
<212> TYPE: PRT
<213> ORGANISM: Artificial Sequence
<220> FEATURE:
<223> OTHER INFORMATION: Synthetic peptide

<400> SEQUENCE: 38

Val Leu Gly Lys Leu Ser Gln Asp Ile His Lys Leu Gln Thr Tyr Pro
1               5                   10                  15

Arg Thr Asn

<210> SEQ ID NO 39
<211> LENGTH: 19
<212> TYPE: PRT
<213> ORGANISM: Artificial Sequence
<220> FEATURE:
<223> OTHER INFORMATION: Synthetic peptide

<400> SEQUENCE: 39

Val Leu Gly Lys Leu Ser Gln Glu Leu His Lys Met Gln Thr Tyr Pro
1               5                   10                  15

Arg Thr Asp

<210> SEQ ID NO 40
<211> LENGTH: 19
<212> TYPE: PRT
<213> ORGANISM: Artificial Sequence
<220> FEATURE:
<223> OTHER INFORMATION: Synthetic peptide

<400> SEQUENCE: 40

Leu Leu Gly Lys Leu Ser Gln Glu Leu His Arg Leu Gln Thr Tyr Thr
1               5                   10                  15

Arg Thr Asp
```

```
<210> SEQ ID NO 41
<211> LENGTH: 19
<212> TYPE: PRT
<213> ORGANISM: Artificial Sequence
<220> FEATURE:
<223> OTHER INFORMATION: Synthetic peptide

<400> SEQUENCE: 41

Val Leu Gly Lys Leu Ser Gln Asp Leu His Lys Leu Gln Thr Phe Pro
1               5                   10                  15

Arg Thr Asp

<210> SEQ ID NO 42
<211> LENGTH: 19
<212> TYPE: PRT
<213> ORGANISM: Artificial Sequence
<220> FEATURE:
<223> OTHER INFORMATION: Synthetic peptide

<400> SEQUENCE: 42

Met Leu Gly Lys Leu Ser Gln Asp Leu His Lys Leu Gln Thr Phe Pro
1               5                   10                  15

Arg Thr Asp

<210> SEQ ID NO 43
<211> LENGTH: 19
<212> TYPE: PRT
<213> ORGANISM: Artificial Sequence
<220> FEATURE:
<223> OTHER INFORMATION: Synthetic peptide

<400> SEQUENCE: 43

Val Leu Gly Lys Leu Ser Gln Asp Ile His Lys Leu Gln Thr His Pro
1               5                   10                  15

Arg Thr Asp

<210> SEQ ID NO 44
<211> LENGTH: 19
<212> TYPE: PRT
<213> ORGANISM: Artificial Sequence
<220> FEATURE:
<223> OTHER INFORMATION: Synthetic peptide

<400> SEQUENCE: 44

Val Leu Gly Lys Leu Ser Gln Asp Ile His Lys Leu Gln Thr His Pro
1               5                   10                  15

Arg Thr Asp

<210> SEQ ID NO 45
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(1)
<223> OTHER INFORMATION: Xaa = selected from the group consisting of
      Ala, Gly, Ile, Leu, Met, Phe, Pro, Trp, and Val
<220> FEATURE:
<221> NAME/KEY: VARIANT
<222> LOCATION: (2)...(2)
<223> OTHER INFORMATION: Xaa = selected from the group consisting of
      Ala, Gly, Ile, Leu, Met, Phe, Pro, Trp, and Val
<220> FEATURE:
<221> NAME/KEY: VARIANT
```

```
<222> LOCATION: (3)...(3)
<223> OTHER INFORMATION: Xaa = selected from the group consisting of Ser
      and Tyr
<220> FEATURE:
<221> NAME/KEY: VARIANT
<222> LOCATION: (4)...(4)
<223> OTHER INFORMATION: Xaa = selected from the group consisting of
      Arg, Asn, Asp, Glu, Gln, His, Lys, Ser, Thr, and Tyr
<220> FEATURE:
<221> NAME/KEY: VARIANT
<222> LOCATION: (5)...(5)
<223> OTHER INFORMATION: Xaa = selected from the group consisting of
      Ala, Gly, Ile, Leu, Met, Phe, Pro, Trp, and Val
<220> FEATURE:
<221> NAME/KEY: VARIANT
<222> LOCATION: (6)...(6)
<223> OTHER INFORMATION: Xaa = selected from the group consisting of
      Ala, Gly, Ile, Leu, Met, Phe, Pro, Trp, and Val

<400> SEQUENCE: 45

Xaa Xaa Xaa Xaa Xaa Xaa
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic peptide

<400> SEQUENCE: 46

Val Gly Ser Lys Ala Phe
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: C-terminal amine group

<400> SEQUENCE: 47

Val Gly Ser Lys Ala Phe
1               5

<210> SEQ ID NO 48

<400> SEQUENCE: 48

000

<210> SEQ ID NO 49
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (6)...(6)
<223> OTHER INFORMATION: Xaa = any amino acid residue other than Thr

<400> SEQUENCE: 49

Ala Cys Asp Thr Ala Xaa Cys
1               5
```

```
<210> SEQ ID NO 50
<211> LENGTH: 16
<212> TYPE: PRT
<213> ORGANISM: Artificial Sequence
<220> FEATURE:
<223> OTHER INFORMATION: Synthetic peptide

<400> SEQUENCE: 50

Glu Ala Ala Ala Lys Glu Ala Ala Ala Lys Glu Ala Ala Ala Lys Ala
1               5                  10                  15

<210> SEQ ID NO 51
<211> LENGTH: 17
<212> TYPE: PRT
<213> ORGANISM: Artificial Sequence
<220> FEATURE:
<223> OTHER INFORMATION: Synthetic peptide

<400> SEQUENCE: 51

Ala Lys Ala Ala Ala Glu Lys Ala Ala Ala Glu Lys Ala Ala Ala Glu
1               5                  10                  15

Ala

<210> SEQ ID NO 52
<211> LENGTH: 16
<212> TYPE: PRT
<213> ORGANISM: Artificial Sequence
<220> FEATURE:
<223> OTHER INFORMATION: Synthetic peptide

<400> SEQUENCE: 52

Ala Glu Ala Ala Lys Ala Glu Ala Ala Lys Ala Glu Ala Ala Lys Ala
1               5                  10                  15

<210> SEQ ID NO 53
<211> LENGTH: 16
<212> TYPE: PRT
<213> ORGANISM: Artificial Sequence
<220> FEATURE:
<223> OTHER INFORMATION: Synthetic peptide

<400> SEQUENCE: 53

Ala Lys Ala Ala Glu Ala Lys Ala Ala Glu Ala Lys Ala Ala Glu Ala
1               5                  10                  15

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57
<211> LENGTH: 32
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: C-terminal amine group

<400> SEQUENCE: 57

Ala Cys Asp Leu Ser Ala Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (32)..(32)
<223> OTHER INFORMATION: C-terminal amine group

<400> SEQUENCE: 58

Ala Cys Asp Leu Ser Val Cys Val Leu Gly Arg Leu Ser Gln Glu Leu
1               5                   10                  15

His Arg Leu Gln Thr Tyr Pro Arg Thr Asn Val Gly Ser Lys Ala Phe
            20                  25                  30
```

USE OF CGRP RECEPTOR ANTAGONISTS IN NEUROPROTECTION AND NEUROLOGICAL DISORDERS

INCORPORATION BY REFERENCE TO ANY PRIORITY APPLICATIONS

This application is a Continuation of and claims the benefit of priority to U.S. patent application Ser. No. 16/329,596 (now U.S. Pat. No. 11,390,654), filed on Feb. 28, 2019, which is a U.S. National Phase Application of PCT International Application Number PCT/US2017/049460 filed on Aug. 30, 2017, designating the United States of America and published in the English language, which claims the benefit of priority to U.S. Provisional Application No. 62/383,334, filed on Sep. 2, 2016, all of which are hereby expressly Incorporated by reference in their entireties.

REFERENCE TO SEQUENCE LISTING, TABLE, OR COMPUTER PROGRAM LISTING

The present application is being filed along with a Sequence Listing in electronic format. The Sequence Listing is provided as a file entitled CSOAR-003D1.TXT, created Jun. 9, 2022, which is 17 kb in size, which is replaced by a Replacement Electronic Sequence Listing submitted herewith as a file entitled CSOAR-003C1REPLACEMENTSEQLIST.txt, which is 17,806 bytes in size and was created on Nov. 13, 2023. The information is the electronic format of the Sequence Listing and is expressly incorporated herein by reference in its entirety.

FIELD OF THE INVENTION

The present embodiments relate to the therapeutic use of antagonists of the calcitonin gene-related peptide (CGRP) receptor for neuroprotection and in the treatment of acute and chronic diseases and disorders associated with neurodegeneration, including for example, treatment of glaucoma. In addition, methods of treating diseases related to high LDL levels, using the antagonists, are provided herein.

BACKGROUND

Calcitonin gene-related peptide (CGRP), a member of the calcitonin family of peptides, is a potent 37-amino acid peptide vasodilator that has an important role in the pathogenesis of several pain syndromes, such as migraine, and thermal injury. In addition to its role in vasodilation, CGRP can exert a broad range of biological effects.

CGRP (calcitonin gene-related peptide) is a well-studied peptide in the calcitonin/calcitonin gene-related peptide (CT/CGRP) family of peptide hormones, which can act as a sensory neuropeptide with potent vasodilatory and cardiotonic action as described in U.S. Pat. No. 4,530,838 to Evans, et al. CGRP is present in both the central and peripheral nervous systems and is concentrated in those areas of the body receiving sensory input from the dorsal horn with limited amounts associated with autonomic input. In the brain, the peptide is present in the nuclei of sensory and motor cranial nerves and in cell bodies in the hypothalamus, preoptic area, ventromedial thalamus, hippocampus, and the like (Poyner et al. 1992).

The CT/CGRP peptide family includes calcitonin gene-related peptide (CGRP), adrenomedullin (ADM), intermedin (IM), calcitonin (CT) and amylin. The biological actions of these peptides are mediated via binding to two closely related type II G protein-coupled receptors (GPCRs), the calcitonin receptor (CTR) and the calcitonin receptor-like receptor (CRLR) (Christopoulos, et al. 1999; Poyner et al. 2002). The calcitonin receptor is the main mediator for calcitonin action. However, it preferentially binds amylin, when the receptor is associated with a receptor activity modifying protein (RAMP) (see, e.g., Tilikaratne, et al. 2000). Cloning and functional studies have shown that CGRP, ADM, IM and, to a lesser extent, amylin likewise interact with different combinations of CRLR and the three receptor activity modifying proteins (RAMP-1, RAMP-2 and RAMP-3) (see, e.g., McLatchie et al. 1998, and Roh et al. 2004). Co-expression of the calcitonin receptor-like receptor (CRLR) and receptor activity-modifying proteins (RAMPs) is required to generate functional heterodimer receptors for calcitonin gene-related peptide (CGRP), adrenomedullin (ADM) and intermedin (IM). Co-expression of RAMP-1 with CRLR leads to the formation of a CGRP receptor, whereas RAMP-2 and RAMP-3 co-expression with CRLR form ADM and IM receptors, respectively (Miret, et al. 2002). IM has been shown to be a nonselective agonist for all three RAMP/CRLR co-receptors.

CGRP initiates biological responses by binding to the CGRP receptor. The CGRP receptors are composed of 3 subunits: a 7 transmembrane protein called the calcitonin-like receptor (CLR), a single transmembrane protein that determines ligand specificity called receptor activity modifying protein 1 (RAMP1) and an intracellular protein called receptor component protein (RCP). The CGRP receptor is coupled to the Gas signaling pathway leading to increased intracellular cAMP and activated protein kinase A (PKA) (Poyner et al., 2002).

CGRP receptors are found in multiple areas, including for example: 1) the cerebrovasculature smooth muscle, where they can cause relaxation of the vessels (Poyner et al., 2002); 2) dural mast cells from which CGRP has been shown to release pro-inflammatory cytokines and inflammatory agents during neurogenic inflammation (Marquest et al., 2006); 3) trigeminal ganglia neurons (Zhang et al., 2007) and second order sensory neurons within trigeminal nuclei in the caudal brainstem which is responsible for the transfer of pain sensation (Russo et al., 2015).

CGRP receptors are expressed in the central and peripheral nervous system (Cumberbatch et al., 1999; Marquez de Prado et al., 2006). Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has particularly been implicated in the pathogenesis of migraine headache (Edvinsson et al. 2001; Grant et al., 2002). Migraines are noted for the strength of the headache that ensues with its pathology. It is postulated that the headache associated with migraines results from the profound cerebral vasodilation associated with migraine events. CGRP-containing nerve fibers innervate cerebral and dural vessels where CGRP is believed to prolong vasodilation. (Moskowitz et al. 1992). Further, serum levels of CGRP are elevated during migraine (Goadsby, et al. 1990), and treatment with anti-migraine drugs returns CGRP levels to normal coincident with alleviation of headache (Gallai, et al. 1995). Migraineurs exhibit elevated basal CGRP levels compared to controls (Ashina, et al., 2000). Intravenous CGRP infusion produces lasting headache in migraineurs (Lassen, et al. 2002). CGRP antagonist peptides and their use in the treatments of migraines have been described in U.S. patent application Ser. No. 13/821,936 filed on Mar. 8, 2013 (Soares et al.), hereby incorporated by reference in its entirety.

Nerve injury can also lead to high levels of CGRP in the nerves and spinal cord. In a study performed by MDBiosciences, levels of CGRP mRNA were markedly increased in pigs that sustained neuritis neuropathy due to sciatic nerve injury (Castel et al. 2016).

Antagonists of the CGRP receptor are known, including small molecule, peptide and antibody antagonists. Small molecule antagonists of the CGRP receptor include, for example, the gepant class of molecules, such as olcegepant, telcagepant and ubrogepant. Peptide antagonists include, for example, truncated CGRP peptides such as CGRP (8-37), CGRP (28-37), [Tyr°]CGRP (28-37), and CGRP (12-37); h-α-CGRP (9-37), h-α-CGRP (10-37), h-α-CGRP (11-37) (Mimeault, M. et al., 1992); [Ala$^9$]-h-α-CGRP (8-37), [Ala$^{10}$]-h-α-CGRP (8-37), [Ala$^{11}$]-h-α-CGRP (8-37), and [Ala$^{12}$]-h-α-CGRP (8-37), id; and h-α-CGRP (19-37), h-α-CGRP (23-37) and acetyl-h-α-CGRP (19-37) (Rovero, P. et al. 1992).

Non-truncated peptide antagonists of CGRP receptors are described, for example, herein and in Soares, C J, PCT Patent Publication WO 2013/112912, published Aug. 1, 2013. Such non-truncated, or full length peptide antagonists of CGRP receptors have been shown to be highly potent antagonists that would not be expected to have off-target effects, as seen with many small molecule antagonists. Additionally, antibodies binding CGRP receptors are known, such as AMG 334, as are antibodies to the CGRP ligand, such as LY2951742, ALD403 and TEV-48125. To date, such CGRP receptor and ligand antibodies have been investigated for use in treatment of pain-related disorders such as migraine and osteoarthritis pain.

Every year, millions of people worldwide suffer the consequences of neurodegeneration caused by injury or disease. The umbrella term, neurodegenerative disease, refers to the progressive loss of structure and/or function of the neurons including the death of neurons. Examples of neurodegenerative disease include glaucoma, amyotrophic lateral sclerosis, multiple sclerosis, Creutzfeld-Jakob disease, epilepsy, Parkinson's, Alzheimer's, diabetic neuropathy and Huntington's disease (Gupta, et al., 2007; Song et al., 2016; Mufson et al). To date, no cures exist for such diseases which typically result in progressive degeneration and/or the death of neuron cells and can result in death of the patient. Neurodegeneration can be found in many different levels of neuronal circuitry ranging from molecular to systemic.

Glaucoma is a neurodegenerative disease that is one of the most common causes of blindness, affecting over 70 million people worldwide. An age-related, chronic degenerative disease of the optic nerve, retina, and brain, glaucoma exhibits similarities to the molecular and cellular features of other chronic degenerations of the neurologic systems, including amyotrophic lateral sclerosis. The underlying mechanisms leading to glaucoma are still under investigation, however one well-established cause of glaucoma is the damage to retinal ganglion cells from the result of mechanical injury stemming from intraocular pressure caused by disruption of the trabecular meshwork (Nafissi et al. 2015). Glaucoma comprises a group of several eye diseases that lead to damage to the optic nerve and, too often, vision loss. While glaucoma is generally characterized by the increase of intraocular pressure (IOP), damage to the ganglion cells of the retina and the optic nerve without concomitant increase in IOP is also a known form of glaucoma (normotensive glaucoma). Similarly, genetic mutation and oxidative insult can lead to ganglion cell apoptosis. As such, there is a need to develop strategies for protecting the ganglion cells of the retina and the optic nerve.

In a recent review of glaucoma, it was suggested that axonopathy, a disorder affecting primarily the normal functioning of axons of peripheral nerve fibers in the brain can also lead to glaucoma (Chader et al., 2012). The changes in the optic nerve and the optic nerve head can include impairment of transport of molecules in the fibers of the optic nerve that causes glaucomatous damage to accumulate as the patient gets older. Injury of specialized brain structures is also seen in the early stages of glaucoma. Glaucoma can also stem from a complication from diabetic eye disease. People with diabetes are twice as likely to develop glaucoma compared to non-diabetics as they age.

Thus, neurodegeneration is a complex disease, in which several groups of people are at a substantially higher risk than the general population for developing diseases that affect the nerve fibers. One of the greatest risk factor for neurodegenerative diseases is aging. For example, mitochondrial DNA mutations as well as oxidative stress are associated both with aging and other neurodegeneration.

Aging is another factor that can lead to glaucoma. For example, aging can play a role in the development of primary open-angle glaucoma (POAG). As such, advances in other age-related diseases may be useful in the development of a variety of treatments. For example, methods that are developed to protect the neurons of the optic tract may also be applied to other nervous system diseases, such as Alzheimer's disease and AMD, for example, where neurons are in need of protection.

Thus far, treatments for have focused on lowering intraocular pressure, such as the FDA-approved prostaglandins (i.e. Xalatan, Lumigan, Travatan Z and Rescula), beta-blockers (i.e. Timoptic XE, Istalol and Betopic) and alpha adrenergic agonists (i.e. iopidine, Alphagan and Alphagan-P). Some of these drugs were first used for other purposes but were subsequently found to be safe and efficacious in treating glaucoma. As these drugs are drops applied to the surface of the eye, they are relatively low risk. However, these drugs are not effective in all cases of glaucoma and do not constitute a cure, but they can be used to prolong functional vision in treated patients. Thus there remains a need for therapies that achieve better management of the disease, further reducing or preventing vision loss.

Methods to protect neurons can lead to inhibiting the onset of neurodegenerative diseases and inhibiting damage of neurons, including retinal neurons, such as photoreceptor cells against cell death (apoptosis) or can lead to slowing of neurodegenerative disease progression and associated damage to neurons. Thus these new methods can be used to prevent and/or slow nerve injury or protect retinal neurons or nerves in the peripheral or central nervous system.

SUMMARY

The present disclosure is based on the discovery that CGRP receptor antagonists, including, for example, peptide antagonists, can be used to inhibit or decrease neuronal damage including neuronal death and provide neuroprotection. CGRP receptor antagonists and compositions comprising the same can be used to treat neurodegenerative diseases. Without being limiting, these CGRP antagonist peptides and compositions can be used to protect neurons from acute or chronic damage, inhibiting or slowing cell death and thereby treating disorders associated with neuronal damage such as, for example, glaucoma, neuropathy, spontaneous nerve activity and neuritis.

Also disclosed is the use of CGRP receptor antagonists to reduce levels of LDL, thereby treating diseases resulting from high LDL levels.

In a first aspect, a method of reducing spontaneous activity of nerves in a patient, in need thereof is provided. The method comprises administering to the patient an effective amount of CGRP receptor antagonist including a pharmaceutically acceptable salt thereof. In some embodiments, the CGRP receptor antagonist is a peptide comprising a structure of Formula I.

$$X^1 - Y^1 - Z^1 \quad (I)$$

wherein $X^1$ is a modified N-terminal fragment (i.e., region) of calcitonin gene-related peptide comprising from five to seven amino acid residues, wherein only two amino acid residues of the N-terminal fragment are cysteine (Cys), wherein the residue at the C-terminal end of the region is Cys, and wherein the residue immediately preceding the C-terminal Cys residue of the region is a non-threonine substitution of the threonine (Thr) residue of position 6 of human CGRP, $Y^1$ is a central core region wherein at least one amino acid of the central core is arginine (Arg) or lysine (Lys) and the central core comprises an α-helix, and $Z^1$ is a modified C-terminal fragment (i.e., region) of calcitonin gene-related peptide comprising from five to seven amino acid residues with a C-terminal amide, where at least one amino acid of the C-terminal fragment is phenylalanine (Phe), tyrosine (Tyr), proline (Pro) or hydroxyproline (Hyp). In some embodiments, the CGRP receptor antagonist is a peptide comprising a sequence set forth in one of SEQ ID NO: 1 (NH2-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 2 (NH2-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 3 (NH2-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 4 (NH2-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 5 (NH2-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 6 (NH2-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 7 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 8 (NH2-Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 9 (NH2-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 10 (NH2-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 11 (NH2-Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 12 (NH2-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 13 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Thr-Asn-Thr-Gly-Ser-Gly-Thr-Pro-NH2), SEQ ID NO: 14 (Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Val-Asp-Pro-Ser-Ser-Pro-His-Ser-Tyr-NH2), SEQ ID NO: 15 (Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH2), SEQ ID NO: 57 (NH2-Ala-Cys-Asp-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or SEQ ID NO: 58 (NH2-Ala-Cys-Asp-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or a pharmaceutically acceptable salt thereof. In some embodiments, the CGRP receptor antagonist comprises a sequence selected from the group consisting of the sequences set forth in SEQ ID NO: 1, 2, 3, 4, 5, 6, 7, 8, 9, 10, 11, 12 and 13. In some embodiments, the CGRP receptor antagonist is administered topically, dermally, intradermally, subcutaneously, via dermal infusion, via subcutaneous infusion, intraocularly, buccally, intravenously, nasally, via inhalation, intramuscularly, sublingually or orally. In some embodiments, the effective amount comprises an amount of about 50 µg, 60 µg, 70 µg, 80 µg, 90 µg, 100 µg, 200 µg, 300 µg, 400 µg, 500 µg, 600 µg, 700 µg, 800 µg, 900 µg, 1 mg, 5 mg, 10 mg, 40 mg, 50 mg, 100 mg, 200 mg, 300 mg, 400 mg, 500 mg, 600 mg, 700 mg, 800 mg, 900 mg or 1000 mg or any amount in between a range defined by any two aforementioned values. In some embodiments, the administering is performed at least once daily, once a week, twice a week or three times a week, or four times a week. In some embodiments, the spontaneous nerve activity is due to a nerve injury or neurodegenerative disease. In some embodiments, the nerve injury is from a physical injury, diabetes, cancer, diabetic neuropathy, head injury, seizures, infection, or ingestion of a pharmaceutical or drug, such as a chemotherapeutic. In some embodiments, the neurodegenerative disease is amyotrophic lateral sclerosis, multiple sclerosis, Creutzfeld-Jakob disease, epilepsy, Parkinson's, Alzheimer's, glaucoma, cerebrovascular ischemia, motor neuron disease, dementia, diabetic neuropathy or Huntington's disease. In some embodiments, the patient has been identified or selected to receive a drug for neurodegenerative diseases, neurovascular disorder or disease such as cancer. In some embodiments, the drug is associated with spontaneous nerve activity and/or nerve damage. In some embodiments, wherein the nerve injury is from a pharmaceutical or drug, the pharmaceutical or drug is a heart medication (i.e. almitrine), an anti-cancer drug, antibiotic (i.e. chlorampheticol, Cipro), anti-fungal, immunosuppressant drug (i.e. Cyclosporine), muscle relaxant (i.e. Hydrazaline), anti-seizure medications (i.e. Phenytoin), anti-viral, anti-HIV drug, anti-inflammatory, centrally-acting muscle relaxant, nootropica agent, apoptosis inhibitor, growth factor agonist, smooth muscle relaxantium, chloroquine, isoniazid, metronidazole, nitrofurantoin, thalidomide, etanercept, infliximab, leflunomide, dapsone, phenytoin, disulfiram, didanosine, stavudine, Kenalog-40, triamcinolone, Clinacort or antiparasitic. In some embodiments, the method further comprises introducing, providing or administering to said patient the drug before, during or after administering the CGRP receptor antagonist. In some embodiments, the CGRP receptor antagonist is used in combination with the drug. In some embodiments, the method further comprises monitoring or measuring a level of nerve activity function in said patient before, during or after administration of the effective amount of CGRP receptor antagonist. In some embodiments, the nerves are C-Nociceptors or Group C nerve fibers. In some embodiments the method further comprises reducing pain associated with spontaneous nerve activity in a patient in need thereof, by administration of a CGRP antagonist. In some embodiments, the CGRP receptor antagonist is administered within a pharmaceutically acceptable formulation.

In a second aspect, a method of providing neuroprotection in a patient in need thereof is provided. The method comprises administering to the patient an effective amount of CGRP receptor antagonist including a pharmaceutically acceptable salt thereof. In some embodiments, the CGRP receptor antagonist is a peptide comprising a structure of Formula I:

$$X^1-Y^1-Z^1 \qquad (I)$$

wherein $X^1$ is a modified N-terminal fragment (i.e. region) of calcitonin gene-related peptide comprising from five to seven amino acid residues, wherein only two amino acid residues of the N-terminal fragment are cysteine (Cys), wherein the C-terminal residue of the fragment is Cys, and wherein the residue immediately preceding the C-terminal Cys residue of the region is a non-threonine substitution of a threonine (Thr) residue, $Y^1$ is a central core wherein at least one amino acid of the central core is arginine (Arg) or lysine (Lys) and the central core comprises an α-helix, and $Z^1$ is a modified C-terminal fragment (i.e. region) of calcitonin gene-related peptide comprising from five to seven amino acid residues with a C-terminal amide, where at least one amino acid of the C-terminal fragment is phenylalanine (Phe), tyrosine (Tyr), proline (Pro) or hydroxyproline (Hyp). In some embodiments, the CGRP receptor antagonist comprises a sequence set forth in one of SEQ ID NO: 1 (NH2-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 2 (NH2-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 3 (NH2-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 4 (NH2-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 5 (NH2-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 6 (NH2-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 7 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 8 (NH2-Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 9 (NH2-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 10 (NH2-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 11 (NH2-Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 12 (NH2-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 13 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Thr-Asn-Thr-Gly-Ser-Gly-Thr-Pro-NH2), SEQ ID NO: 14 (Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Val-Asp-Pro-Ser-Ser-Pro-His-Ser-Tyr-NH2), SEQ ID NO: 15 (Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH2), SEQ ID NO: 57 (NH2-Ala-Cys-Asp-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or SEQ ID NO: 58 (NH2-Ala-Cys-Asp-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or a pharmaceutically acceptable salt thereof. In some embodiments, the CGRP antagonist comprises a sequence selected from the group consisting of the sequences set forth in SEQ ID NO: 1, 2, 3, 4, 5, 6, 7, 8, 9, 10, 11, 12 and 13. In some embodiments, the CGRP receptor antagonist is administered topically, dermally, intradermally, subcutaneously, via dermal infusion, via subcutaneous infusion, intraocularly, buccally, intravenously, nasally, via inhalation, intramuscularly, sublingually or orally. In some embodiments, the effective amount comprises an amount of about 50 μg, 60 μg, 70 μg, 80 μg, 90 μg, 100 μg, 200 μg, 300 μg, 400 μg, 500 μg, 600 μg, 700 μg, 800 μg, 900 μg, 1 mg, 5 mg, 10 mg, 40 mg, 50 mg, 100 mg, 200 mg, 300 mg, 400 mg, 500 mg, 600 mg, 700 mg, 800 mg, 900 mg or 1000 mg or any amount in between a range defined by any two aforementioned values. In some embodiments, the administering is performed at least once daily, once a week, twice a week or three times a week, or four times a week. In some embodiments, the patient is suffering from a nerve injury, neurodegenerative disease or a disease such as cancer. In some embodiments, the nerve injury is from a physical injury, diabetes, cancer, diabetic neuropathy, head injury, seizures, infection, or ingestion of a pharmaceutical or a drug, such as a chemotherapeutic. In some embodiments, the neurodegenerative disease is amyotrophic lateral sclerosis, multiple sclerosis, Creutzfeld-Jakob disease, epilepsy, Parkinson's, Alzheimer's, glaucoma, cerebrovascular ischemia, motor neuron disease, dementia, diabetic neuropathy, Huntington's disease, seizures or head injury. In some embodiments, the patient has been identified or selected to receive neuroprotection treatment. In some embodiments, the method further comprises monitoring or measuring a level of nerve activity function in said patient before, during or after administration of the effective amount of CGRP receptor antagonist. In some embodiments, the patient has been identified or selected to receive a drug. In some embodiments, the drug is associated with side effects related to neuronal dysfunction. In some embodiments, the drug associated with neuronal dysfunction is a heart medication (i.e. almitrine), an anti-cancer drug, antibiotic (i.e. chlorampheticol, Cipro), anti-fungal, immunosuppressant drug (i.e. Cyclosporine), muscle relaxant (i.e. Hydrazaline), anti-seizure medications (i.e. Phenytoin), anti-viral, anti-HIV drug, anti-inflammatory, centrally-acting muscle relaxant, nootropica agent, apoptosis inhibitor, growth factor agonist, smooth muscle relaxantium, chloroquine, isoniazid, metronidazole, nitrofurantoin, thalidomide, etanercept, infliximab, leflunomide, dapsone, phenytoin, disulfiram, didanosine, stavudine, Kenalog-40, triamcinolone, Clinacort or antiparasitic. In some embodiments, the CGRP receptor antagonist is administered within a pharmaceutically acceptable formulation. In some embodiments, the method further comprises introducing, providing or administering to said patient the drug before, during or after administering the CGRP receptor antagonist. In some embodiments, the CGRP receptor antagonist is used in combination with the drug.

In a third aspect, a method of treating neuritis in a patient in need thereof is provided. The method comprises administering to the patient an effective amount of CGRP receptor antagonist or pharmaceutically acceptable salt thereof. In some embodiments, the CGRP receptor antagonist is a peptide or pharmaceutically acceptable salt thereof comprising a structure of Formula I.

$$X^1-Y^1-Z^1 \qquad (I)$$

wherein $X^1$ is a modified N-terminal fragment (i.e. region) of calcitonin gene-related peptide comprising from five to seven amino acid residues, wherein only two amino acid residues of the N-terminal fragment are cysteine (Cys), wherein the amino acid residue at the C-terminal end of the fragment (region) is Cys, and wherein the residue immediately preceding the C-terminal Cys residue is a non-threonine substitution of the threonine (Thr) residue found at position 6 of human CGRP, $Y^1$ is a central core region wherein at least one amino acid of the central core is arginine (Arg) or lysine (Lys) and the central core comprises an α-helix, and $Z^1$ is a modified C-terminal fragment (i.e. region) of calcitonin gene-related peptide comprising from five to seven amino acid residues with a C-terminal amide, where at least one amino acid of the C-terminal fragment is phenylalanine (Phe), tyrosine (Tyr), proline (Pro) or hydroxyproline (Hyp). In some embodiments, the CGRP receptor antagonist is a peptide comprising a sequence set forth in one of SEQ ID NO: 1 (NH2-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 2 (NH2-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 3 (NH2-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 4 (NH2-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 5 (NH2-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 6 (NH2-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 7 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 8 (NH2-Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 9 (NH2-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 10 (NH2-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 11 (NH2-Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 12 (NH2-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 13 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Thr-Asn-Thr-Gly-Ser-Gly-Thr-Pro-NH2), SEQ ID NO: 14 (Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Val-Asp-Pro-Ser-Ser-Pro-His-Ser-Tyr-NH2), SEQ ID NO: 15 (Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH2), SEQ ID NO: 57 (NH2-Ala-Cys-Asp-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or SEQ ID NO: 58 (NH2-Ala-Cys-Asp-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or a pharmaceutically acceptable salt thereof. In some embodiments, the CGRP antagonist comprises a sequence selected from the group consisting of the sequences set forth in SEQ ID NO: 1, 2, 3, 4, 5, 6, 7, 8, 9, 10, 11, 12 and 13. In some embodiments, the CGRP receptor antagonist is administered topically, dermally, intradermally, subcutaneously, via dermal infusion, via subcutaneous infusion, intraocularly, buccally, intravenously, nasally, via inhalation, intramuscularly, sublingually or orally. In some embodiments, the effective amount comprises an amount of about 50 μg, 60 μg, 70 μg, 80 μg, 90 μg, 100 μg, 200 μg, 300 μg, 400 μg, 500 μg, 600 μg, 700 μg, 800 μg, 900 μg, 1 mg, 5 mg, 10 mg, 40 mg, 50 mg, 100 mg, 200 mg, 300 mg, 400 mg, 500 mg, 600 mg, 700 mg, 800 mg, 900 mg or 1000 mg or any amount in between a range defined by any two aforementioned values. In some embodiments, the administering is performed at least once daily, once a week, twice a week or three times a week, or four times a week. In some embodiments, the method further comprises monitoring or measuring a level of nerve activity function in said patient before, during or after administration of the effective amount of CGRP receptor antagonist. In some embodiments, the patient has been identified or selected to receive a drug. In some embodiments the drug can cause neuronal dysfunction. In some embodiments, the neuritis is from a physical injury, vascular injury, toxin, aging, a genetic disorder, infection (viral or bacterial), diphtheria, herpes zoster (shingles), leprosy, Lyme disease, chemical injury such as chemotherapy, radiation therapy, alcoholism, autoimmune disease, multiple sclerosis, Guillain-Barre syndrome, beriberi (vitamin B1 deficiency), cancer, Celiac disease, diabetes (Diabetic neuropathy), hypothyroidism, porphyria, vitamin B12 deficiency, vitamin B6 excess, brachial neuritis, cranial neuritis, Bell's palsy, optic neuritis or vestibular neuritis. In some embodiments, the CGRP receptor antagonist is administered within a pharmaceutically acceptable formulation. In some embodiments, the drug causing neuronal dysfunction is a heart medication (i.e. almitrine), an anti-cancer drug, antibiotic (i.e. chlorampheticol, Cipro), anti-fungal, immunosuppressant drug (i.e. Cyclosporine), muscle relaxant (i.e. Hydrazaline), anti-seizure medications (i.e. Phenytoin), anti-viral, anti-HIV drug, anti-inflammatory, centrally-acting muscle relaxant, nootropica agent, apoptosis inhibitor, growth factor agonist, smooth muscle relaxantium, chloroquine, isoniazid, metronidazole, nitrofurantoin, thalidomide, etanercept, infliximab, leflunomide, dapsone, phenytoin, disulfiram, didanosine, stavudine, Kenalog-40, triamcinolone, Clinacort or antiparasitic. In some embodiments, the method further comprises introducing, providing or administering to said patient the drug before, during or after administering the CGRP receptor antagonist.

In a fourth aspect, a method of treating glaucoma in a patient is provided. The method comprises administering to the patient an effective amount of CGRP receptor antagonist or pharmaceutically acceptable salt thereof. In some embodiments, the CGRP receptor antagonist is a peptide or pharmaceutically acceptable salt thereof comprising a structure of Formula I.

$$X^1\text{—}Y^1\text{—}Z^1 \qquad (I)$$

wherein $X^1$ is a modified N-terminal fragment (i.e., region) of calcitonin gene-related peptide comprising from five to seven amino acid residues, wherein only two amino acid residues of the N-terminal fragment are cysteine (Cys), wherein the residue at the C-terminal end of the fragment is Cys, and wherein the residue immediately preceding the C-terminal Cys residue of the region is a non-threonine substitution of the threonine (Thr) residue of position 6 of human CGRP, $Y^1$ is a central core region wherein at least one amino acid of the central core is arginine (Arg) or lysine (Lys) and the central core comprises an α-helix and $Z^1$ is a modified C-terminal fragment (i.e. region) of calcitonin gene-related peptide comprising from five to seven amino acid residues with a C-terminal amide, where at least one amino acid of the C-terminal region is phenylalanine (Phe), tyrosine (Tyr), proline (Pro) or hydroxyproline (Hyp). In some embodiments, the CGRP receptor antagonist is a peptide comprising a sequence set forth in one of SEQ ID NO: 1 (NH2-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 2 (NH2-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 3 (NH2-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 4 (NH2-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 5 (NH2-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 6 (NH2-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 7 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 8 (NH2-Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 9 (NH2-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 10 (NH2-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 11 (NH2-Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 12 (NH2-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 13 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Thr-Asn-Thr-Gly-Ser-Gly-Thr-Pro-NH2), SEQ ID NO: 14 (Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Val-Asp-Pro-Ser-Ser-Pro-His-Ser-Tyr-NH2), SEQ ID NO: 15 (Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH2), SEQ ID NO: 57 (NH2-Ala-Cys-Asp-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or SEQ ID NO: 58 (NH2-Ala-Cys-Asp-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or a pharmaceutically acceptable salt thereof. In some embodiments, the CGRP antagonist comprises a sequence selected from the group consisting of the sequences set forth in SEQ ID NO: 1, 2, 3, 4, 5, 6, 7, 8, 9, 10, 11, 12 and 13. In some embodiments, the CGRP receptor antagonist is administered topically, dermally, intradermally, subcutaneously, via dermal infusion, via subcutaneous infusion, intraocularly, buccally, intravenously, nasally via inhalation, intramuscularly, sublingually or orally. In some embodiments, wherein the effective amount comprises an amount of about 50 µg, 60 µg, 70 µg, 80 µg, 90 µg, 100 µg, 200 µg, 300 µg, 400 µg, 500 µg, 600 µg, 700 µg, 800 µg, 900 µg, 1 mg, 10 mg, 20 mg, 30 mg, 40 mg, 50 mg, 100 mg, 200 mg, 300 mg, 400 mg, 500 mg, 600 mg, 700 mg, 800 mg, 900 mg or 1000 mg or any amount in between a range defined by any two aforementioned values. In some embodiments, the administering is performed at least four times a day, three times a day, two times a day, or once a day. In some embodiments, the patient has diabetes. In some embodiments, the patient has been identified or selected to receive a drug for glaucoma. In some embodiments, the drug can cause nerve or central nervous system damage or neuronal dysfunction (i.e. beta blocker). In some embodiments, the CGRP receptor antagonist is administered within a pharmaceutically acceptable formulation. In some embodiments, the method further comprises introducing, providing or administering to said patient the drug before, during or after administering the CGRP receptor antagonist. In some embodiments, the CGRP receptor antagonist is used in combination with the drug.

In a fifth aspect, a method of reducing LDL in a patient in need thereof is provided. The method comprises administering to the patient an effective amount of CGRP receptor antagonist or pharmaceutically acceptable salt thereof. In some embodiments, the CGRP receptor antagonist is a peptide or pharmaceutically acceptable salt thereof comprising a structure of Formula I:

$$X^1\text{—}Y^1\text{—}Z^1 \qquad (I)$$

wherein $X^1$ is a modified N-terminal fragment (i.e., region) of calcitonin gene-related peptide comprising from five to seven amino acid residues, wherein only two amino acid residues of the N-terminal fragment are cysteine (Cys), wherein the residue at the C-terminal end of the region is Cys, and wherein the residue immediately preceding the C-terminal Cys residue of the region is a non-threonine substitution of the threonine (Thr) residue of position 6 of human GCRP, $Y^1$ is a central core region wherein at least one amino acid of the central core is arginine (Arg) or lysine (Lys) and the central core comprises an α-helix and $Z^1$ is a modified C-terminal fragment (i.e., region) of calcitonin gene-related peptide comprising from five to seven amino acid residues with a C-terminal amide, where at least one amino acid of the C-terminal fragment is phenylalanine (Phe), tyrosine (Tyr), proline (Pro) or hydroxyproline (Hyp). In some embodiments, the CGRP receptor antagonist is a peptide comprising a sequence set forth in one of SEQ ID NO: 1 (NH2-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 2 (NH2-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 3 (NH2-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 4 (NH2-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 5 (NH2-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 6 (NH2-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 7 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 8 (NH2-Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 9 (NH2-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 10 (NH2-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 11 (NH2-Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 12 (NH2-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 13 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Thr-Asn-Thr-Gly-Ser-Gly-Thr-Pro-NH2), SEQ ID NO: 14 (Ala-Cys-Val-Leu-Gly-Ala-Cys-Val-Leu-Gly-Arg-Leu-Gly-Leu-Ser-Glu-Leu-His-Arg-Leu-Gln-Thr-Tyr-Pro-Val-Asp-Pro-Ser-Ser-Pro-His-Ser-Tyr-NH2), SEQ ID NO: 15 (Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH2), SEQ ID NO: 57 (NH2-Ala-Cys-Asp-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or SEQ ID NO: 58 (NH2-Ala-Cys-Asp-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or a pharmaceutically acceptable salt thereof. In some embodiments, the CGRP antagonist comprises a sequence selected from the group consisting of the sequences set forth in SEQ ID NO: 1, 2, 3, 4, 5, 6, 7, 8, 9, 10, 11, 12 and 13. In some embodiments, the patient is suffering from high LDL concentration in the blood. In some embodiments, the method further comprises monitoring or measuring the level or amount of LDL in said patient before, during, or after administration of the effective amount of CGRP receptor antagonist. In some embodiments, the patient is a male. In some embodiments, the patient has familial hypercholesterolemia. In some embodiments, the CGRP receptor antagonist is administered dermally, intradermally, subcutaneously, via dermal infusion, via subcutaneous infusion, intravenously, buccally, intramuscularly, sublingually or orally. In some embodiments, wherein the effective amount comprises an amount of about 50 µg, 60 µg, 70 µg, 80 µg, 90 µg, 100 µg, 200 µg, 300 µg, 400 µg, 500 µg, 600 µg, 700 µg, 800 µg, 900 µg, 1 mg, 10 mg, 20 mg, 30 mg, 40 mg, 50 mg, 100 mg, 200 mg, 300 mg, 400 mg, 500 mg, 600 mg, 700 mg, 800 mg, 900 mg or 1000 mg or any amount in between a range defined by any two aforementioned values. In some embodiments, the administering is performed at least four times a day, three times a day, two times a day, or once a day.

In a sixth aspect, a method of protecting a patient from nerve damage or nerve inflammation is provided. The method comprises administering to the patient an effective amount of CGRP receptor antagonist or pharmaceutically acceptable salt thereof. In some embodiments, the patient suffers from a post ischemic event. In some embodiments, the CGRP receptor antagonist is a peptide or a pharmaceutically acceptable salt thereof comprising a structure of Formula I:

$$X^1—Y^1—Z^1 \qquad (I)$$

wherein $X^1$ is a modified N-terminal fragment (i.e., region) of calcitonin gene-related peptide comprising from five to seven amino acid residues, wherein only two amino acid residues of the N-terminal fragment are cysteine (Cys), wherein the residue at the C-terminal end of the region is Cys, and wherein the residue immediately preceding the C-terminal Cys residue of the region is a non-threonine substitution of the threonine (Thr) residue of position 6 of human CGRP, $Y^1$ is a central core region wherein at least one amino acid of the central core is arginine (Arg) or lysine (Lys) and the central core comprises an α-helix and $Z^1$ is a modified C-terminal fragment (i.e., region) of calcitonin gene-related peptide comprising from five to seven amino acid residues with a C-terminal amide, where at least one amino acid of the Z1 region is phenylalanine (Phe), tyrosine (Tyr), proline (Pro) or hydroxyproline (Hyp). In some embodiments, the CGRP receptor antagonist is a peptide comprising a sequence set forth in one of SEQ ID NO: 1 (NH2-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 2 (NH2-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 3 (NH2-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 4 (NH2-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 5 (NH2-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 6 (NH2-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 7 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 8 (NH2-Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 9 (NH2-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg- Thr-Asn-Val-Gly-Ser-Lys-Ala-Phe-NH2), SEQ ID NO: 10 (NH2-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 11 (NH2-Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 12 (NH2-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 13 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Thr-Asn-Thr-Gly-Ser-Gly-Thr-Pro-NH2), SEQ ID NO: 14 (Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Val-Asp-Pro-Ser-Ser-Pro-His-Ser-Tyr-NH2), SEQ ID NO: 15 (Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH2), SEQ ID NO: 57 (NH2-Ala-Cys-Asp-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or SEQ ID NO: 58 (NH2-Ala-Cys-Asp-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or a pharmaceutically acceptable salt thereof. In some embodiments, the CGRP antagonist comprises a sequence selected from the group consisting of the sequences set forth in SEQ ID NO: 1, 2, 3, 4, 5, 6, 7, 8, 9, 10, 11, 12 and 13. In some embodiments, the CGRP receptor antagonist is administered topically, dermally, intradermally, subcutaneously, via dermal infusion, via subcutaneous infusion, intraocularly, buccally, intravenously, nasally, via inhalation, intramuscularly, sublingually or orally. In some embodiments, the effective amount comprises an amount of about 50 µg, 60 µg, 70 µg, 80 µg, 90 µg, 100 µg, 200 µg, 300 µg, 400 µg, 500 µg, 600 µg, 700 µg, 800 µg, 900 µg, 1 mg, 10 mg, 20 mg, 30 mg, 40 mg, 50 mg, 100 mg, 200 mg, 300 mg, 400 mg, 500 mg, 600 mg, 700 mg, 800 mg, 900 mg or 1000 mg or any amount in between a range defined by any two aforementioned values. In some embodiments, the administering is performed at least four times a day, three times a day, two times a day, or once a day.

In a seventh aspect, an effective amount of calcitonin gene-related peptide (CGRP) receptor antagonist, or a pharmaceutically acceptable salt thereof is provided, for use in reducing spontaneous nerve activity of nerves in a patient in need thereof. In some embodiments of the calcitonin gene-related peptide (CGRP) receptor antagonist for use, the CGRP receptor antagonist is a peptide comprising a structure of Formula I:

X1—Y1—Z1     (I)

wherein:
X1 is a modified N-terminal fragment (i.e., region) of calcitonin gene-related peptide comprising from five to seven amino acid residues, wherein only two amino acid residues of the N-terminal fragment are cysteine (Cys), wherein the residue at the C-terminal end of the region is Cys, and wherein the residue immediately preceding the C-terminal Cys residue of the region is a non-threonine substitution of the threonine (Thr) residue of position 6 of human CGRP;
Y1 is a central core region wherein at least one amino acid of the central core is arginine (Arg) or lysine (Lys) and the central core comprises an α-helix; and Z1 is a modified C-terminal fragment (i.e., region) of calcitonin gene-related peptide comprising from five to seven amino acid residues with a C-terminal amide, where at least one amino acid of the C-terminal fragment is phenylalanine (Phe), tyrosine (Tyr), proline (Pro) or hydroxyproline (Hyp). In some embodiments of the calcitonin gene-related peptide (CGRP) receptor antagonist for use, the CGRP receptor antagonist comprises a sequence set forth in one of SEQ ID NO: 1 (NH2-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 2 (NH2-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 3 (NH2-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 4 (NH2-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 5 (NH2-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 6 (NH2-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 7 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 8 (NH2-Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 9 (NH2-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 10 (NH2-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 11 (NH2-Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 12 (NH2-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 13 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Thr-Asn-Thr-Gly-Ser-Gly-Thr-Pro-NH2), SEQ ID NO: 14 (Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Val-Asp-Pro-Ser-Ser-Pro-His-Ser-Tyr-NH2), SEQ ID NO: 15 (Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH2), SEQ ID NO: 57 (NH2-Ala-Cys-Asp-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or SEQ ID NO: 58 (NH2-Ala-Cys-Asp-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or a pharmaceutically acceptable salt thereof. In some embodiments of the calcitonin gene-related peptide (CGRP) receptor antagonist for use, the CGRP receptor antagonist comprises a sequence selected from the group consisting of the sequences set forth in SEQ ID NO: 1, 2, 3, 4, 5, 6, 7, 8, 9, 10, 11, 12 and 13. In some embodiments of the calcitonin gene-related peptide (CGRP) receptor antagonist for use, the CGRP receptor antagonist is administered topically, dermally, intradermally, subcutaneously, via dermal infusion, via subcutaneous infusion, intraocularly, buccally, intravenously, nasally, via inhalation, intramuscularly, sublingually or orally. In some embodiments of the calcitonin gene-related peptide (CGRP) receptor antagonist for use, the CGRP receptor antagonist for use is in a pharmaceutical vehicle formulated for topical, dermal, intradermal, subcutaneous, dermal infusion, subcutaneous infusion, intraocular, buccal, intravenous, nasal, inhalation, intramuscular, sublingual or oral administration. In some embodiments of the calcitonin gene-related peptide (CGRP) receptor antagonist for use, the effective amount of calcitonin gene-related (CGRP) comprises an amount of about 50 µg, 60 µg, 70 µg, 80 µg, 90 µg, 100 µg, 200 µg, 300 µg, 400 µg, 500 µg, 600 µg, 700 µg, 800 µg, 900 µg, 1 mg, 5 mg, 10 mg, 40 mg, 50 mg, 100 mg, 200 mg, 300 mg, 400 mg, 500 mg, 600 mg, 700 mg, 800 mg, 900 mg or 1000 mg or any amount in between a range defined by any two aforementioned values. In some embodiments of the calcitonin gene-related peptide (CGRP) receptor antagonist for use, the calcitonin gene-related peptide (CGRP) receptor antagonist is administered at least once daily, once a week, twice a week, three times a week, or four times a week. In some embodiments of the calcitonin gene-related peptide (CGRP) receptor antagonist for use, the spontaneous nerve activity is due to a nerve injury or neurodegenerative disease. In some embodiments of the calcitonin gene-related peptide (CGRP) receptor antagonist for use, the nerve injury is from a physical injury, diabetes, cancer, diabetic neuropathy, head injury, seizures, infection, or ingestion of a pharmaceutical or drug, such as a chemotherapeutic. In some embodiments of the calcitonin gene-related peptide (CGRP) receptor antagonist for use, the neurodegenerative disease is amyotrophic lateral sclerosis, multiple sclerosis, Creutzfeld-Jakob disease, epilepsy, Parkinson's, Alzheimer's, glaucoma, cerebrovascular ischemia, motor neuron disease, dementia, diabetic neuropathy or Huntington's disease. In some embodiments of the calcitonin gene-related peptide (CGRP) receptor antagonist for use, the patient has been identified or selected to receive a drug for neurodegenerative diseases, neurovascular disorder or disease such as cancer. In some embodiments of the calcitonin gene-related peptide (CGRP) receptor antagonist for use, the nerve injury is from a pharmaceutical or drug, wherein the pharmaceutical or drug is a heart medication (i.e. almitrine), an anti-cancer drug, antibiotic (i.e. chlorampheticol, Cipro), anti-fungal, immunosuppressant drug (i.e. Cyclosporine), muscle relaxant (i.e. Hydrazaline), anti-seizure medications (i.e. Phenytoin), anti-viral, anti-HIV drug, anti-inflammatory, centrally-acting muscle relaxant, nootropica agent, apoptosis inhibitor, growth factor agonist, smooth muscle relaxantium, chloroquine, isoniazid, metronidazole, nitrofurantoin, thalidomide, etanercept, infliximab, leflunomide, dapsone, phenytoin, disulfiram, didanosine, stavudine, Kenalog-40, triamcinolone, Clinacort or antiparasitic. In some embodiments of the calcitonin gene-related peptide (CGRP) receptor antagonist for use, the drug is administered to said patient before, during or after administering the CGRP receptor antagonist. In some embodiments of the calcitonin gene-related peptide (CGRP) receptor antagonist for use, the CGRP receptor antagonist is used in combination with the drug. In some embodiments of the calcitonin gene-related peptide (CGRP) receptor antagonist for use, a level of nerve activity function is monitored or measured in said patient before, during or after administration of the effective amount of CGRP receptor antagonist. In some embodiments of the calcitonin gene-related peptide (CGRP) receptor antagonist for use, the nerves are C-Nociceptors or Group C nerve fibers. In some embodiments of the calcitonin gene-related peptide (CGRP) receptor antagonist for use, the calcitonin gene-related peptide (CGRP) receptor antagonist reduces pain associated with spontaneous nerve activity in the patient in need thereof. In some embodiments of the calcitonin gene-related peptide (CGRP) receptor antagonist for use, the CGRP receptor antagonist is administered within a pharmaceutically acceptable formulation.

In an eighth aspect, an effective amount of calcitonin gene-related peptide (CGRP) receptor antagonist or pharmaceutically acceptable salt thereof, for use in providing neuroprotection in a patient in need thereof, is provided. In some embodiments of the calcitonin gene-related peptide (CGRP) receptor antagonist for use, the CGRP receptor antagonist is a peptide comprising a structure of Formula I:

$$X1—Y1—Z1 \quad (I)$$

wherein:

X1 is a modified N-terminal fragment (i.e. region) of calcitonin gene-related peptide comprising from five to seven amino acid residues, wherein only two amino acid residues of the N-terminal fragment are cysteine (Cys), wherein the C-terminal residue of the fragment is Cys, and wherein the residue immediately preceding the C-terminal Cys residue of the region is a non-threonine substitution of a threonine (Thr) residue;

Y1 is a central core wherein at least one amino acid of the central core is arginine (Arg) or lysine (Lys) and the central core comprises an α-helix; and $Z^1$ is a modified C-terminal fragment (i.e. region) of calcitonin gene-related peptide comprising from five to seven amino acid residues with a C-terminal amide, where at least one amino acid of the C-terminal fragment is phenylalanine (Phe), tyrosine (Tyr), proline (Pro) or hydroxyproline (Hyp). In some embodiments of the calcitonin gene-related peptide (CGRP) receptor antagonist for use, the CGRP receptor antagonist comprises a sequence set forth in one of SEQ ID NO: 1 (NH2-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 2 (NH2-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 3 (NH2-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 4 (NH2-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 5 (NH2-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg- Thr-Asn-Val-Gly-Ser-Lys-Ala-Phe-NH2), SEQ ID NO: 6 (NH2-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 7 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 8 (NH2-Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 9 (NH2-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 10 (NH2-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 11 (NH2-Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 12 (NH2-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 13 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Thr-Asn-Thr-Gly-Ser-Gly-Thr-Pro-NH2), SEQ ID NO: 14 (Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Val-Asp-Pro-Ser-Ser-Pro-His-Ser-Tyr-NH2), SEQ ID NO: 15 (Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH2), SEQ ID NO: 57 (NH2-Ala-Cys-Asp-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or SEQ ID NO: 58 (NH2-Ala-Cys-Asp-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or a pharmaceutically acceptable salt thereof. In some embodiments of the calcitonin gene-related peptide (CGRP) receptor antagonist for use, the CGRP antagonist comprises a sequence selected from the group consisting of the sequences set forth in SEQ ID NO: 1, 2, 3, 4, 5, 6, 7, 8, 9, 10, 11, 12 and 13. In some embodiments of the calcitonin gene-related peptide (CGRP) receptor antagonist for use, the CGRP receptor antagonist is administered topically, dermally, intradermally, subcutaneously, via dermal infusion, via subcutaneous infusion, intraocularly, buccally, intravenously, nasally, via inhalation, intramuscularly, sublingually or orally. In some embodiments of the calcitonin gene-related peptide (CGRP) receptor antagonist for use, the CGRP receptor antagonist is in a pharmaceutical vehicle formulated for topical, dermal, intradermal, subcutaneous, dermal infusion, subcutaneous infusion, intraocular, buccal, intravenous, nasal, inhalation, intramuscular, sublingual or oral administration. In some embodiments of the calcitonin gene-related peptide (CGRP) receptor antagonist for use, the effective amount comprises an amount of about 50 µg, 60 µg, 70 µg, 80 µg, 90 µg, 100 µg, 200 µg, 300 µg, 400 µg, 500 µg, 600 µg, 700 µg, 800 µg, 900 µg, 1 mg, 5 mg, 10 mg, 40 mg, 50 mg, 100 mg, 200 mg, 300 mg, 400 mg, 500 mg, 600 mg, 700 mg, 800 mg, 900 mg or 1000 mg or any amount in between a range defined by any two aforementioned values. In some embodiments of the calcitonin gene-related peptide (CGRP) receptor antagonist for use, the calcitonin gene-related peptide (CGRP) receptor antagonist is administered at least once daily, once a week, twice a week, three times a week, or four times a week. In some embodiments of the calcitonin gene-related peptide (CGRP) receptor antagonist for use, the patient is suffering from a nerve injury, neurodegenerative disease or a disease such as cancer. In some embodiments of the calcitonin gene-related peptide (CGRP) receptor antagonist for use, the nerve injury is from a physical injury, diabetes, cancer, diabetic neuropathy, head injury, seizures, infection, or ingestion of a pharmaceutical or drug, such as a chemotherapeutic. In some embodiments of the calcitonin gene-related peptide (CGRP) receptor antagonist for use, the pharmaceutical or drug is associated with side effects related to neuronal dysfunction. In some embodiments of the calcitonin gene-related peptide (CGRP) receptor antagonist for use, the neurodegenerative disease is amyotrophic lateral sclerosis, multiple sclerosis, Creutzfeld-Jakob disease, epilepsy, Parkinson's, Alzheimer's, glaucoma, cerebrovascular ischemia, motor neuron disease, dementia, diabetic neuropathy, Huntington's disease, seizures or head injury. In some embodiments of the calcitonin gene-related peptide (CGRP) receptor antagonist for use, the patient has been identified or selected to receive neuroprotection treatment. In some embodiments of the calcitonin gene-related peptide (CGRP) receptor antagonist for use, a level of nerve activity function is monitored or measured in said patient before, during or after administration of the effective amount of CGRP receptor antagonist. In some embodiments of the calcitonin gene-related peptide (CGRP) receptor antagonist for use, the patient has been identified or selected to receive a drug. In some embodiments of the calcitonin gene-related peptide (CGRP) receptor antagonist for use, the drug is associated with side effects related to neuronal dysfunction. In some embodiments of the calcitonin gene-related peptide (CGRP) receptor antagonist for use, the drug associated with neuronal dysfunction is a heart medication (i.e. almitrine), an anti-cancer drug, antibiotic (i.e. chlorampheticol, Cipro), anti-fungal, immunosuppressant drug (i.e. Cyclosporine), muscle relaxant (i.e. Hydrazaline), anti-seizure medications (i.e. Phenytoin), anti-viral, anti-HIV drug, anti-inflammatory, centrally-acting muscle relaxant, nootropica agent, apoptosis inhibitor, growth factor agonist, smooth muscle relaxantium, chloroquine, isoniazid, metronidazole, nitrofurantoin, thalidomide, etanercept, infliximab, leflunomide, dapsone, phenytoin, disulfiram, didanosine, stavudine, Kenalog-40, triamcinolone, Clinacort or antiparasitic. In some embodiments of the calcitonin gene-related peptide (CGRP) receptor antagonist for use, the CGRP receptor antagonist is administered within a pharmaceutically acceptable formulation. In some embodiments of the calcitonin gene-related peptide (CGRP) receptor antagonist for use, the drug is introduced, provided or administered to said patient before, during or after administering the CGRP receptor antagonist. In some embodiments of the calcitonin gene-related peptide (CGRP) receptor antagonist for use, the CGRP receptor antagonist is used in combination with the drug.

In a ninth aspect, an effective amount of calcitonin gene-related peptide (CGRP) receptor antagonist or pharmaceutically acceptable salt thereof, for use in treating neuritis in a patient in need thereof is provided. In some embodiments of the calcitonin gene-related peptide (CGRP) receptor antagonist for use, the CGRP receptor antagonist or pharmaceutically acceptable salt thereof comprises a structure of Formula I:

X1—Y1—Z1    (I)

wherein:
- X1 is a modified N-terminal fragment (i.e. region) of calcitonin gene-related peptide comprising from five to seven amino acid residues, wherein only two amino acid residues of the N-terminal fragment are cysteine (Cys), wherein the amino acid residue at the C-terminal end of the fragment (region) is Cys, and wherein the residue immediately preceding the C-terminal Cys residue is a non-threonine substitution of the threonine (Thr) residue found at position 6 of human CGRP;
- Y1 is a central core region wherein at least one amino acid of the central core is arginine (Arg) or lysine (Lys) and the central core comprises an α-helix; and
- $Z^1$ is a modified C-terminal fragment (i.e. region) of calcitonin gene-related peptide comprising from five to seven amino acid residues with a C-terminal amide, where at least one amino acid of the C-terminal fragment is phenylalanine (Phe), tyrosine (Tyr), proline (Pro) or hydroxyproline (Hyp). In some embodiments of the calcitonin gene-related peptide (CGRP) receptor antagonist for use, the CGRP receptor antagonist comprises a sequence set forth in one of SEQ ID NO: 1 (NH2-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 2 (NH2-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 3 (NH2-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 4 (NH2-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 5 (NH2-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 6 (NH2-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 7 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 8 (NH2-Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 9 (NH2-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 10 (NH2-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 11 (NH2-Ala-Cys-Asn-Leu-Ser-Val-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 12 (NH2-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 13 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Thr-Asn-Thr-Gly-Ser-Gly-Thr-Pro-NH2), SEQ ID NO: 14 (Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Val-Asp-Pro-Ser-Ser-Pro-His-Ser-Tyr-NH2), SEQ ID NO: 15 (Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH2), SEQ ID NO: 57 (NH2-Ala-Cys-Asp-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or SEQ ID NO: 58 (NH2-Ala-Cys-Asp-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or a pharmaceutically acceptable salt thereof. In some embodiments of the calcitonin gene-related peptide (CGRP) receptor antagonist for use, the CGRP antagonist comprises a sequence selected from the group consisting of the sequences set forth in SEQ ID NO: 1, 2, 3, 4, 5, 6, 7, 8, 9, 10, 11, 12 and 13. In some embodiments of the calcitonin gene-related peptide (CGRP) receptor antagonist for use, the CGRP receptor antagonist is administered topically, dermally, intradermally, subcutaneously, via dermal infusion, via subcutaneous infusion, intraocularly, buccally, intravenously, nasally, via inhalation, intramuscularly, sublingually or orally. In some embodiments of the calcitonin gene-related peptide (CGRP) receptor antagonist for use, the CGRP receptor antagonist is in a pharmaceutical vehicle formulated for topical, dermal, intradermal, subcutaneous, dermal infusion, subcutaneous infusion, intraocular, buccal, intravenous, nasal, inhalation, intramuscular, sublingual or oral administration. In some embodiments of the calcitonin gene-related peptide (CGRP) receptor antagonist for use, the effective amount comprises an amount of 50 µg, 60 µg, 70 µg, 80 µg, 90 µg, 100 µg, 200 µg, 300 µg, 400 µg, 500 µg, 600 µg, 700 µg, 800 µg, 900 µg, 1 mg, 5 mg, 10 mg, 40 mg, 50 mg, 100 mg, 200 mg, 300 mg, 400 mg, 500 mg, 600 mg, 700 mg, 800 mg, 900 mg or 1000 mg or any amount in between a range defined by any two aforementioned values. In some embodiments of the calcitonin gene-related peptide (CGRP) receptor antagonist for use, the calcitonin gene-related peptide (CGRP) receptor antagonist is administered at least once daily, once a week, twice a week, three times a week, or four times a week. In some embodiments of the calcitonin gene-related peptide (CGRP) receptor antagonist for use, a level of nerve activity function is monitored or measured in said patient before, during or after administration of the effective amount of CGRP receptor antagonist. In some embodiments of the calcitonin gene-related peptide (CGRP) receptor antagonist for use, the patient has been identified or selected to receive a drug. In some embodiments of the calcitonin gene-related peptide (CGRP) receptor antagonist for use, the drug can cause neuronal dysfunction. In some embodiments of the calcitonin gene-related peptide (CGRP) receptor antagonist for use, the drug causing neuronal dysfunction is a heart medication (i.e. almitrine), an anti-cancer drug, antibiotic (i.e. chlorampheticol, Cipro), anti-fungal, immunosuppressant drug (i.e. Cyclosporine), muscle relaxant (i.e. Hydrazaline), anti-seizure medications (i.e. Phenytoin), anti-viral, anti-HIV drug, anti-inflammatory, centrally-acting muscle relaxant, nootropica agent, apoptosis inhibitor, growth factor agonist, smooth muscle relaxantium, chloroquine, isoniazid, metronidazole, nitrofurantoin, thalidomide, etanercept, infliximab, leflunomide, dapsone, phenytoin, disulfiram, didanosine, stavudine, Kenalog-40, triamcinolone, Clinacort or antiparasitic. In some embodiments of the calcitonin gene-related peptide (CGRP) receptor antagonist for use, the neuritis is from a physical injury, vascular injury, toxin aging, a genetic disorder, infection (viral or bacterial), diphtheria, herpes zoster (shingles), leprosy, Lyme disease, chemical injury such as chemotherapy, radiation therapy, alcoholism, autoimmune disease, multiple sclerosis, Guillain-Barre syndrome, beriberi (vitamin B1 deficiency), cancer, Celiac disease, diabetes (Diabetic neuropathy), hypothyroidism, porphyria, vitamin B12 deficiency, vitamin B6 excess, brachial neuritis, cranial neuritis, Bell's palsy, optic neuritis or vestibular neuritis. In some embodiments of the calcitonin gene-related peptide (CGRP) receptor antagonist for use, the CGRP receptor antagonist is administered within a pharmaceutically acceptable formulation. In some embodiments of the calcitonin gene-related peptide (CGRP) receptor antagonist for use, the drug is administered before, during or after administering the CGRP receptor antagonist.

In a tenth aspect, an effective amount of calcitonin gene-related peptide (CGRP) receptor antagonist or pharmaceutically acceptable salt thereof for use in treating glaucoma in a patient, provided. In some embodiments of the calcitonin gene-related peptide (CGRP) receptor antagonist for use, the CGRP receptor antagonist is a peptide or pharmaceutically acceptable salt thereof comprising a structure of Formula I:

$$X1—Y1—Z1 \qquad (I)$$

wherein:
X1 is a modified N-terminal fragment (i.e., region) of calcitonin gene-related peptide comprising from five to seven amino acid residues, wherein only two amino acid residues of the N-terminal fragment are cysteine (Cys), wherein the residue at the C-terminal end of the fragment is Cys, and wherein the residue immediately preceding the C-terminal Cys residue of the region is a non-threonine substitution of the threonine (Thr) residue of position 6 of human CGRP;
Y1 is a central core region wherein at least one amino acid of the central core is arginine (Arg) or lysine (Lys) and the central core comprises an α-helix; and
$Z^1$ is a modified C-terminal fragment (i.e. region) of calcitonin gene-related peptide comprising from five to seven amino acid residues with a C-terminal amide, where at least one amino acid of the C-terminal region is phenylalanine (Phe), tyrosine (Tyr), proline (Pro) or hydroxyproline (Hyp). In some embodiments of the calcitonin gene-related peptide (CGRP) receptor antagonist for use, the CGRP receptor antagonist comprises a sequence set forth in one of SEQ ID NO: 1 (NH2-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 2 (NH2-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 3 (NH2-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 4 (NH2-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 5 (NH2-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 6 (NH2-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 7 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 8 (NH2-Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 9 (NH2-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 10 (NH2-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 11 (NH2-Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 12 (NH2-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 13 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Thr-Asn-Thr-Gly-Ser-Gly-Thr-Pro-NH2), SEQ ID NO: 14 (Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Val-Asp-Pro-Ser-Ser-Pro-His-Ser-Tyr-NH2), SEQ ID NO: 15 (Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH2), SEQ ID NO: 57 (NH2-Ala-Cys-Asp-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or SEQ ID NO: 58 (NH2-Ala-Cys-Asp-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or a pharmaceutically acceptable salt thereof. In some embodiments of the calcitonin gene-related peptide (CGRP) receptor antagonist for use, the CGRP antagonist comprises a sequence selected from the group consisting of the sequences set forth in SEQ ID NO: 1, 2, 3, 4, 5, 6, 7, 8, 9, 10, 11, 12 and 13. In some embodiments of the calcitonin gene-related peptide (CGRP) receptor antagonist for use, the CGRP receptor antagonist is administered topically, dermally, intradermally, subcutaneously, via dermal infusion, via subcutaneous infusion, intraocularly, buccally, intravenously, nasally via inhalation, intramuscularly, sublingually or orally. In some embodiments of the calcitonin gene-related peptide (CGRP) receptor antagonist for use, the CGRP receptor antagonist is in a pharmaceutical vehicle formulated for topical, dermal, intradermal, subcutaneous, dermal infusion, subcutaneous infusion, intraocular, buccal, intravenous, nasal, inhalation, intramuscular, sublingual or oral administration. In some embodiments of the calcitonin gene-related peptide (CGRP) receptor antagonist for use, the effective amount comprises an amount of about 50 µg, 60 µg, 70 µg, 80 µg, 90 µg, 100 µg, 200 µg, 300 µg, 400 µg, 500 µg, 600 µg, 700 µg, 800 µg, 900 µg, 1 mg, 10 mg, 20 mg, 30 mg, 40 mg, 50 mg, 100 mg, 200 mg, 300 mg, 400 mg, 500 mg, 600 mg, 700 mg, 800 mg, 900 mg or 1000 mg or any amount in between a range defined by any two aforementioned values. In some embodiments of the calcitonin gene-related peptide (CGRP) receptor antagonist for use, the calcitonin gene-related peptide (CGRP) receptor antagonist is administered at least four times a day, three times a day, two times a day, or once a day. In some embodiments of the calcitonin gene-related peptide (CGRP) receptor antagonist for use, the patient has diabetes. In some embodiments of the calcitonin gene-related peptide (CGRP) receptor antagonist for use, the patient has been identified or selected to receive a drug for glaucoma. In some embodiments of the calcitonin gene-related peptide (CGRP) receptor antagonist for use, the drug is associated with nerve or central nervous system damage or neuronal dysfunction. In some embodiments of the calcitonin gene-related peptide (CGRP) receptor antagonist for use, the drug is a beta blocker. In some embodiments of the calcitonin gene-related peptide (CGRP) receptor antagonist for use, the CGRP receptor antagonist is administered within a pharmaceutically acceptable formulation. In some embodiments of the calcitonin gene-related peptide (CGRP) receptor antagonist for use, the drug is introduced, provided or administered to said patient before, during or after administering the CGRP receptor antagonist. In some embodiments of the calcitonin gene-related peptide (CGRP) receptor antagonist for use, the CGRP receptor antagonist is used in combination with the drug.

In an eleventh aspect, an effective amount of calcitonin gene-related peptide (CGRP) receptor antagonist or pharmaceutically acceptable salt thereof for use in reducing LDL in a patient in need thereof, is provided. In some embodiments of the calcitonin gene-related peptide (CGRP) receptor antagonist for use, the CGRP receptor antagonist is a peptide or pharmaceutically acceptable salt thereof comprising a structure of Formula I:

$$X1—Y1—Z1 \qquad (I)$$

wherein:
X1 is a modified N-terminal fragment (i.e., region) of calcitonin gene-related peptide comprising from five to seven amino acid residues, wherein only two amino acid residues of the N-terminal fragment are cysteine (Cys), wherein the residue at the C-terminal end of the region is Cys, and wherein the residue immediately preceding the C-terminal Cys residue of the region is a non-threonine substitution of the threonine (Thr) residue of position 6 of human GCRP;
Y1 is a central core region wherein at least one amino acid of the central core is arginine (Arg) or lysine (Lys) and the central core comprises an α-helix; and
Z1 is a modified C-terminal fragment (i.e., region) of calcitonin gene-related peptide comprising from five to seven amino acid residues with a C-terminal amide, where at least one amino acid of the C-terminal fragment is phenylalanine (Phe), tyrosine (Tyr), proline (Pro) or hydroxyproline (Hyp). In some embodiments of the calcitonin gene-related peptide (CGRP) receptor antagonist for use, the CGRP receptor antagonist comprises a sequence set forth in one of SEQ ID NO: 1 (NH2-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 2 (NH2-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 3 (NH2-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 4 (NH2-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 5 (NH2-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 6 (NH2-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 7 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 8 (NH2-Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 9 (NH2-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 10 (NH2-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 11 (NH2-Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 12 (NH2-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 13 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Thr-Asn-Thr-Gly-Ser-Gly-Thr-Pro-NH2), SEQ ID NO: 14 (Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Val-Asp-Pro-Ser-Ser-Pro-His-Ser-Tyr-NH2), SEQ ID NO: 15 (Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH2), SEQ ID NO: 57 (NH2-Ala-Cys-Asp-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or SEQ ID NO: 58 (NH2-Ala-Cys-Asp-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or a pharmaceutically acceptable salt thereof. In some embodiments of the calcitonin gene-related peptide (CGRP) receptor antagonist for use, the CGRP antagonist comprises a sequence selected from the group consisting of the sequences set forth in SEQ ID NO: 1, 2, 3, 4, 5, 6, 7, 8, 9, 10, 11, 12 and 13. In some embodiments of the calcitonin gene-related peptide (CGRP) receptor antagonist for use, the patient is suffering from high LDL concentration in the blood. In some embodiments of the calcitonin gene-related peptide (CGRP) receptor antagonist for use, a level or amount of LDL in said patient is monitored or measured before, during, or after administration of the effective amount of CGRP receptor antagonist. In some embodiments of the calcitonin gene-related peptide (CGRP) receptor antagonist for use, the patient is a male. In some embodiments of the calcitonin gene-related peptide (CGRP) receptor antagonist for use, the patient has familial hypercholesterolemia. In some embodiments of the calcitonin gene-related peptide (CGRP) receptor antagonist for use, the CGRP receptor antagonist is in a pharmaceutical vehicle formulated for topical, dermal, intradermal, subcutaneous, dermal infusion, subcutaneous infusion, intraocular, buccal, intravenous, nasal, inhalation, intramuscular, sublingual or oral administration. In some embodiments of the calcitonin gene-related peptide (CGRP) receptor antagonist for use, the effective amount comprises an amount of about 50 µg, 60 µg, 70 µg, 80 µg, 90 µg, 100 µg, 200 µg, 300 µg, 400 µg, 500 µg, 600 µg, 700 µg, 800 µg, 900 µg, 1 mg, 10 mg, 20 mg, 30 mg, 40 mg, 50 mg, 100 mg, 200 mg, 300 mg, 400 mg, 500 mg, 600 mg, 700 mg, 800 mg, 900 mg or 1000 mg or any amount in between a range defined by any two aforementioned values. In some embodiments of the calcitonin gene-related peptide (CGRP) receptor antagonist for use, the calcitonin gene-related peptide (CGRP) receptor antagonist is administered at least four times a day, three times a day, two times a day, or once a day.

In a twelfth aspect, an effective calcitonin gene-related peptide (CGRP) receptor antagonist or a pharmaceutically acceptable salt thereof for use in protecting a patient from nerve damage or nerve inflammation, is provided. In some embodiments of the calcitonin gene-related peptide (CGRP) receptor antagonist for use, the patient suffers from a post ischemic event. In some embodiments of the calcitonin gene-related peptide (CGRP) receptor antagonist for use, the CGRP receptor antagonist is a peptide or a pharmaceutically acceptable salt thereof comprising a structure of Formula I:

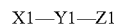

wherein:
X1 is a modified N-terminal fragment (i.e., region) of calcitonin gene-related peptide comprising from five to seven amino acid residues, wherein only two amino acid residues of the N-terminal fragment are cysteine (Cys), wherein the residue at the C-terminal end of the region is Cys, and wherein the residue immediately preceding the C-terminal Cys residue of the region is a non-threonine substitution of the threonine (Thr) residue of position 6 of human CGRP;
Y1 is a central core region wherein at least one amino acid of the central core is arginine (Arg) or lysine (Lys) and the central core comprises an α-helix; and
Z1 is a modified C-terminal fragment (i.e., region) of calcitonin gene-related peptide comprising from five to seven amino acid residues with a C-terminal amide, where at least one amino acid of the Z1 region is phenylalanine (Phe), tyrosine (Tyr), proline (Pro) or hydroxyproline (Hyp). In some embodiments of the calcitonin gene-related peptide (CGRP) receptor antagonist for use, the CGRP receptor antagonist comprises a sequence set forth in one of SEQ ID NO: 1 (NH2-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 2 (NH2-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 3 (NH2-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 4 (NH2-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 5 (NH2-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 6 (NH2-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 7 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 8 (NH2-Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 9 (NH2-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 10 (NH2-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 11 (NH2-Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 12 (NH2-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2), SEQ ID NO: 13 (NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Thr-Asn-Thr-Gly-Ser-Gly-Thr-Pro-NH2), SEQ ID NO: 14 (Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Val-Asp-Pro-Ser-Ser-Pro-His-Ser-Tyr-NH2), SEQ ID NO: 15 (Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH2), SEQ ID NO: 57 (NH2-Ala-Cys-Asp-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or SEQ ID NO: 58 (NH2-Ala-Cys-Asp-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2) or a pharmaceutically acceptable salt thereof. In some embodiments of the calcitonin gene-related peptide (CGRP) receptor antagonist for use, the CGRP antagonist comprises a sequence selected from the group consisting of the sequences set forth in SEQ ID NO: 1, 2, 3, 4, 5, 6, 7, 8, 9, 10, 11, 12 and 13. In some embodiments of the calcitonin gene-related peptide (CGRP) receptor antagonist for use, the CGRP receptor antagonist is in a pharmaceutical vehicle formulated for topical, dermal, intradermal, subcutaneous, dermal infusion, subcutaneous infusion, intraocular, buccal, intravenous, nasal, inhalation, intramuscular, sublingual or oral administration. In some embodiments of the calcitonin gene-related peptide (CGRP) receptor antagonist for use, the calcitonin gene-related peptide (CGRP) receptor antagonist is administered at least four times a day, three times a day, two times a day, or once a day. In some embodiments of the calcitonin gene-related peptide (CGRP) receptor antagonist for use, the effective amount comprises an amount of about 50 µg, 60 µg, 70 µg, 80 µg, 90 µg, 100 µg, 200 µg, 300 µg, 400 µg, 500 µg, 600 µg, 700 µg, 800 µg, 900 µg, 1 mg, 10 mg, 20 mg, 30 mg, 40 mg, 50 mg, 100 mg, 200 mg, 300 mg, 400 mg, 500 mg, 600 mg, 700 mg, 800 mg, 900 mg or 1000 mg or any amount in between a range defined by any two aforementioned values.

BRIEF DESCRIPTION OF THE DRAWINGS

FIGS. 2A and 2B: Comparison of two measures of spontaneous activity, SLI/10 min (FIG. 2A) and TI (%) (FIG. 2B) obtained 10 min before and 10 min after the CGRP receptor antagonist administration. No significant differences were observed (paired t-test).

FIG. 4A shows that the number of Brn3a positive profiles significantly decreased by 20.3% in the lasered eyes from the vehicle group as compared to contralateral control eyes (paired sample t-test, P=0.042). FIG. 4B shows that the number of Brn3a positive cells increased by 3.0% (P=0.43) in the CGRP antagonist group (SEQ ID NO: 1; NH2-ACDTAACVL-GRLSQELHRLQTYPRTNVGSKAF-NH2).

FIGS. 5A (control) and 5B CGRP receptor antagonist (SEQ ID NO: 1; NH2-ACDTAACVL-GRLSQELHRLQTYPRTNVGSKAF-NH2)) show that the total number of optic nerve axons did not differ significantly between lasered and contralateral control eyes in any of the treatment groups, although the vehicle treatment group showed the highest decrease in the total number of axons amongst all treatment groups and the CGRP antagonist (SEQ ID NO: 1; NH2-ACDTAACVLGRLSQELHRLQTY-PRTNVGSKAF-NH2) group showed the smallest decrease in the total number of axons (paired sample t-test, P>0.05 in all groups).

DEFINITIONS

Figure 1:
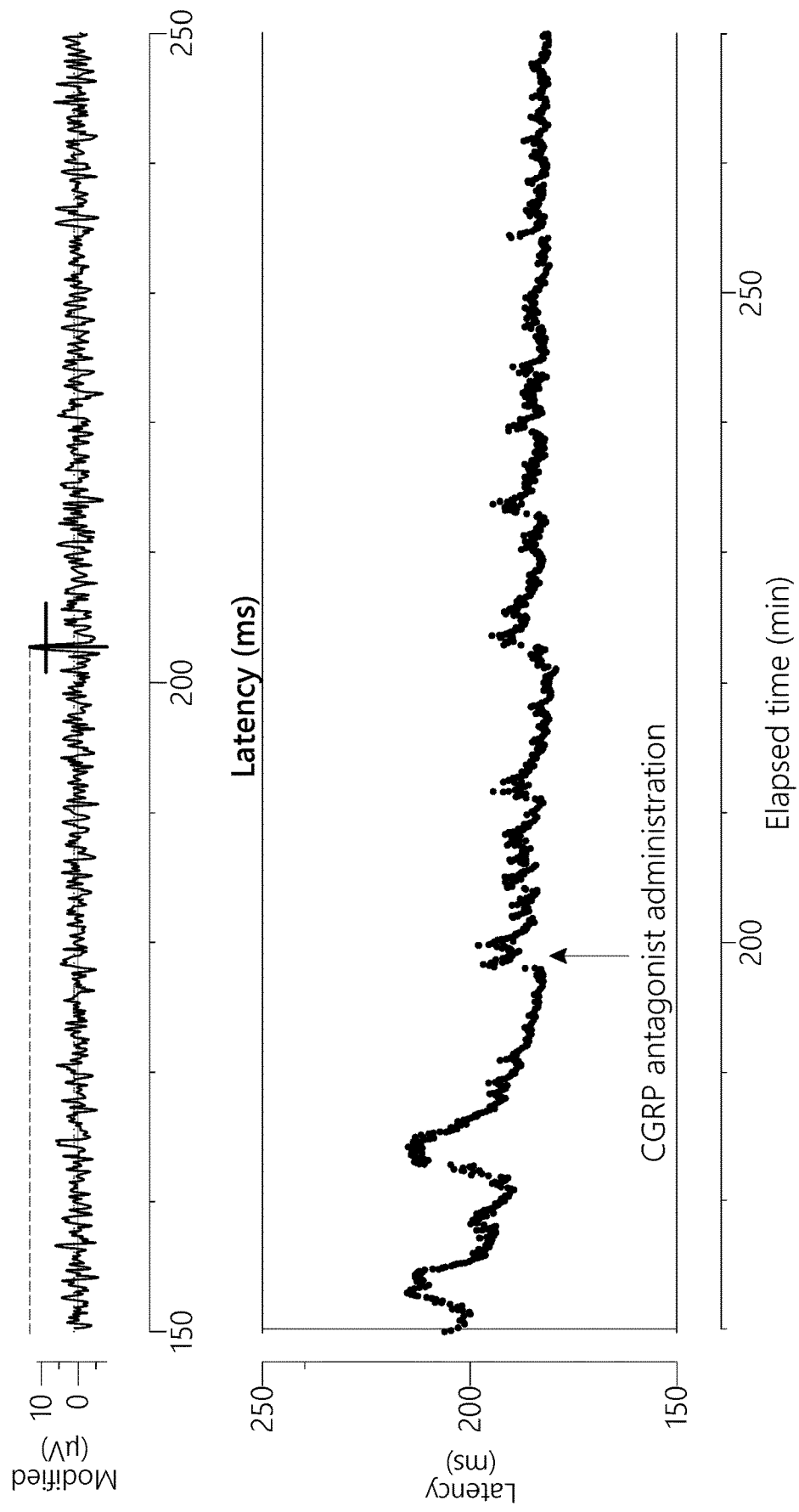
FIG. 1 shows an example of a spontaneously active C-nociceptor before and after CGRP antagonist (SEQ ID NO: 1; NH2-ACDTAACVLGRLSQELHRLQTY-PRTNVGSKAF-NH2) administration. Top panel: individual sweep of the recorded electrical activity in response to stimulation of the receptive field. Bottom panel: latency raster plot showing the profile of a spontaneous C nociceptor. The arrow indicates moment of administration of the CGRP antagonist compound.

Unless defined otherwise, all technical and scientific terms used herein have the same meaning as commonly understood by one of ordinary skill in the art to which the invention pertains.

"About" as used herein when referring to a measurable value is meant to encompass variations of 20% or 10%, more preferably ±5%, even more preferably ±1%, and still more preferably ±0.1% from the specified value.

As used herein, "antagonist" refers to a biologically active ligand which binds to a complementary biologically active receptor and inhibits the physiological response of the receptor. By way of example, as used herein, a "CGRP receptor antagonist" and "CGRP antagonist," refers to a ligand that binds to a CGRP receptor and inhibits the physiological response of that receptor.

As used herein, "agonist" refers to a biologically active ligand which binds to its complementary biologically active receptor and activates the latter either to cause a biological response in the receptor or to enhance preexisting biological activity of the receptor.

As used herein, "pharmaceutically acceptable salt" refers to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the modified calcitonin gene-related peptide antagonists disclosed herein with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like. Thus, the term refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. For a description of pharmaceutically acceptable salts as prodrugs, see Bundgaard et al., 1985.

"Percent (%) amino acid sequence identity" with respect to the sequences identified herein is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, % amino acid sequence identity values generated using the WU-BLAST-2 computer program [Altschul et al., Methods in Enzymology, 266:460-480 (1996)] uses several search parameters, most of which are set to the default values. Those that are not set to default values (i.e., the adjustable parameters) are set with the following values: overlap span=1, overlap fraction=0.125, word threshold (T)=11 and scoring matrix=BLOSUM62. A % amino acid sequence identity value is determined by dividing (a) the number of matching identical amino acid residues between the each or all of the polypeptide amino acid sequence of the reference chimeric receptor sequence provided in Table 2 and the comparison amino acid sequence of interest as determined by WU-BLAST-2 by (b) the total number of amino acid residues of the polypeptide of interest. In some alternatives, the percent sequence identity of amino acids or nucleic acids are determined by computer software.

As used herein, "spontaneous nerve activity" or "spontaneous activity of nerves" refers to the neural oscillation or rhythmic or repetitive neural activity in the nervous system. This oscillation can be generated in many ways by individual neurons or by the interaction between neurons. These neural oscillations can play an important role in neurological disorders such as during seizure activity in epilepsy and in the tremors in patients suffering from Parkinson's disease, for example. Epilepsy is a common chronic neurological disorder characterized by seizures. A tremor, as described herein, can be an involuntary, somewhat rhythmic muscle contraction and relaxation involving to-and-fro movements of one or more body parts. Most common tremors can include tremors of the hands, arms, eyes, face, head, vocal cords, trunk, and legs. Spontaneous nerve activity can also occur in C-fibers after partial damage to a nerve. In some embodiments, a method of reducing spontaneous activity in nerves in a patient following nerve injury is provided. The method comprises administering to the patient an effective amount of CGRP receptor antagonist. In some embodiments, the CGRP receptor antagonist is a peptide antagonist. In some embodiments the peptide antagonist comprises a sequence set forth in any of SEQ ID NOS: 1-15, 57 and 58. As described in an exemplary embodiment herein, the peptide antagonist comprising the sequence set forth in SEQ ID NO: 1 was used in a rat model having pathological spontaneous activity in C-nociceptors and C nerve fibers.

As used herein, "neurodegenerative disease" is any disease of a group of hereditary or sporadic conditions characterized by progressive dysfunction, degeneration and death of specific populations of neurons which are often synaptically interconnected. As used herein, "neurodegeneration" refers to the progressive loss of structure or function of neurons and can include the death of neurons. Neurodegeneration can be caused by neurodegenerative nerve disease, which can affect the body's activities such as balance, movement, talking, breathing, vision and heart function, for example. Examples for causes of neurodegeneration can include but is not limited to genetics, predisposition to medical conditions, alcoholism, tumor stroke, toxins, chemicals and viruses. In some cases the cause is unknown. Degenerative nerve diseases, or neurodegenerative diseases can include Alzheimer's disease, Amyotrophic lateral sclerosis, Friedreich's ataxia, Huntington's disease, Lewy body disease, Parkinson's disease, Spinal muscular atrophy, diabetic neuropathy and glaucoma, for example. In some embodiments provided herein, a method for treating, preventing or ameliorating the effects of neurodegeneration is provided. In some embodiments, the cause of neurodegeneration can be from genetics, predisposition to medical conditions, alcoholism, tumor, stroke, toxins, chemicals and viruses.

As used herein, "neurovascular disorder" or "neuromuscular disease" encompasses many diseases and ailments that can impair the functioning of the muscles, either directly, being pathologies of the voluntary muscle, or indirectly, being pathologies of nerves or neuromuscular junctions. Without being limiting, neurovascular disorders can include muscular weakness, rigidity, loss of muscular control, myoclonus (twitching, spasming), and myalgia (muscle pains).

As used herein, the term "neuritis" or "nerve injury" can include injury to the peripheral nerves such as laceration, focal contusion, stretch/traction injury, compression, drug injection injury, drugs, chemotherapeutic, neurovascular disorder, electrical injury, brachial plexus injury, foot drop injury, injury to the peroneal nerve and sciatic nerve, meralgia parasthetic (injury to the lateral femoral cutaneous nerve and femoral nerve, spinal accessory nerve injury (injury to the spinal accessory nerve and cranial nerve) and traumatic nerve injury. In some embodiments described herein, a method is provided for treating a patient suffering from a nerve injury. In some embodiments, the nerve injury is from a laceration, focal contusion, stretch/traction injury, compression, drug injection injury, electrical injury, brachial plexus injury, foot drop injury, injury to the peroneal nerve and sciatic nerve, Meralgia parasthetic (injury to the lateral femoral cutaneous nerve and femoral nerve or spinal accessory nerve injury (injury to the spinal accessory nerve and cranial nerve). Nerve injury can also lead to neurodegeneration. Treatments for nerve injury and neurodegenerative diseases can include but is not limited to a cell cycle inhibitor, a neuroprotectant, a nootropic agent, anticonvulsant agent, anxiolytic drug, antipsychotic drug, an analgesic, vasoprotectant, anti-amyloidogenic, immunomodulatory, anti-inflammatory, anti-parkinsonian, immunosuppressant, vasodilatory agent, immunostimulant, vasoprotectant, metabolic modulator, antihypertensive, centrally-acting muscle relaxant, nootropica agent, apoptosis inhibitor, growth factor agonist, smooth muscle relaxantium, neurotrophic agent, metabolic activator, ionotropic glutamate receptor antagonist, antihypertensive agent, antihypercholesterolemic agent, anti-amyloidogenic agent, anxiolytic; imaging agent; BDZ agonist, Class IV antiarrhythmic agent, TRH agonist and a cardioprotectant. Drugs for neuritis can include but is not limited to interferon beta-la, interferon beta-1b, Kenalog-40, triamcinolone or Clinacort. In some embodiments, neuritis can lead to spontaneous nerve activity.

The term "neuroprotection," as used herein refers to the preservation of neuronal structure and/or function. During a neurodegenerative insult the relative preservation of neuronal integrity implies a reduction in the rate of neuronal loss over time. As such developing methods to prevent further damage to the nerves have been explored. For example, increased levels of oxidative stress can be caused in part by neuroinflammation which can further lead to more damage by oxidative stress. Without being limiting, antioxidants such as acetylcysteine, cocin, fish oil, and resveratrol have been tested to investigate their role in neuroprotection. In some embodiments described herein, a method of providing neuroprotection in a patient in need thereof is provided. The method comprises administering to the patient an effective amount of CGRP receptor antagonist.

Some pharmaceuticals, such as chemotherapy drugs, can affect the cells of the nervous system by neurotoxicity or by neuropathy. Chemotherapy drugs can affect or damage the central nervous system, the peripheral nervous system and part of the peripheral nervous system called the cranial nerves. In some embodiments, a method of treating a patient suffering from nerve damage is provided. In some embodiments, nerve damage is caused by pharmaceuticals such as chemotherapeutics. In some embodiments, the chemotherapeutics comprises cis-platinum chemotherapy or 5-Fluorouracil (5-FU) chemotherapy. Cis-platinum chemotherapy can include, but is not limited to the use of cisplatin, cisplatinum, platamin, neoplatin, cismaplat or cis-diamminedichloridoplatinum(III). The use of these types of chemotherapeutics can cause neurotoxicity, including but not limited to visual perception and hearing disorders.

The term "C-Nociceptors" as used herein, are sensory nerve cells that respond to damaging or potentially damaging stimuli by sending signals to the spinal cord and brain. This process is called nociception, and can cause the perception of pain in sentient beings. Nociceptors are sensory neurons that are found in any area of the body that can sense noxious stimuli either externally or internally. Without being limiting, they can be found in tissues such as skin (cutaneous nociceptors), cornea and mucosa, for example. Internal nociceptors are in a variety of organs, such as the muscle, joint, bladder, gut and continuing along the digestive tract. The cell bodies of these neurons are located in either the dorsal root ganglia or the trigeminal ganglia. The trigeminal ganglia are specialized nerves for the face, whereas the dorsal root ganglia associate with the rest of the body. In some embodiments described herein, a method of treating a nerve injury is provided, wherein the method comprises administering to the patient an effective amount of CGRP receptor antagonist. In some embodiments, the nerve injury is at a C-nociceptor or in group C nerve fibers.

The term "Group C nerve fibers" as used herein, are one of three classes of nerve fibers in the central nervous system and peripheral nervous system. The C group fibers are unmyelinated and have a small diameter and low conduction velocity. They include Postganglionic fibers in the autonomic nervous system (ANS), and nerve fibers at the dorsal roots (IV fiber). These fibers carry sensory information. A Damage or injury to these nerve fibers causes neuropathic pain.

The term "electromyoneurography" (EMNG), as used herein, is a method to test the level of nerve activity. EMNG is the combined use of electromyography and electroneurography for the measurement of peripheral nerve's conduction velocity upon stimulation alongside electrical recording of muscular activity. In some embodiments described herein, a method of treating a nerve injury in a patient is provided, wherein the patient is administered an effective amount of a CGRP antagonist peptide. In some embodiments, the method further comprises monitoring or measuring a level of nerve activity function in said patient before, during or after administration of the effective amount of CGRP receptor antagonist. In some embodiments, the monitoring is performed by electromyoneurography.

The term "nerve conduction velocity test" (NCV), as used herein is a test commonly used to evaluate the function, and the ability of the electrical conduction of the motor and sensory nerves of the human body. Nerve conduction velocity (NCV) is a common measurement made during this test. A nerve conduction velocity test measures how quickly electrical impulses move along a nerve. In some embodiments described herein, a method of treating a nerve injury in a patient is provided, wherein the patient is administered an effective amount of a CGRP antagonist peptide. In some embodiments, the method further comprises monitoring or measuring a level of nerve activity function in said patient before, during or after administration of the effective amount of CGRP receptor antagonist. In some embodiments, the monitoring is performed by nerve conduction velocity test.

The term "diabetes" as used herein, is a group of metabolic diseases in which there are high blood sugar levels over a prolonged period. "Diabetic neuropathy" as described herein refers to a type of nerve damage that can occur when one has diabetes. High blood sugar can injure nerve fibers throughout the patient's body, but diabetic neuropathies can often damages nerves in the legs and feet, for example. In some embodiments, a method of treating a patient suffering from neuropathy is provided, wherein the patient is administered an effective amount of a CGRP antagonist. In some embodiments, the neuropathy is diabetic neuropathy.

Diabetic neuropathy is a common serious complication of diabetes. Yet one can often prevent diabetic neuropathy or slow its progress with tight blood sugar control and a healthy lifestyle. Depending on the affected nerves, symptoms of diabetic neuropathy can range from pain and numbness in the patient's extremities to problems with the patient's digestive system, urinary tract, blood vessels and heart. For some people, these symptoms are mild; for others, diabetic neuropathy can be painful, disabling and even fatal. In some cases, medication is required to control the pain stemming from diabetic neuropathy.

The term "glaucoma" as described herein, is a group of eye diseases which result in damage to the optic nerve and vision loss. The risk factors for glaucoma include but are not limited to increased pressure in the eye, a family history of the condition, migraines, high blood pressure, diabetes and obesity. For eye pressures a value equal to or greater than 21 mmHg or 2.8 kPa is often used with higher pressures leading to a greater risk. Treatment for glaucoma can include but is not limited to beta-blockers, carbonic anhydrase inhibitors, hyperosmotics, cholinergics, adrenergic agonists and prostaglandin analogs. However, some patients can have high eye pressure for years and never develop damage. However, optic nerve damage may occur with normal pressure, known as normal-tension glaucoma. In some embodiments, a method of providing neuroprotection to the optic nerve is provided, wherein the method comprises administering to the patient an effective amount of CGRP receptor antagonist. In some embodiments, the patient is suffering from glaucoma. In some embodiments, the patient is suffering from diabetes.

Without being limiting, two examples of glaucoma include open-angle and angle closure glaucoma. Open-angle glaucoma is the most common form of glaucoma and accounts for at least 90% of all glaucoma cases. Open-angle glaucoma is caused by the slow clogging of the drainage canals, resulting in increased eye pressure, has a wide and open angle between the iris and cornea, develops slowly and is a lifelong condition having symptoms and damage that are not noticed. The term "open-angle" means that the angle where the iris meets the cornea has a wide and open angle between the iris and the cornea. It is the most common type of glaucoma, and affects about three million Americans.

Angle closure glaucoma is a less common form of glaucoma and is caused by blocked drainage canals, resulting in a sudden rise in intraocular pressure. In angle closure glaucoma, the iris is not as wide and open as it should be and has a closed or narrow angle between the iris and cornea. This type of glaucoma develops very quickly, has very noticeable symptoms and damage and demands immediate medical attention. Without being limiting, other variants of open-angle and angle-closure glaucoma can include secondary glaucoma, pigmentary glaucoma, pseudoexfoliative glaucoma, traumatic glaucoma, neurovascular glaucoma, iridocorneal endothelial syndrome (ICE) and Uveitic glaucoma. Vision loss from any type of glaucoma, once it has occurred is permanent.

The term "familial hypercholesterolemia" (FH), as used herein, is an inherited disorder that is characterized by high cholesterol levels, specifically elevated levels of low-density lipoprotein (LDL, or "bad cholesterol"), in the blood and early cardiovascular disease. Since individuals with FH have an underlying body biochemistry that is slightly different, their high cholesterol levels are less responsive to the types of cholesterol control methods which are usually more effective in people without FH (such as dietary modification and statin tablets). FH can lead to aggressive and premature cardiovascular disease. Without being limiting, problems caused by FH can include heart attacks, strokes, and narrowing of our heart valves. For individuals with FH, although diet and lifestyle are important, they are not the cause of high levels of LDL. In some FH patients, genetic mutations make the liver incapable of metabolizing (or removing) excess LDL. The result is very high LDL levels which can lead to premature cardiovascular disease (CVD).

In some embodiments, a method of lowering levels of LDL in a patient suffering from FH is provided, wherein the method comprises administering to the patient an effective amount of CGRP receptor antagonist. In some embodiments, the patient has been identified or selected to receive a drug or therapy for controlling LDL levels. In some embodiments, the therapy is administration for controlling LDL levels comprises statins, selective cholesterol absorption inhibitors, resins, bile acid sequestrant, bile acid-binding drugs or lipid lowering therapies. In some embodiments, the method further comprises monitoring or measuring the level or amount of LDL in said patient before, during, or after administration of the effective amount of CGRP receptor antagonist. In some embodiments, the patient is already receiving therapy for lowering LDL levels. In some embodiments, the effective amount of CGRP receptor antagonist is administered with a drug for lowering LDL levels. In some embodiments, the patient is a male.

Heterozygous FH is normally treated with statins, bile acid sequestrants, or other lipid lowering agents that lower cholesterol levels. Homozygous FH often does not respond to pharmaceutical therapy and may require other treatments, including LDL apheresis (removal of LDL in a method similar to dialysis) and occasionally liver transplantation. The American Heart Association categorizes the risk of heart disease based on LDL levels. Less that 100 mg/dL is considered to be optimal and up to about 129 mg/dL is considered to be near optimal. Borderline high LDL ranges from about 130 mg/dL to 159 mg/dL and about 160 to about 189 mg/dL is considered high. Any amount above 190 mg/dL is categorized as very high. As many people with FH have levels of LDL at borderline LDL ranges or higher, new methods are desperately needed to control LDL levels in these individuals.

"Subject" or "Patient" as described herein, can refer to any organism upon which the embodiments may be used or administered, e.g., for experimental, diagnostic, prophylactic, and/or therapeutic purposes. Without being limiting, subjects can include animals (e.g., mammals such as mice, rats, rabbits, non-human primates, and humans; insects; worms; etc.). A patient can also be any subject that is registered or identified for receiving the methods of treatment as described herein.

"Combination therapy" as described herein, refers to a situation in which two or more different pharmaceutical agents are administered in overlapping regimens so that the subject is simultaneously exposed to the two or more different pharmaceutical agents.

"Therapeutically effective amount," as described herein, can refer to an amount of a therapeutic agent whose administration, when viewed in a relevant population, correlates with or is reasonably expected to correlate with achievement of a particular therapeutic effect, including for example, amelioration of disease or disorder or delay of progression of disease or disorder. The therapeutic effect may be objective (i.e., measurable by some test or marker) or subjective (i.e., subject gives an indication of or feels an effect). A therapeutically effective amount is commonly administered in a dosing regimen that may comprise multiple unit doses. For any particular therapeutic peptide, a therapeutically effective amount (and/or an appropriate unit dose within an effective dosing regimen) may vary, for example, depending on route of administration, or combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

"Prophylactically effective amount" as described herein, refers to an amount that can prevent, delay or reduce the severity of a particular disease or disorder in a patient a risk.

"Herpesvirus" as described herein, belongs to the herpesvirus family, Herpesviridae that infect humans. Without being limiting, symptoms can include watery blisters in the skin or mucous membranes. Lesions heal with a scab characteristic of herpetic disease. Sometimes, the viruses cause very mild or atypical symptoms during outbreaks. However, as neurotropic and neuroinvasive viruses, HSV-1 and -2 persist in the body by becoming latent and hiding from the immune system in the cell bodies of neurons. Herpesviruses can invade the nerves and nervous system. Shingles is due to a reactivation of varicella zoster virus (VZV), a herpesvirus, within a person's body. Chickenpox is due to an initial infection with VZV. Once chickenpox has resolved, the virus may remain inactive in nerve cells. People suffering from outbreaks of shingles may develop ongoing nerve pain which may last for months or years, a condition called postherpetic neuralgia. In some embodiments of the method of treatment provided herein, a patient suffering from a herpesvirus, is administered a CGRP antagonist.

"Ischemic event," or "ischemia" as defined herein, refers to inadequate blood supply to an organ or part of the body, and can include the heart muscles, for example. Reduction of circulation can lead to sensitive nerve tissue and muscle tissues.

DETAILED DESCRIPTION

As described herein, antagonists of the calcitonin gene-related peptide (CGRP) receptor can be used to control specific biological responses. In particular, the peptide antagonists of the CGRP receptor are useful in the treatment of neuritis, glaucoma and other neurodegenerative diseases and useful to provide neuroprotection and/or control of high LDL.

CGRP Peptide Antagonist for Administration

In some embodiments of the methods of treatment, the methods comprise administration of a peptide CGRP receptor antagonist, also referred to herein, variously, as a CGRP receptor peptide antagonist or CGRP peptide antagonist and/or CGRP antagonist. The peptide CGRP receptor antagonist can have the structure of Formula I:

$$X^1\text{—}Y^1\text{—}Z^1 \qquad (I)$$

wherein:

$X^1$ is an N-terminal fragment (i.e., region) of a modified calcitonin gene-related peptide comprising at least five to seven amino acid residues, where two amino acid residues of the N-terminal fragment are cysteine (Cys), wherein the final residue (i.e. the C-terminal end residue) is Cys, and wherein the residue immediately preceding the final Cys residue is a non-threonine substitution of a threonine (Thr) residue;

$Y^1$ is a central core region comprising 15 to more than 24, 15 to 24, 15 to 22, 18-22, or 19-20 residues where at least some of the residues of the central core are capable of forming an α-helix under physiological conditions, wherein at least one amino acid of the central core is arginine (Arg) or lysine (Lys) and the central core comprises an α-helix; and $Z^1$ is a modified C-terminal fragment (i.e., region) of modified calcitonin gene-related peptide comprising from five to seven amino acid residues with a C-terminal amide, where at least one amino acid residue of the C-terminal fragment is phenylalanine (Phe) tyrosine (Tyr), proline (Pro) or hydroxyproline (Hyp);

or pharmaceutically acceptable salt thereof.

In some embodiments, the CGRP antagonist for administration comprises an amino acid sequence having at least 60%, at least 70% or at least 80% sequence identity to the amino acid sequence of SEQ ID NOS: 1, 2, 3, 4, 5, 6, 7, 8, 9, 10, 11, 12, 13, 14, 15, 57 or 58 wherein said peptide retains antagonist activity.

In some embodiments, the CGRP antagonist for administration comprises an amino acid sequence having at least 90% sequence identity to the amino acid sequence of SEQ ID NOS: 1, 2, 3, 4, 5, 6, 7, 8, 9, 10, 11, 12, 13, 14, 15, 57 or 58 wherein said peptide retains antagonist activity.

In some embodiments of the methods of treatment described herein, the $X^1$ region of Formula I, has the characteristics that a residue which precedes the C-terminal cysteine by four, five or six amino acid positions is also a cysteine, such that the two aforementioned cysteines can form a disulfide bond. Residues between the two Cys residues involved in the disulfide bond are unconstrained in sequence except that the residue preceding the C-terminal Cys residue of the fragment must not be a Thr, as mentioned above, and that there may not be more than two cysteines in the C-terminal 7 residues of the $X^1$ fragment. The aforementioned disulfide bond stabilizes the structure of $X^1$, facilitating both formation of the alpha-helix in $Y^1$, below, and binding of $X^1$ to the transmembrane component of a CGRP receptor in competition with CGRP.

In some embodiments of the methods of treatment described herein, a CGRP peptide antagonist is administrated. The antagonist as disclosed herein comprises a central core $Y^1$ comprising 15 to 22 residues. In some embodiments the antagonist as disclosed herein comprises a central core $Y^1$ comprising more than 24, 15 to 24, 15 to 22, 18-22, or 19-20 residues where at least some of the residues of the central core are capable of forming an α-helix under physiological conditions. The fourth residue from the N-terminus of this central core is frequently a positively charged residue, either Arginine (Arg) or Lysine (Lys). The eighteenth residue is frequently Arginine. The length of the central core is constrained not by the number of residues per se but by the steric considerations that require $X^1$ and $Z^1$ to be positioned so that they may interact with a target receptor at the cell membrane surface and at an extracellular domain, respectively, in competition with CGRP.

$Z^1$ is a modified C-terminal fragment (i.e., region) of a modified calcitonin gene-related peptide comprising from five to seven amino acid residues or more, with a C-terminal amide, and wherein at least one amino acid of the $Z^1$ region is phenylalanine (Phe), proline (Pro), tyrosine (Tyr), or hydroxyproline (Hyp). Like $Y^1$ above, $Z^1$ is constrained not by its sequence but by a functional requirement. In the case of $Z^1$ that requirement is that it interact with a target receptor at a site in its extracellular domain such that when the antagonist binds the CGRP receptor, in competition with CGRP, $X^1$ is positioned to interact with the receptor at the cell surface and $Z^1$ interacts with a RAMP portion of the receptor.

In some embodiments of the methods of treatment described herein, the CGRP peptide antagonist for administration comprises an amino acid sequence having at least 60%, at least 70% or at least 80% sequence identity to the amino acid sequence of SEQ ID NOS: 1, 2, 3, 4, 5, 6, 7, 8, 9, 10, 11, 12, 13, 14, 15, 57 or 58, wherein said peptide retains antagonist activity.

In some embodiments of the methods of treatment described herein, the CGRP peptide antagonist for administration comprises an amino acid sequence having at least 90% sequence identity to the amino acid sequence of SEQ ID NOS: 1, 2, 3, 4, 5, 6, 7, 8, 9, 10, 11, 12, 13, 14, 15, 57 or 58, wherein said peptide retains antagonist activity.

In some embodiments of the methods of treatment, the CGRP peptide antagonist for administration comprises a core region of 18-22 residues.

In some embodiments of the instant methods, the CGRP peptide antagonist for administration comprises the structure of Formula I, wherein the N-terminal fragment ($X^1$) comprises:

$X^{11}$-$X^{12}$-$X^{13}$-$X^{14}$-$X^{15}$-$X^{16}$-$X^{17}$ (SEQ ID NO: 16), where:

$X^{11}$ can be selected from the group consisting of alanine (Ala), cysteine (Cys), glycine (Gly), isoleucine (Ile), leucine (Leu), methionine (Met), phenylalanine (Phe), proline (Pro), tryptophan (Trp), and valine (Val);

$X^{12}$ can be selected from the group consisting of cysteine (Cys), serine (Ser), and tyrosine (Tyr);

$X^{13}$ can be selected from the group consisting of arginine (Arg), asparagine (Asn), aspartic acid (Asp), cysteine (Cys), glutamic acid (Glu), glutamine (Gln), histidine (His), lysine (Lys), serine (Ser), threonine (Thr), tyrosine (Tyr), and valine (Val);

$X^{14}$ can be selected from the group consisting of arginine (Arg), asparagine (Asn), aspartic acid (Asp), glutamic acid (Glu), glutamine (Gln), histidine (His), leucine (Leu), lysine (Lys), phenylalanine (Phe), serine (Ser), threonine (Thr), tyrosine (Tyr), and valine (Val);

$X^{15}$ can be selected from the group consisting of alanine (Ala), glycine (Gly), isoleucine (Ile), leucine (Leu), methionine (Met), phenylalanine (Phe), serine (Ser), tryptophan (Typ), and valine (Val);

$X^{16}$ can be selected from the group consisting of alanine (Ala), glycine (Gly), isoleucine (Ile), leucine (Leu), methionine (Met), phenylalanine (Phe), serine (Ser), tryptophan (Typ), and valine (Val); and $X^{17}$ is cysteine (Cys), and is capable of forming a disulfide bridge with a cysteine residue in $X^{11}$, $X^{12}$, or $X^{13}$; and with the further limitation that only two residues of $X^1$ (that is, $X^{17}$ and only one of $X^{11}$, $X^{12}$, and $X^{13}$) are cysteine residues.

In some embodiments of the methods of treatment, the CGRP peptide antagonist in the methods of treatment comprises the structure of Formula I, $X^{11}$ is selected from the group consisting of Ala, Cys, and Gly. In some embodiments of the methods of treatment, the CGRP peptide antagonist comprising the structure of Formula I, $X^{12}$ is selected from the group consisting of Cys and Ser, with the caveat that only one of $X^{11}$ and $X^{12}$ can be Cys. In some embodiments of the methods of treatment, the CGRP peptide antagonist comprising the structure of Formula I, $X^{13}$ is selected from the group consisting of Arg, Asn, Asp, and Val. In some embodiments of the methods of treatment, the CGRP peptide antagonist comprising the structure of Formula I, $X^{14}$ is selected from the group consisting of Leu, Phe, and Thr. In some embodiments of the methods of treatment, the CGRP peptide antagonist comprising the structure of Formula I, $X^{11}$ is selected from the group consisting of Ala, Gly, and Ser. In some embodiments of the methods of treatment, the CGRP peptide antagonist comprising the structure of Formula I, $X^{11}$ is selected from the group consisting of Ala, Ile, Leu, Ser, and Val.

In some embodiments of the methods of treatment, the CGRP peptide antagonist for administration comprises the structure of Formula I, $X^{11}$-$X^{12}$-$X^{13}$-$X^{14}$-$X^{15}$-$X^{16}$-$X^{17}$ is selected from the group consisting of NH2-Ala-Cys-Asp-Thr-Ala-Ala-Cys (SEQ ID NO: 17), NH2-Ala-Cys-Asp-Thr-Ala-Ser-Cys (SEQ ID NO: 18), NH2-Ala-Cys-Asp-Thr-Ala-Val-Cys (SEQ ID NO: 19), NH2-Ala-Cys-Asn-Thr-Ala-Ala-Cys (SEQ ID NO: 20), NH2-Ala-Cys-Val-Leu-Gly-Ala-Cys (SEQ ID NO: 21), NH2-Ala-Cys-Arg-Phe-Gly-Ala-Cys (SEQ ID NO: 22), NH2-Ala-Cys-Asp-Leu-Ser-Ala-Cys (SEQ ID NO: 23), NH2-Ala-Cys-Asn-Leu-Ser-Ala-Cys (SEQ ID NO: 24), NH2-Cys-Ser-Asn-Thr-Ala-Ala-Cys (SEQ ID NO: 25), NH2-Ala-Cys-Asp-Thr-Ala-Leu-Cys (SEQ ID NO: 26), NH2-Ala-Cys-Asp-Thr-Ala-Ile-Cys (SEQ ID NO: 27), NH2-Ala-Cys-Asp-Thr-Ala-Leu-Cys (SEQ ID NO: 28), NH2-Ala-Cys-Asp-Thr-Ala-Ile-Cys (SEQ ID NO: 29), NH2-Ala-Cys-Asp-Leu-Ser-Val-Cys (SEQ ID NO: 30), NH2-Ala-Cys-Asp-Leu-Ser-Val-Cys (SEQ ID NO: 31), NH2-Ala-Cys-Asn-Leu-Ser-Val-Cys (SEQ ID NO: 32), and NH2-Cys-Ser-Asn-Thr-Ala-Val-Cys (SEQ ID NO: 33).

In some embodiments of the methods of treatment, one or more additional residues are fused N-terminally to $X^{11}$, thereby generating a polypeptide with an N-terminal extension of residues with respect to $X^{11}$. In some embodiments of the instant methods of treatment, this extension affects the stability of the antagonist after administration.

In some embodiments of the methods of treatment, the CGRP peptide antagonist for administration comprises the structure of Formula I, wherein the central core region ($Y^1$) comprises a central core fragment of human or salmon calcitonin. In some embodiments of the methods of treatment, the fragment of human or salmon calcitonin comprises 18 to 21 amino acids. In some embodiments of the methods of treatment, the fragment of human or salmon calcitonin comprises 18 to 20 amino acids. In some embodiments of the methods of treatment, the CGRP peptide antagonist for administration comprises the structure of Formula I, $Y^1$ comprises 19 to 20 amino acids. In some embodiments of the methods of treatment, the CGRP peptide antagonist comprising the structure of Formula I, $Y^1$ is -Val-Leu-Gly-Arg-Leu-Ser-Gln-Glu-Leu-His-Arg-Leu-Gln-Thr-Tyr-Pro-Arg-Thr-Asn- (SEQ ID NO: 34) or -Val-Leu-Gly-Lys-Leu-Ser-Gln-Glu-Leu-His-Lys-Leu-Gln-Thr-Tyr-Pro-Arg-Thr-Asn- (SEQ ID NO: 35). In some embodiments of the methods of treatment, the CGRP peptide antagonist for administration comprises the structure of Formula I, $Y^1$ has 95% sequence identity with -Val-Leu-Gly-Arg-Leu-Ser-Gln-Glu-Leu-His-Arg-Leu-Gln-Thr-Tyr-Pro-Arg-Thr-Asn- (SEQ ID NO: 34) or -Val-Leu-Gly-Lys-Leu-Ser-Gln-Glu-Leu-His-Lys-Leu-Gln-Thr-Tyr-Pro-Arg-Thr-Asn- (SEQ ID NO: 35).

In some embodiments of the methods of treatment, the CGRP peptide antagonist for administration comprises the structure of Formula I, the central core comprises a fragment of a calcitonin from any of a range of species. In some embodiments of the methods of treatment, $Y^1$ can have a 60%, 65%, 70%, 75%, 80%, 85%, 90%, or 95% sequence identity with the $Y^1$ of SEQ ID NO: 34 (Val-Leu-Gly-Arg-Leu-Ser-Gln-Glu-Leu-His-Arg-Leu-Gln-Thr-Tyr-Pro-Arg-Thr-Asn-). In some embodiments of the methods of treatment, the CGRP peptide antagonist comprising the structure of Formula I, $Y^1$ can be -Val-Leu-Gly-Lys-Leu-Ser-Gln-Glu-Leu-His-Lys-Leu-Gln-Thr-Tyr-Pro-Arg-Thr-Asn- (SEQ ID NO: 35) or -Val-Leu-Gly-Lys-Leu-Ser-Gln-Glu-Leu-His-Lys-Leu-Gln-Thr-Tyr-Pro-Arg-Thr-Asp- (SEQ ID NO: 36) or -Val-Leu-Gly-Lys-Leu-Ser-Gln-Glu-Leu-His-Lys-Leu-Gln-Thr-Phe-Pro-Arg-Thr-Asn- (SEQ ID NO: 37) or -Val-Leu-Gly-Lys-Leu-Ser-Gln-Asp-Ile-His-Lys-Leu-Gln-Thr-Tyr-Pro-Arg-Thr-Asn- (SEQ ID NO: 38) or -Val-Leu-Gly-Lys-Leu-Ser-Gln-Glu-Leu-His-Lys-Met-Gln-Thr-Tyr-Pro-Arg-Thr-Asp- (SEQ ID NO: 39) or -Leu-Leu-Gly-Lys-Leu-Ser-Gln-Glu-Leu-His-Arg-Leu-Gln-Thr-Tyr-Thr-Arg-Thr-Asp- (SEQ ID NO: 40) or -Val-Leu-Gly-Lys-Leu-Ser-Gln-Asp-Leu-His-Lys-Leu-Gln-Thr-Phe-Pro-Arg-Thr-Asp- (SEQ ID NO: 41) or -Met-Leu-Gly-Lys-Leu-Ser-Gln-Asp-Leu-His-Lys-Leu-Gln-Thr-Phe-Pro-Arg-Thr-Asp- (SEQ ID NO: 42) or -Val-Leu-Gly-Lys-Leu-Ser-Gln-Asp-Ile-His-Lys-Leu-Gln-Thr-His-Pro-Arg-Thr-Asp- (SEQ ID NO: 43). In some embodiments of the methods of treatment, $Y^1$ can have a 60% or greater sequence identity with any of the $Y^1$ of the sequences immediately above.

Some embodiments of the instant method of treatment provide $Y^1$ polypeptides that have at least about 60% amino acid sequence identity, alternatively at least about 61% amino acid sequence identity, alternatively at least about 62% amino acid sequence identity, alternatively at least about 63% amino acid sequence identity, alternatively at least about 64% amino acid sequence identity, alternatively at least about 65% amino acid sequence identity, alternatively at least about 66% amino acid sequence identity, alternatively at least about 67% amino acid sequence identity, alternatively at least about 68% amino acid sequence identity, alternatively at least about 69% amino acid sequence identity, alternatively at least about 70% amino acid sequence identity, alternatively at least about 71% amino acid sequence identity, alternatively at least about 72% amino acid sequence identity, alternatively at least about 73% amino acid sequence identity, alternatively at least about 74% amino acid sequence identity, alternatively at least about 75% amino acid sequence identity, alternatively at least about 76% amino acid sequence identity, alternatively at least about 77% amino acid sequence identity, alternatively at least about 78% amino acid sequence identity, alternatively at least about 79% amino acid sequence identity, alternatively at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a $Y^1$ polypeptide fragment listed above.

In some embodiments of the methods of treatment, the CGRP peptide antagonist for administration comprises the structure of Formula I, wherein $Z^1$ comprises $Z^{11}$-$Z^{12}$—$Z^{13}$—$Z^4$-$Z^{15}$—$Z^{16}$ (SEQ ID NO: 45) where:

$Z^{11}$ is selected from the group consisting of Ala, Gly, Ile, Leu, Met, Phe, Pro, Trp, and Val;

$Z^{12}$ is selected from the group consisting of Ala, Gly, Ile, Leu, Met, Phe, Pro, Trp, and Val;

$Z^{13}$ is selected from the group consisting of serine (Ser), and tyrosine (Tyr);

$Z^{14}$ is selected from the group consisting of Arg, Asn, Asp, Glu, Gln, His, Lys, Ser, Thr, and Tyr;

$Z^{15}$ is selected from the group consisting of Ala, Gly, Ile, Leu, Met, Phe, Pro, Trp, and Val; and $Z^{16}$ is selected from the group consisting of Ala, Gly, Ile, Leu, Met, Phe, Pro, Trp, and Val. In some embodiments, $Z^{11}$ is Val. In some embodiments, $Z^{12}$ is Gly. In some embodiments, $Z^{13}$ is Ser. In some embodiments, $Z^4$ is Lys. In some embodiments, $Z^{11}$ is Ala. In some embodiments, $Z^{16}$ is Phe. In some embodiments, $Z^{11}$-$Z^{12}$—$Z^{13}$—$Z^{14}$-$Z^{15}$—$Z^{16}$ is -Val-Gly-Ser-Lys-Ala-Phe such that the C-terminus of the polypeptide is a carboxy moiety (SEQ ID NO: 46), or -Val-Gly-Ser-Lys-Ala-Phe-NH2, such that the C-terminus of the polypeptide is a carboxamide moiety (SEQ ID NO: 47).

In some embodiments of the methods of treatment, the C-terminal residue of $Z^1$ is Phenylalanine, Tyrosine, Proline or Hydroxyproline. In some embodiments the C-terminal residue of $Z^1$ is Phenylalanine.

In some embodiments $Z^1$ comprises at least one Phe residue.

In some embodiments the C-terminus of $Z^1$ is modified so that it is bounded by an amidated carboxy (—C(=O)NH2) moiety.

In some embodiments of the methods of treatment, the CGRP peptide antagonist for administration comprises the structure of Formula I, $X^1$ is selected from the group consisting of NH2-Ala-Cys-Asp-Thr-Ala-Ala-Cys- (SEQ ID NO: 17), NH2-Ala-Cys-Asp-Thr-Ala-Ser-Cys- (SEQ ID NO: 18), NH2-Ala-Cys-Asp-Thr-Ala-Val-Cys- (SEQ ID NO: 19), NH2-Ala-Cys-Asn-Thr-Ala-Ala-Cys- (SEQ ID NO: 20), NH2-Ala-Cys-Val-Leu-Gly-Ala-Cys-, NH2-Ala-Cys-Arg-Phe-Gly-Ala-Cys- (SEQ ID NO: 21), NH2-Ala-Cys-Arg-Phe-Gly-Ala-Cys- (SEQ ID NO: 22), NH2-Ala-Cys-Asp-Leu-Ser-Ala-Cys- (SEQ ID NO: 23), NH2-Ala-Cys-Asn-Leu-Ser-Ala-Cys- (SEQ ID NO: 24), Cys-Ser-Asn-Thr-Ala-Ala-Cys- (SEQ ID NO: 25), NH2-Ala-Cys-Asp-Thr-Ala-Leu-Cys- (SEQ ID NO: 26), NH2-Ala-Cys-Asp-Thr-Ala-Ile-Cys- (SEQ ID NO: 27), NH2-Ala-Cys-Asp-Thr-Ala-Leu-Cys- (SEQ ID NO: 28), NH2-Ala-Cys-Asp-Thr-Ala-Ile-Cys- (SEQ ID NO: 29), NH2-Ala-Cys-Asp-Leu-Ser-Val-Cys- (SEQ ID NO: 30), NH2-Ala-Cys-Asp-Leu-Ser-Val-Cys- (SEQ ID NO: 31), NH2-Ala-Cys-Asn-Leu-Ser-Val-Cys (SEQ ID NO: 32), and NH2-Cys-Ser-Asn-Thr-Ala-Val-Cys- (SEQ ID NO: 33); $Y^1$ can be -Val-Leu-Gly-Arg-Leu-Ser-Gln-Glu-Leu-His-Arg-Leu-Gln-Thr-Tyr-Pro-Arg-Thr-Asn- (SEQ ID NO: 34) or -Val-Leu-Gly-Lys-Leu-Ser-Gln-Glu-Leu-His-Lys-Leu-Gln-Thr-Tyr-Pro-Arg-Thr-Asn- (SEQ ID NO: 35); and $Z^1$ can be -Val-Gly-Ser-Lys-Ala-Phe having a carboxy-terminus (SEQ ID NO: 46) or -Val-Gly-Ser-Lys-Ala-Phe-NH2 (SEQ ID NO: 47).

In some embodiments of the methods of treatment, the CGRP peptide antagonist for administration comprises the structure of Formula I, the antagonist comprises from 28 to 35 amino acid residues, from 31 to 37 amino acid residues, from 31 to 33 amino acid residues or 32 amino acid residues.

In some embodiments of the methods of treatment, the CGRP peptide antagonist for administration comprises the structure of Formula I, the antagonist comprises -Ala-Cys-Asp-Thr-Ala-$X^{16}$-Cys- (SEQ ID NO: 49), wherein $X^{16}$ is any amino acid residue other than Thr.

In some embodiments of the methods of treatment, the CGRP peptide antagonist for administration comprises the structure of Formula I, the antagonist comprises a first peptide fragment/region having seven amino acid residues or less, wherein said first peptide fragment has a sequence from modified calcitonin gene-related peptide. In some embodiments, the CGRP peptide antagonist comprising the structure of Formula I, the antagonist comprises a second peptide fragment having seven amino acid residues or less, wherein said first and second peptide fragments are non-contiguous and each independently have a sequence which may be modified from calcitonin gene-related peptide. In some embodiments, the CGRP peptide antagonist comprising the structure of Formula I, the antagonist comprises a third peptide fragment having 20 amino acid residues or less, wherein said third peptide fragment has a sequence from salmon calcitonin. In some embodiments, the CGRP peptide antagonist comprising the structure of Formula I, the second peptide fragment and the third peptide fragment are contiguous.

In some embodiments of the methods of treatment, the CGRP peptide antagonist for administration comprises a structure of NH2-Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2 (SEQ ID NO: 1), or a pharmaceutical acceptable salt thereof. In some embodiments, the antagonist has a structure of NH2-Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2 (SEQ ID NO: 2), or a pharmaceutical acceptable salt thereof. In some embodiments of the methods of treatment, the CGRP peptide antagonist for administration comprises a structure of NH2-Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2 (SEQ ID NO: 3), or a pharmaceutical acceptable salt thereof. In some embodiments of the methods of treatment, the CGRP peptide antagonist for administration comprises a structure of NH2-Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2 (SEQ ID NO: 4), or a pharmaceutical acceptable salt thereof. In some embodiments of the methods of treatment, the CGRP peptide antagonist for administration comprises a structure of NH2-Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2 (SEQ ID NO: 5), or a pharmaceutical acceptable salt thereof. In some embodiments of the methods of treatment, the CGRP peptide antagonist for administration comprises a structure of NH2-Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2 (SEQ ID NO: 6), or a pharmaceutical acceptable salt thereof. In some embodiments of the methods of treatment, the CGRP peptide antagonist for administration comprises a structure of NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2 (SEQ ID NO: 7), or a pharmaceutical acceptable salt thereof. In some embodiments, the antagonist has a structure of NH2-Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2 (SEQ ID NO: 8), or a pharmaceutical acceptable salt thereof. In some embodiments, the antagonist has a structure of NH2-Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2 (SEQ ID NO: 9), or a pharmaceutical acceptable salt thereof. In some embodiments of the methods of treatment, the CGRP peptide antagonist for administration comprises a structure of NH2-Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2 (SEQ ID NO: 10), or a pharmaceutical acceptable salt thereof. In some embodiments of the methods of treatment, the CGRP peptide antagonist for administration comprises a structure of NH2-Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2 (SEQ ID NO: 11), or a pharmaceutical acceptable salt thereof. In some embodiments of the methods of treatment, the CGRP peptide antagonist for administration comprises a structure of NH2-Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2 (SEQ ID NO: 12), or a pharmaceutical acceptable salt thereof. In some embodiments of the methods of treatment, the CGRP peptide antagonist for administration comprises a structure of or NH2-Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Thr-Asn-Thr-Gly-Ser-Gly-Thr-Pro-NH2 (SEQ ID NO: 13), or a pharmaceutical acceptable salt thereof. In some embodiments, the antagonist has a structure of Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Val-Asp-Pro-Ser-Ser-Pro-His-Ser-Tyr-NH2 (SEQ ID NO: 14), or a pharmaceutical acceptable salt thereof. In some embodiments of the methods of treatment, the CGRP peptide antagonist for administration comprises a structure of Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH2 (SEQ ID NO: 15), or a pharmaceutical acceptable salt thereof. In some embodiments of the methods of treatment, the CGRP peptide antagonist for administration comprises a structure of NH2-Ala-Cys-Asp-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2 (SEQ ID NO: 57) or a pharmaceutical acceptable salt thereof. In some embodiments of the methods of treatment, the CGRP peptide antagonist for administration comprises a structure of NH2-Ala-Cys-Asp-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH2 (SEQ ID NO: 58), or a pharmaceutically acceptable salt thereof. The CGRP peptide antagonist of the present disclosure can also be administered within a pharmaceutical composition comprising one of the compounds above. The pharmaceutical composition can be used in a method of any one of the embodiments provided herein, the method comprising administering to an individual an effective amount of a CGRP peptide antagonist.

In some embodiments of the methods of treatment, the CGRP peptide antagonist for administration comprises the structure of Formula I, wherein $Y^1$ includes -Ala-Glu-Ala-Ala-Ala-Lys-Glu-Ala-Ala-Ala-Lys-Glu-Ala-Ala-Ala-Lys-Ala- (SEQ ID NO: 50), -Ala-Lys-Ala-Ala-Ala-Glu-Lys-Ala-Ala-Ala-Glu-Lys-Ala-Ala-Ala-Glu-Ala- (SEQ ID NO: 51), -Ala-Glu-Ala-Ala-Lys-Ala-Glu-Ala-Ala-Lys-Ala-Glu-Ala-Ala-Lys-Ala- (SEQ ID NO: 52), or -Ala-Lys-Ala-Ala-Glu-Ala-Lys-Ala-Ala-Glu-Ala-Lys-Ala-Ala-Glu-Ala-Lys-Ala-Ala-Glu-Ala- (SEQ ID NO: 53).

In some embodiments of the methods of treatment, the CGRP antagonist comprises a sequence selected from the group consisting of the sequences set forth in SEQ ID NO: 1, 2, 3, 4, 5, 6, 7, 8, 9, 10, 11, 12 and 13.

In some embodiments of the methods of treatment, the CGRP peptide antagonist for administration comprises an amino acid sequence having at least 60% sequence identity to the amino acid sequence of SEQ ID NOS: 1, 2, 3, 4, 5, 6, 7, 8, 9, 10, 11, 12, 13, 14, 15, 57 or 58, wherein said peptide retains antagonist activity. In some embodiments of the methods of treatment, the CGRP peptide antagonist for administration comprises an amino acid sequence having at least 70% sequence identity to the amino acid sequence of SEQ ID NOS: 1, 2, 3, 4, 5, 6, 7, 8, 9, 10, 11, 12, 13, 14, 15, 57 or 58, wherein said peptide retains antagonist activity. In some embodiments of the methods of treatment, the CGRP peptide antagonist for administration comprises an amino acid sequence having at least 80% sequence identity to the amino acid sequence of SEQ ID NOS: 1, 2, 3, 4, 5, 6, 7, 8, 9, 10, 11, 12, 13, 14, 15, 57 or 58, wherein said peptide retains antagonist activity. In some embodiments, the amino acid sequence can have at least 90% sequence identity to the amino acid sequence of SEQ ID NOS: 1, 2, 3, 4, 5, 6, 7, 8, 9, 10, 11, 12, 13, 14, 15, 57 or 58, wherein said peptide retains antagonist activity. In some embodiments, the amino acid sequence can have at least 95% sequence identity to the amino acid sequence of SEQ ID NOS: 1, 2, 3, 4, 5, 6, 7, 8, 9, 10, 11, 12, 13, 14, 15, 57 or 58, wherein said peptide retains antagonist activity. In some embodiments, the amino acid sequence can have at least 97% sequence identity to the amino acid sequence of SEQ ID NOS: 1, 2, 3, 4, 5, 6, 7, 8, 9, 10, 11, 12, 13, 14, 15, 57 or 58, wherein said peptide retains antagonist activity.

Doses of the Antagonist and Routes of Administration

In some embodiments of the methods of treatment, the CGRP peptide antagonist can be administered to a patient susceptible to or otherwise at risk of a particular neurodegenerative disease and that is sufficient to prevent, delay or lessen the severity of such disease. Such an amount is defined to be a "prophylactically effective amount" or "prophylactically effective dose" and can also be referred to as a "therapeutically effective dose." In this use, the precise amounts to be administered depend, for example, on the patient's state of health and weight, and can be readily determined by one of ordinary skill in the art. In a preferred embodiment, the antagonist can be administered to a patient in need of neuroprotection.

Without being limiting, a patient in need of neuroprotection has suffered from an assault likely to cause nerve damage such as, for example, an ischemic event, a nerve injury from a drug or a disease, or intraocular pressure affecting the optic nerve.

Patients in need of neuroprotection can suffer from neurodegenerative diseases such as Parkinson's disease, progressive supranuclear palsy, corticobasal degeneration and multisystem atrophy.

In some embodiments of the methods of treatment, the CGRP antagonists can be administered, in a therapeutically effective amount, to a patient suffering from spontaneous nerve activity resulting, for example, in pain or discomfort and/or contributing to progressive nerve damage. Such spontaneous nerve activity may be the result of acute of chronic stimulation or chronic dysfunction of nerves, especially the C-nociceptors. In some embodiments, the patient in need of reduction of spontaneous nerve activity is suffering from a Herpesvirus. In some embodiments, the patient in need of reduction of spontaneous nerve activity is suffering from shingles.

In some embodiments of the methods of treatment, the CGRP peptide antagonists can be administered to a patient suffering from high LDL levels in a therapeutically effective amount, that is an amount sufficient to reduce said LDL levels. In this use, the precise amounts to be administered depend, for example, on the patient's state of health and weight, and can be readily determined by one of ordinary skill in the art.

The dosage ranges for the administration of an antagonist for the instant methods described herein, are those sufficient to produce a therapeutic effect.

In some embodiments of the methods of treatment provided herein, the CGRP receptor peptide antagonists are provided in a pharmaceutical composition comprising the CGRP receptor peptide antagonist and inactive ingredients such as a pharmaceutical carrier or diluent. The peptide antagonist containing a pharmaceutical composition can be administered by any means, as known to those of skill in the art, and include, without limitation, oral, pulmonary, parenteral (intramuscular, intraperitoneal, intravenous, or subcutaneous injection), inhalational (via a fine powder formulation, or aerosol), transdermal, intranasal, intraocular, buccal or sublingual routes of administration and can be formulated in dosage forms appropriate for each route of administration. In some embodiments, the peptide antagonist containing pharmaceutical composition is administered is administered topically, dermally, intradermally, subcutaneously, via dermal infusion, via subcutaneous infusion, intraocularly, buccally, intravenously, nasally, intraocularly, via inhalation, intramuscularly, sublingually or orally. See, for example, Bernstein, et al. PCT Patent Publication No. WO 93/25221, published Dec. 23, 1993; Pitt, et al. PCT Patent Publication No. WO 94/17784, published Aug. 18, 1994; and Pitt, et al. European Patent Application 613,683, published Sep. 7, 1994.

Although the exact dosage will be determined on an indication-by-indication basis, in most cases, some generalizations regarding the dosage can be made. The daily dosage regimen for an adult human patient may be, for example, an intraocular, intravenous, intraperitoneal, subcutaneous, or intramuscular dose of the antagonist at an exemplary range of between 0.001 mg and 100 mg, or an exemplary range of between 0.005 mg and 5 mg. Those of skill in the art will appreciate that dosing for topical, transdermal, oral, pulmonary (via inhalation), intranasal, buccal, sublingual, or related non-parenteral routes of administration may be higher for parenteral administration. Dosing in this case may be, for example, may be greater than 100 mg, for example, may be 200 mg, 300 mg, 400 mg, 600 mg, 500 mg, 1000 mg, or any amount in between any two of the aforementioned amounts. Additionally, the CGRP antagonist may be formulated with one or more ingredients that facilitate administration and/or uptake of the CGRP peptide. In cases of administration of a pharmaceutically acceptable salt, dosages may be calculated as the free base. In some embodiments of the methods described herein, the composition is administered at least once daily, once a week, twice a week or three times a week, or four times a week. In some embodiments of the method of treatment described herein, the composition is administered 1, 2, 3 or 4 times per day or as a single acute dose. In some embodiments of the methods described herein, the CGRP antagonist may be administered as a slow release formulation, for example, via depot injection or via infusion pump. For example, the CGRP antagonist may be formulated to allow for once-monthly dosing or for use in slow release micro pump devices that allow for once yearly dosing (ex. an implanted osmotic pump device for delivery)

Suitable routes of administration for the instant methods of administration are likewise known to those of skill in the art and may include, for example and without limitation, oral, ocularly, transmucosal or topical; parenteral delivery, including intramuscular, subcutaneous, intravenous, intramedullary injections, intrathecal, intraperitoneal, intranasal, or intraocular injections, as well as needle-free subcutaneous delivery. Alternatively, the antagonist can be part of any embodiments of the compositions as described herein and may be administered by continuous intravenous infusion, preferably at a dose of each active ingredient up to 1000 mg per day. Subjects suffering from chronic nerve pain can benefit from a continuous intravenous infusion or a controlled injection, for example from an infusion pump. Subjects suffering from glaucoma can benefit from ocular administration of the composition. In some embodiments of the methods described herein, the dose of the active ingredient is 50 µg, 60 µg, 70 µg, 80 µg, 90 µg, 100 µg, 200 µg, 300 µg, 400 µg, 500 µg, 600 µg, 700 µg, 800 µg, 900 µg, 1 mg, 5 mg, 10 mg, 40 mg, 50 mg, 100 mg, 200 mg, 300 mg, 400 mg, 50 mg, 100 mg, 200 mg, 300 mg, 400 mg or 500 mg 1000 mg or 2000 mg or any amount in between any two aforementioned values. In some embodiments, the aforementioned dosage is administered in a single dose. In some embodiments, the peptides will be administered for a period of continuous therapy, for example for a week or more, or for months or years.

Typically, the dose range of the composition administered to the patient can be from about 0.000001 to about 10 mg/kg of the patient's body weight. In some embodiments of the methods described herein, the dose range of the composition administered to the patient can be from 0.000001, 0.000010, 0.00010, 0.0010, 0.010, 0.10, 1, 5 or 10 mg/kg of the patient's body weight, or any amount in between any two aforementioned values. The dosage may be a single one or a series of two or more given in the course of one or more days, as is needed by the patient. In instances where human dosages for compounds have been established for at least some condition, the present embodiments will use those same dosages, or dosages that are between about 0.1% and 500%, more preferably between about 25% and 250% of the established human dosage. In some embodiments of the methods described herein, the dosage is 0.1%, 1%, 10%, 20%, 30%, 40%, 50%, 60%, 70%, 80%, 90%, 100%, 200%, 300%, 400% or 500% of the established human dosage or any amount in between any two aforementioned values. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

Other dose ranges for the method of administering the peptide antagonist in any of the methods provided herein will be apparent to the skilled practitioner based on data from initial dose-response curves and other data that can be obtained by routine methods. In cases of administration of a pharmaceutically acceptable salt, dosages may be calculated as the free base. In some embodiments, the peptide antagonist of any of the methods provided herein is administered 1 time, 2 times, 3 times or up to 4 times per day or as a single acute dose. In some embodiments, the peptides will be administered for a period of continuous therapy, for example for a week or more, or for months or years. Depending on the severity of a disease, such as chronic nerve pain experienced by a patient, administering is performed at least once daily, once a week, twice a week or three times a week.

In some embodiments of the methods of treatment, the compounds are administered in sustained or controlled release dosage forms, including without limitation, depot injections, osmotic pumps, transdermal (including electrotransport) patches, and the like, for prolonged and/or timed, pulsed administration at a predetermined rate In some embodiments of the methods of treatment, a patient is suffering from chronic nerve pain or a post ischemic event. Ischemic injury can occur due to interruption of circulation and may result in nerve damage. In some embodiments, a patient suffering from chronic nerve pain or a post ischemic event can be administered the antagonist by continuous intravenous infusion. In some embodiments, the antagonist is administered by an external infusion pump to allow a patient to self-deliver a controlled amount of antagonist as needed.

Any of the well-known techniques, carriers, and excipients may be used as suitable and as understood in the art; e.g., in Remington's Pharmaceutical Sciences, above.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Reducing Spontaneous Activity in Nerves Following Nerve Damage by Administration of a CGRP Antagonist In one aspect, a method of reducing spontaneous activity in nerves following nerve injury in a patient in need is provided, the method comprising administering to the patient an effective amount of CGRP receptor antagonist. The CGRP receptor antagonist can have the structure of Formula I as described in the embodiments above.

Dosages for the CGRP peptide antagonist for administration are described above. The CGRP peptide antagonist can be delivered alone or as a pharmaceutically acceptable salt thereof.

In some embodiments, the CGRP peptide antagonist comprises a sequence selected from the sequences set forth in SEQ ID NOS: 1-15, 57 or 58.

In some methods for reducing spontaneous activity in nerves, for example, following nerve injury, the CGRP receptor antagonist of Formula I ($X^1Y^1Z^1$) is administered topically, dermally, intradermally, subcutaneously, via dermal infusion, via subcutaneous infusion, intraocularly, buccally, intravenously, nasally, intraocularly, via inhalation, intramuscularly, sublingually or orally. In some embodiments, the administering is performed daily, once a week, twice a week, or three times a week. In some embodiments, the administering is performed four times a day, three times a day, twice a day or once a day.

In some embodiments, the nerve injury is from a drug, such as a chemotherapeutic. In some embodiments, the nerve injury is from a neurovascular disorder or neurodegenerative disease. In some embodiments, the drug causing a nerve injury is a heart medication (i.e. almitrine), an anti-cancer drug, antibiotic (i.e. chlorampheticol, Cipro), anti-fungal, immunosuppressant drug (i.e. Cyclosporine), muscle relaxant (i.e. Hydrazaline), anti-seizure medications (i.e. Phenytoin), anti-viral, anti-HIV drug, anti-inflammatory, centrally-acting muscle relaxant, nootropica agent, apoptosis inhibitor, growth factor agonist, smooth muscle relaxantium, chloroquine, isoniazid, metronidazole, nitrofurantoin, thalidomide, etanercept, infliximab, leflunomide, dapsone, phenytoin, disulfiram, didanosine, stavudine, Kenalog-40, triamcinolone, Clinacort or antiparasitic. In some embodiments, the nerves are C-Nociceptors or Group C nerve fibers.

In some embodiments, nerve injury is from a virus. In some embodiments, the patient is suffering from a herpesvirus. In some embodiments, the patient is suffering from shingles. In some embodiments, the CGRP receptor antagonist is administered within a pharmaceutically acceptable formulation. In some embodiments, the CGRP peptide antagonist comprises a sequence set forth in SEQ ID NO's: 1, 2, 3, 4, 5, 6, 7, 8, 9, 10, 11, 12, 13, 14, or 15. In some embodiments, the CGRP peptide antagonist comprises a sequence set forth in SEQ ID NO: 1.

In some embodiments, the patient has been identified or selected to receive a drug for neurodegenerative diseases or a virus.

Methods of Providing Neuroprotection by Administration of a CGRP Receptor Antagonist In another aspect, a method of providing neuroprotection in a patient in need thereof is provided. Neuroprotection refers to the preservation of neuronal structure and function. During a neurodegenerative insult, the relative preservation of neuronal integrity implies a reduction in the rate of neuronal loss over time. Neuroprotection is a widely explored treatment option for central nervous system (CNS) disorders. These CNS disorders can include but are not limited to neurodegenerative diseases, stroke, traumatic brain injury, spinal cord injury, and acute management of neurotoxin consumption (i.e. methamphetamine overdoses). Neuroprotection can be used to prevent or slow disease progression and secondary injuries by halting or at least slowing the loss of neurons. Despite differences in symptoms or injuries associated with CNS disorders, many of the mechanisms behind neurodegeneration are the same. Common mechanisms include increased levels in oxidative stress, mitochondrial dysfunction, excitotoxicity, inflammatory changes, iron accumulation, and protein aggregation. Common neuroprotective treatments are glutamate antagonists and antioxidants, which aim to limit excitotoxicity and oxidative stress respectively. It has been discovered that CGRP receptor antagonists likewise can be neuroprotective.

In some embodiments, a patient in need of neuroprotection has suffered from a neurodegenerative disease such as glaucoma, or suffered from an acute event such as stroke or spinal cord injury.

In some embodiments, a method of providing neuroprotection in a patient in need thereof is provided. The method comprises administering to the patient an effective amount of CGRP receptor antagonist. The CGRP receptor antagonist can be a peptide antagonist having the structure of Formula I, as described in the embodiments above.

Dosages for the CGRP peptide antagonist for administration are described above. The CGRP peptide antagonist can be delivered alone or as a pharmaceutically acceptable salt thereof.

In some embodiments, the CGRP peptide antagonist comprises a sequence set forth in one of SEQ ID NOS: 1, 2, 3, 4, 5, 6, 7, 8, 9, 10, 11, 12, 13, 14, 15, 57 or 58. In some embodiments, the CGRP peptide antagonist comprises a sequence set forth in one of SEQ ID NOS: 1, 2, 3, 4, 5, 6, 7, 8, 9, 10, 11, 12 or 13.

In some embodiments of the instant methods of administration, the CGRP receptor antagonist is administered parenterally, ocularly, intraocularly, buccally, sublingually, orally, topically, dermally, intradermally, subcutaneously, via dermal infusion, or via subcutaneous infusion. In some embodiments, the administering is performed daily, once a week, twice a week or three times a week. In some embodiments, the administering is performed four times a day, three times a day, twice a day, or once a day. In some embodiments, the CGRP receptor antagonist is formulated to allow for once a month or continuous administration. In some embodiments, the method further comprises monitoring or measuring a level of nerve activity function in said patient before, during or after administration of the effective amount of CGRP receptor antagonist. In some embodiments, the patient is suffering from glaucoma, diabetes, Parkinson's disease, Alzheimer's disease, multiple sclerosis, diabetic neuropathy, cerebrovascular ischemia, motor neuron disease, dementia, seizures, head injury or nerve damage. In some embodiments, the CGRP peptide antagonist comprises a sequence set forth in SEQ ID NO's: 1, 2, 3, 4, 5, 6, 7, 8, 9, 10, 11, 12, 13, 14, 15, 57 or 58. In some embodiments, the CGRP peptide antagonist comprises a sequence set forth in one of SEQ ID NOS: 1, 2, 3, 4, 5, 6, 7, 8, 9, 10, 11, 12 or 13.

Methods of Treating Neuritis Neuropathy by Administration of a CGRP Receptor Antagonist Neuritis is a general term for the inflammation of a nerve or inflammation of the peripheral nervous system. The causes for neuritis can include but are not limited to physical injury, vascular injury, toxin aging, a genetic disorder, infection (viral or bacterial), diphtheria, herpes zoster (shingles), leprosy, Lyme disease, chemical injury such as chemotherapy, radiation therapy, alcoholism, autoimmune disease, multiple sclerosis, Guillain-Barre syndrome, beri-beri (vitamin B1 deficiency), cancer, Celiac disease, diabetes (Diabetic neuropathy), hypothyroidism, porphyria, vitamin B12 deficiency and vitamin B6 excess. Types of neuritis can include but are not limited to brachial neuritis, cranial neuritis such as Bell's palsy, optic neuritis, and vestibular neuritis.

In another aspect, a method of treating neuritis is provided. The method comprises administering to the patient an effective amount of CGRP receptor antagonist or pharmaceutical salt thereof, as previously described.

The CGRP peptide antagonist can have the structure of Formula I, as described above. The CGRP antagonist can comprise an amino acid sequence having at least 80% sequence identity to the amino acid sequence of SEQ ID NOS: 1, 2, 3, 4, 5, 6, 7, 8, 9, 10, 11, 12, 13, 14 15, 57 or 58 wherein said peptide retains antagonist activity in these methods.

Dosages for the CGRP peptide antagonist for administration are previously described above. The CGRP peptide antagonist can be delivered alone or as a pharmaceutically acceptable salt thereof as described above.

The CGRP receptor antagonist is administered as previously described above. In some embodiments, the method further comprises monitoring or measuring a level of nerve activity function in said patient before, during or after administration of the effective amount of CGRP receptor antagonist. In some embodiments, the neuritis is from a physical injury, vascular injury, toxin aging, a genetic disorder, infection (viral or bacterial), diphtheria, herpes zoster (shingles), leprosy, Lyme disease, chemical injury such as chemotherapy, radiation therapy, alcoholism, autoimmune disease, multiple sclerosis, Guillain-Barre syndrome, beri-beri (vitamin B1 deficiency), cancer, Celiac disease, diabetes (Diabetic neuropathy), hypothyroidism, porphyria, vitamin B12 deficiency and vitamin B6 excess. Types of neuritis can include but is not limited to brachial neuritis, cranial neuritis such as Bell's palsy, optic neuritis or vestibular neuritis. In some embodiments the CGRP antagonist comprises a sequence set forth in SEQ ID NO: 1, 2, 3, 4, 5, 6, 7, 8, 9, 10, 11, 12, 13, 14, 15, 57 or 58.

Methods of Treating Glaucoma in a Patient

In another aspect, a method of treating glaucoma in a patient is provided. The method comprises administering to the patient in need an effective amount of CGRP receptor antagonist, as described above. The CGRP peptide antagonist can have the structure of Formula I, as described above.

Dosages and routes of administration for the CGRP peptide antagonist are as described above.

In some embodiments, the patient has diabetes. In some embodiments, the patient has been identified or selected to receive a drug for glaucoma. In some embodiments, the drug is a beta blocker, a prostaglandin, or an alpha-adrenergic agonist. In some embodiments, the CGRP receptor antagonist is administered in addition to or in combination with another drug such as a beta blocker, prostaglandin or α-adrenergic agonist. In some embodiments, the CGRP antagonist comprises a sequence set forth in SEQ ID NO: 1, 2, 3, 4, 5, 6, 7, 8, 9, 10, 11, 12, 13, 14, 15, 57 or 58. In some embodiments of the methods of treatment, the CGRP peptide antagonist is administered within a pharmaceutically acceptable formulation.

Methods of Reducing LDL Levels by Administration of a CGRP Receptor Antagonist

Low-density lipoprotein (LDL) is one of the five major groups of lipoprotein. These groups, from least dense to most dense, are chylomicrons, very low-density lipoprotein (VLDL), intermediate-density lipoprotein (IDL), low-density lipoprotein and high-density lipoprotein. The LDL particles can pose as a risk for cardiovascular disease when they invade the endothelium and become oxidized, since the oxidized forms are more easily retained by the proteoglycans. Increasing concentrations of LDL particles are strongly associated with increasing rates of accumulation of atherosclerosis within the walls of arteries over time, eventually resulting in sudden plaque ruptures and triggering clots within the artery opening, or a narrowing or closing of the opening, i.e. cardiovascular disease, stroke, and other vascular disease complications.

Familial hypercholesterolemia (FH) is a diagnosis of individuals with very significantly elevated low-density lipoprotein (LDL) cholesterol. FH is characterized by very high levels of LDL-C, as well as of total cholesterol. The condition greatly increases the risk of hardening of the arteries (atherosclerosis), which can lead to heart attacks, strokes and other vascular conditions. Individuals with FH have a 20-fold increased risk for coronary heart disease (CHD). Untreated men have a 50% risk of a nonfatal or fatal coronary event by age 50 years; untreated women have a 30% risk by age 60 years.

Borderline high LDL ranges from about 130 mg/dL to 159 mg/dL and about 160 to about 189 mg/dL is considered high. Any amount above 190 mg/dL is categorized as very high. In some embodiments, the patient has an LDL level of 130 mg/dL, 140 mg/dL, 150 mg/dL, 160 mg/dL, 170 mg dL, 180 mg/dL, 190 mg/dL, 200 mg/dL, or any concentration in between any aforementioned values.

PCSK9 is responsible for only a small percentage of FH cases. The normal PCSK9 gene codes for an enzyme that breaks down the cholesterol receptors after they have done their job. A mutation in this gene is unlike most mutations, which cause dysfunction of the affected gene. The PCSK9 mutation increases the gene's function, leading to too few remaining LDL receptors and thus an increase in the LDL cholesterol level. As PCSK9 is responsible for only a small percentage of both FH cases and for high LDL levels, there is need to provide other therapeutics to those suffering from high LDL levels.

In another aspect, a method of reducing LDL in a patient in need thereof is provided. The method comprises administering to the patient in need an effective amount of CGRP receptor antagonist, as described above. The CGRP peptide antagonist can have the structure of Formula I, as described above.

Dosages and routes of administration for the CGRP peptide antagonist are described above.

In some embodiments, the patient is suffering from high LDL concentration in the blood. In some embodiments, the patient has been identified or selected to receive a drug or therapy for controlling LDL levels. In some embodiments, the method further comprises monitoring or measuring the level or amount of LDL in said patient before, during, or after administration of the effective amount of CGRP receptor antagonist. In some embodiments, the therapy is administration for controlling LDL levels comprises statins, selective cholesterol absorption inhibitors, resins, bile acid sequestrant, bile acid-binding drugs or lipid lowering therapies. In some embodiments, the patient is already receiving therapy for lowering LDL levels. In some embodiments, the patient is a male. In some embodiments, the patient has familial hypercholesterolemia. In some embodiments the CGRP antagonist is a peptide comprising a sequence set forth in SEQ ID NO: 1, 2, 3, 4, 5, 6, 7, 8, 9, 10, 11, 12, 13, 14, 15, 57 or 58. In some embodiments of the methods of treatment, the CGRP peptide antagonist for administration is within a pharmaceutically acceptable formulation.

In some embodiments, the patient has an LDL level over 200 mg/dL. In some embodiments, the patient has an LDL level of 200 mg/dL, 220 mg/dL, 240 mg/dL, 260 mg/dL, 280 mg/dL or 300 mg/dL or any concentration in between any two aforementioned values. In some embodiments, the patient has an LDL level over 300 mg/dL.

ADDITIONAL EMBODIMENTS

Embodiment 1

Assessment of the Effect of a Peptide CGRP Receptor Antagonist (SEQ ID NO: 1) on Spontaneous Activity in C-Nociceptors in a Rat Model of Nerve Injury.

To investigate the effects of a CGRP receptor antagonist on pathological spontaneous activity in C-nociceptors the following experiments were performed on Sprague-Dawly rats. Crush-inducing sciatic neuropathy was produced in 12 male Sprague-Dawley rats. Spontaneous activity in injured C-nociceptors was then detected with microneurography and the response to CGRP receptor antagonist was assessed under unblind conditions. This study aimed to assess the effect of the CGRP receptor antagonist, on electrophysiological measures of spontaneous activity in subpopulations of injured C-nociceptors in a model of neuropathic pain, and to investigate the effects of the CGRP receptor antagonist on pathological spontaneous activity in peripheral C-nociceptors.

Material and Methods

All experiments were performed following government recommendations for the care and use of laboratory animals and were approved by the appropriate institutional committees for ethics in animal research.

As described herein, the experiment aimed to assess the effect of CGRP receptor antagonists, such as the antagonist set forth in SEQ ID NO: 1, on electrophysiological measures of spontaneous activity in subpopulations of injured C-nociceptors in a model of neuropathic pain.

Animals for Testing Spontaneous Nerve Behavior.

Experiments were performed in one group of 12 adult male Sprague-Dawley rats (Charles River, Laboratorios España, Barcelona, Spain) weighing 312±12 g (mean±SD (standard deviation)) on the day of the nerve injury. Rats underwent a quarantine period of 72 hours before the start of the experiments.

Animal Housing

Rats were housed in groups of three per cage. Cage cleaning was performed at least twice per week. Animals had rat food and tap water ad libitum. Animals were maintained under a standard light cycle (7:00 a.m.-7:00 p.m.), in a temperature and humidity controlled environment.

Experimental Model of Crush-Induced Sciatic Neuropathy

All surgical procedures were performed under general anesthesia (ketamine 90 mg/kg+xylazine 10 mg/kg i.p. (intraperitoneal)). The sciatic nerve was exposed at mid-thigh level. A standardized injury was produced by crushing the nerve three times in succession with a very fine point forcep at a constant point, 90 mm from the tip of the third digit. The wound was then sutured by layers and disinfected with povidone iodine. The animals received an analgesic subcutaneous (s.c). dose of buprenorphine and were maintained in a warm environment until full recovery from the anesthetic, and were allowed to recover from the nerve injury for a minimum of 70 days.

Administration of CGRP Receptor Antagonist

CGRP receptor antagonist (SEQ ID NO: 1) was dissolved according to manufacturer's instructions in saline solution, at a final concentration of 25 µg/Kg. Volumes of the intraperitoneal (i.p.) injected bolus ranged from 0.48 to 0.58 ml.

Microneurographic Recordings

Animals weighing 478±36 g (mean±SD) on the day of the recording were anesthetized with ketamine (90 mg/Kg) and xylazine (10 mg/Kg) injected i.p (intraperitoneal). Repeated administrations of one-half of the initial dose were performed as required to maintain the level of anesthesia, usually every hour.

The sciatic nerve was exposed at mid-thigh level, from the sciatic notch to the knee, and carefully freed from surrounding tissues. Animals were placed in prone position over a homeothermic Blanket (Harvard Apparatus, Holliston, Massachusetts, USA). Skin temperature was monitored with an infrared telethermometer pointing to the skin close to the receptive field of the nerve units under study. Upon completion of recording, rats were euthanized by an overdose of pentobarbital sodium injected i.p (Intraperitoneal).

Recordings of the sciatic nerve electrical activity were obtained inserting a tungsten microelectrode (FHC, Bow-doinham, ME, USA, nominal impedance 50-100KΩ, shaft Ø 175 µm (Ø=diameter)) into the sciatic nerve trunk with the aid of a micromanipulator. The recording electrode was carefully advanced into the nerve with the micromanipulator until characteristic neural audio signal could be heard. The method follows the same principles of the microneurographic technique employed in human patients.

The neural signals were first amplified with an isolated, high input impedance amplifier, band-pass filtered (maximum range 50-5000 Hz) and passed through a noise eliminator. The signal was then fed to an AM10 audio-monitor with noise clipper (Grass Technologies, Warwick, RI, USA) and to computers running separate software for collecting spontaneous and electrically evoked activity. Electrical stimuli were delivered to the cutaneous receptive field of the units by means of a constant current stimulator (DS7A, Digitimer, Welwyn Garden City, Hertfordshire, UK).

Electrical stimuli were triggered and the responses to electrical stimulation recorded and analyzed with a PC and PCI-6221M data acquisition board (National Instruments, Oklahoma City, Oklahoma, USA) running QTRAC software (©Institute of Neurology, London, UK). Spontaneous activity was digitized at 20 kHz and recorded continuously on one of the computers running LabChart software (PowerLab Systems, ADInstruments Ltd., Bella Vista, New South Wales, Australia). Analysis was performed with software written by Neuroscience Technologies, Science Park of Barcelona, Spain, to detect and quantify spontaneous activity.

Trigger pulses were delivered to the stimulator at different frequencies necessary to induce ADS of conduction velocity of the recorded C-fibers. The digitized responses were stored on computer as raw data for off-line analysis. Digital filtering (band-pass 0.3-2 kHz) and clamping of the baseline were performed both on-line and during off-line analysis for a better visualization of action potentials.

Action potentials recorded in the sciatic nerve were displayed as a raster plot of latencies. In the latency raster plots, each peak that exceeds a specified level is represented by a dot on a plot with latency as the ordinate and elapsed time as the abscissa. Depending on the level chosen, the dots could represent action potentials or noise. The raster plots presented herein display only selected units with adequate signal-to-noise, and each dot represents an identified single unit.

An action potential propagated in an unmyelinated axon causes long-lasting (up to a few minutes) activity-dependent slowing (ADS) of conduction velocity. The ADS of the recorded C-fibers was assessed using a modified protocol described by (Serra et al., 1999; incorporated by reference in its entirety herein). This consists of a sequence of 5 steps: 1) 3 min baseline stimulation at 0.25 Hz; 2) 3 min pause (0 Hz); 3) 3 min at 0.25 Hz; 4) 3 min 2 Hz train; and 5) return to 0.25 Hz baseline until the latencies return to their original values. This stimulation method allows differentiation of profiles of ADS of conduction velocity in individual C-fibers that correspond to specific functional types of peripheral nerve fibers:

Type 1: slow progressively (average latency increase of 28.3% at 2 Hz) and correspond to nociceptors. Nociceptors were subdivided into:

Type 1A: essentially unaffected by the stimulation pause, correspond to the mechano-sensitive nociceptor.

Type 1B nociceptors show an appreciable reduction in latency at the end of the pause and correspond to the mechano-insensitive nociceptor.

Type 2: fibers slow to reach a plateau within 1 min of stimulation at 2 Hz (average latency increase 5.2%) and are specific cold receptors.

Type 3: essentially unaffected by the stimulation at 2 Hz (slowing >3%); their function remains unclear (a recent report suggested that they probably represent the population of low-threshold mechano-sensitive C-fibers).

Type 4: fibers slow to reach a plateau, partially recover conduction velocity during the 2 Hz period, and correspond to efferent sympathetic fibers.

Only identified nociceptor units were examined in this study. Conduction velocity was estimated by dividing the conduction distance by the baseline latency at the stimulation rate of 0.25 Hz.

Some C-nociceptors in rat neuropathic pain models exhibit abnormal sudden shifts in baseline latency due to ongoing spontaneous activity. Correlation with raster plots has shown that bursts of spontaneous activity are followed by transient ADS (activity dependent slowing) giving a 'saw tooth' appearance to the latency profile, identical to that previously described in patients with neuropathic pain.

After the identification of C-fiber types, having assessed spontaneous activity in at least one fiber and in order to test the effect of the CGRP receptor antagonist on C-nociceptors, the last step of the protocol described above was extended as follows:

1. 60 min return to 0.25 Hz baseline
2. CGRP antagonist administration
3. 60-90 min of constant 0.25 Hz baseline stimulation to assess possible effects of the compound.

In the spontaneous C-nociceptors that were recorded, the following measurements were made:

1. Significant Latency Increase (SLI): any departure from baseline >300 µs (cut-off for latency fluctuations caused by spontaneous activity). SLI were expressed as SLI/min. It is a measure of how many times the unit has engaged in spontaneous activity of at least 2 extra action potentials.
2. Total Increase (TI): Σ of % increase of all SLI in a given unit of time. TI was expressed as TI/min, and it represents a direct estimate of the total number of extra spikes that have occurred per unit of time.

Baseline measurements were recorded during a 60 minute period immediately before drug administration. Post-treatment recording lasted for 60-90 min. The analysis of the effect of treatment on spontaneous activity was performed by comparing baseline activity (BT) with the effect after treatment (AT) in 10 min bins, until the end of the recording (BT=baseline activity−before activity).

Statistical Analysis

Analysis of statistical differences was performed using the software package Prism 5.1 (GraphPad Software, Inc., La Jolla, California, USA). P values of less than 0.05 were considered statistically significant. The paired Student t-test was used to compare the means of two matched groups.

Results

Demographics of the Studied Population

A total of 12 rats were used in the present study. Table 1 details the number of animals, rat ID (identification code), body weight on the day of the microneurography recording and days of maturation after induction of the crush. All the rats received the treatment and all the recordings were analyzed.

TABLE 1

Description of the 12 rats used in the investigation of the effects of the CGRP receptor antagonist on pathological spontaneous activity in peripheral C-nociceptors.

| animal ID | Rat code | weight micro | maturation days |
|---|---|---|---|
| 1 | C341 0-1 | 44 | 70 |
| 2 | C342 0-0 | 43 | 72 |
| 3 | C343 1-0 | 50 | 72 |
| 4 | C343 0-1 | 49 | 72 |
| 5 | C344 0-0 | 50 | 73 |
| 6 | C344 0-1 | 52 | 73 |
| 7 | C344 1-0 | 44 | 76 |
| 8 | C345 0-1 | 47 | 76 |
| 9 | C346 1-0 | 46 | 72 |
| 10 | C346 0-0 | 50 | 72 |
| 11 | C347 0-0 | 49 | 73 |
| 12 | C347 0-1 | 58 | 73 |

Number and Functional Subtypes of Recorded C-Fibers

From the 12 analyzed rats, a total of 42 C-fiber units were identified. As described in rats and humans, there was a predominance of C-nociceptors and sympathetic fiber types. Measures of activity-dependent slowing were obtained from all fiber types, but only C-nociceptor types were further analyzed. Distribution of fiber subclasses and relative percentages are detailed in Table 2.

TABLE 2

Total number of C-fibers analyzed in the study, with relative distribution of functional subclasses.

| Functional class | N | % total |
|---|---|---|
| Nociceptor | 35 | 83.33 |
| Type 1A | 6 | 14.29 |
| Type 1B | 27 | 64.29 |
| Type 1 | 2 | 4.76 |
| Type 2 & 4 | 6 | 14.29 |
| Type 3 | 1 | 2.38 |
| TOTAL | 42 | 100 |

Type 1A: Mechano-sensitive C-nociceptor; Type 1B: Mechano-insensitive C-nociceptor; Type 1: undetermined class of C-nociceptor; Type 2: cold C-thermoreceptor; Type: 3 unknown function; Type 4: sympathetic efferent.

There was a clear predominance of type 1B nociceptors over all the other types of fibers. There was an even distribution of recorded C-nociceptor types among different animals, and there was no particular animal with an over-representation of spontaneous fibers.

Only spontaneous activity in C-nociceptors, which is always a pathological phenomenon, was subsequently analyzed.

Spontaneous Activity in C-Nociceptors

Shown in FIG. 1 is a raster plot of a spontaneous C-fiber before and after the CGRP receptor antagonist administration. From the 35 nociceptors analyzed, 14 of them displayed spontaneous activity (33.33% from the total fibers), and all of them were of type 1B. This selectivity has recently been described in several neuropathic pain conditions, both in humans and animals. As shown in FIG. 1, the action potentials recorded in the sciatic nerve had virtually no excitation observed after introduction of the CGRP receptor antagonist. Thus, CGRP antagonist (SEQ ID NO: 1), led to the surprising effect of preventing further spontaneous activity in the C-fibers.

Figure 2A:
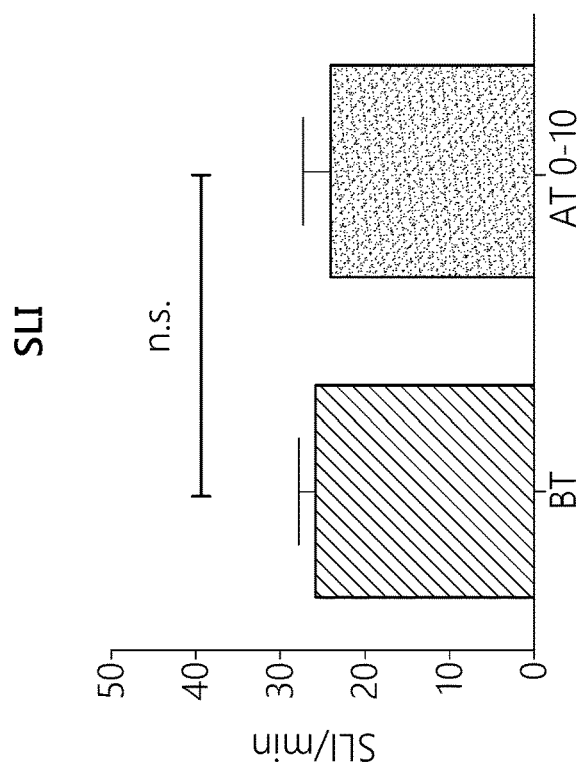
FIGS. 2A and 2B show an analysis of the spontaneous activity before and after the CGRP receptor antagonist administration.
Figure 2B:
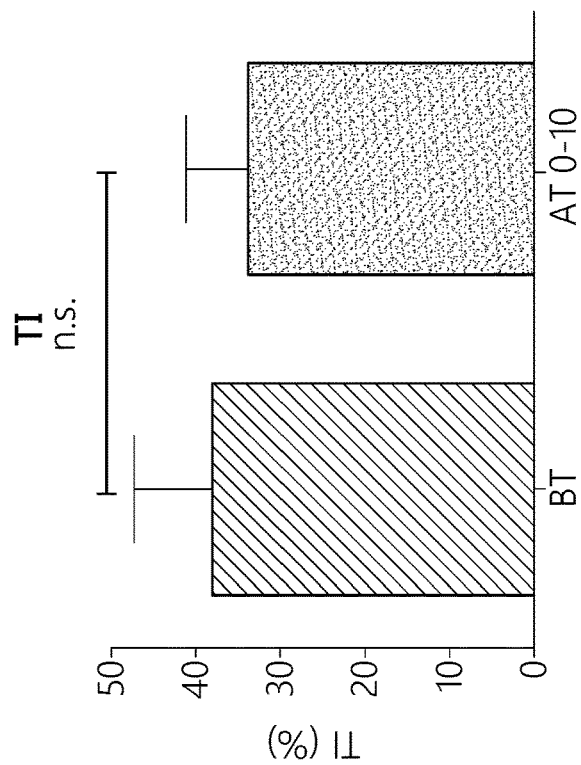
Figure 3A:
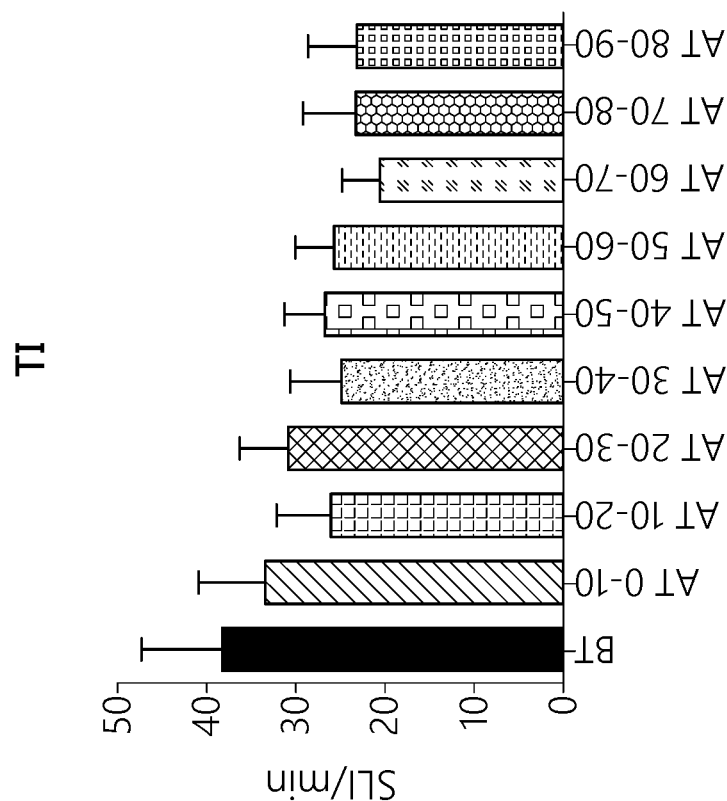
FIGS. 3A and 3B show an analysis of the spontaneous activity after the CGRP receptor antagonist administration. As shown is a comparison of two measurements of spontaneous activity, SLI/10 min (FIG. 3A) and TI (%) (FIG. 3B), obtained for each 10 minute bins throughout the 90 min after the drug administration.
Figure 3B:
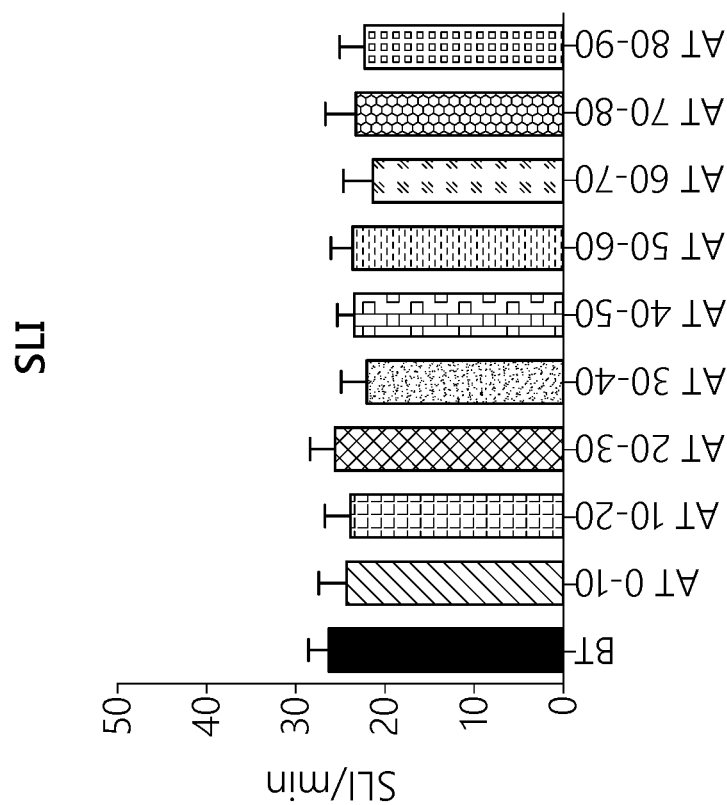

The immediate effect of the CGRP receptor antagonist is shown in FIGS. 2A and 2B. The analysis of SLI (Significant Latency Increase) and TI (Total Increase) did not reveal a statistically significant effect on the spontaneous activity of C-nociceptors during the first 10 min after administration. The same analysis was done for the rest of the recording and the results are shown in FIGS. 3A and 3B.

Morbidity and Mortality

All the rats studied were in good condition during the whole procedure and were sacrificed at the end of the experiment.

Conclusions

The peripheral neuropathy commonly induces spontaneous activity in type 1B C-nociceptors, which is the substrate of the experience of spontaneous burning and deep aching pain in patients with peripheral neuropathy.

As the CGRP peptide antagonist has only been used for vasodilation studies, the function of CGRP peptide antagonist was investigated for its role in nerve function as CGRP receptors can also be located in neurons.

In this study there was less spontaneous activity at long intervals after the administration of a CGRP antagonist compound.

Embodiment 2: The Use of CGRP Antagonist in Rat Experimental Glaucoma Model

Ganglion cells of the retina and the optic nerve are the major sites of damage in glaucoma. The initial insult can be several possibilities such as a gene mutation, increased intraocular pressure, or oxidative insult, in which all can lead to ganglion cell apoptosis, a natural but usually quiescent pathway that, when activated, leads to cell death. The sick, injured, or stressed cell essentially "commits suicide." Vision researchers have now worked out many of the steps in the apoptotic pathway in ganglion cells and can begin to test inhibitors that can block the pathway and thus at least slow ganglion cell dysfunction and death.

A purpose of this study was to investigate neuroprotective properties of CGRP antagonist in a rat experimental glaucoma model.

In this study, Wistar rats (n=12) were used for the experiments. The neuroprotective properties of compounds were investigated in a rat laser model of glaucoma. Rats were divided into two groups of six rats each. One group served as a placebo control receiving vehicle (NaCl) injections, and the other was treated with a peptide CGRP receptor antagonist (SEQ ID NO: 1). For all 12 rats, the contralateral, untreated eye served as a naïve undiseased control. The vehicle control and test compound (20 mg/kg) were administered systemically (IP) daily for the whole follow-up period of two weeks. The animals were sacrificed using transcardial perfusion. The retinal whole-mounts were then immuno-stained against retinal ganglion cell (RGC) marker Brn3a and astrocytic marker GFAP (glial fibrillary acidic protein). The number of Brn3a positive profiles was manually counted from retinal images taken from central and peripheral parts of retina. The total number of GFAP-immunoreactive cells (retinal astrocytes) was estimated using stereology. The total number of RGC axons in the optic nerve was estimated using stereology.

The results from the experiments show that the number of Brn3a positive cells decreased by approximately 20% in the vehicle treatment group, and increased by approximately 3% in the CGRP antagonist treatment group as compared to naïve eye. Similarly, the total number of optic nerve axons was decreased by 18% in the vehicle group and increased by 1.7% in the CGRP antagonist treated group as compared to optic nerves from contralateral control eyes. There were no differences in the total number of retinal astrocytes between the groups.

Conclusions: Although CGRP antagonists have been implicated in treatment of migraines and in modulating CGRP-induced vasodilation, the systemic administration of a CGRP antagonist in a rat glaucoma model surprisingly showed neuroprotection, an unrelated effect of vasodilation, at both cellular and optic nerve axon levels. Additionally, treatment with a CGRP antagonist surprisingly showed an increase in the number of Brn3a positive cells in the retinal images, as well as an increase in the number of optic nerve axons, evidencing neurodegeneration.

Animals for the Glaucoma Study

All animals were treated in accordance with the ARVO Statement for the Use of Animals in Ophthalmic and Vision Research and the EC Directive 86/609/EEC for animal experiments, using protocols approved and monitored by the Animal Experiment Board of Finland (Experimentica Ltd. animal license number ESAVI/219/04.10.07/2014).

Rat Laser Model of Episcleral Vein Photocoagulation

The rat glaucoma model was induced unilaterally by laser photocoagulation of episcleral veins as previously described (Kalesnykas et al., 2007). Anesthesia was performed using sodium pentobarbital (30 mg/kg). The contralateral eye served as the control. Wistar rats (n=12) (Laboratory Animal Center, University of Eastern Finland, Kuopio, Finland) were used. The following efficacy measures were tested:

1. Quantification of Brn3a and GFAP-positive cells from retinal whole mounts manually and using stereology.

2. Quantification of optic nerve axons using stereology.

Treatment Administration

Following surgery to induce glaucoma, CGRP antagonist (SEQ ID NO: 1) (20 µg/kg each) or vehicle control (NaCl) was administered intraperitoneally (IP), on a daily basis for two weeks following glaucoma induction surgery.

Animal Sacrifice and Tissue Collection

At the end of the study/follow-up period, the animals were sacrificed by transcardial perfusion using 4% paraformaldehyde in 0.1M phosphate buffer, pH 7.4. The brains, eyes and optic nerves were collected and the retinal whole mounts were prepared for immunohistochemical staining.

Morphological Assessment of Retinal Whole Mounts

Retinal whole mounts were immuno-stained against RGC (Brn3a) and astrocytic (GFAP) antibodies and the number of cells was quantified either manually (Brn3a) or as previously described (Kalesnykas et al., 2008).

Morphological Assessment of Optic Nerve Axons

Semi-thin sections (1 µm-thick) of optic nerves were prepared and the total number of axons were estimated as previously described (Kalesnykas et al., 2012; Ragauskas et al., 2014).

Results

Animals

The baseline weight of animals and the weight of animals prior the sacrifice in each treatment group are presented in Table 3.

TABLE 3

The weight of animals at the baseline and at the end of the study.

| Group | CGRP antagonist | Vehicle Control (NaCl) |
|---|---|---|
| Baseline weight, g | 538 ± 21 | 603 ± 108 |
| Weight prior to sacrifice, g | 524 ± 27 | 574 ± 93 |

Data are expressed as mean ± SD.

There was no significant difference in the weight between the groups (Mann-Whitney U test, P>0.05).

The Number of RGCs

The retinas were immuno-stained against RGC specific antibody Brn3a, retinas were imaged and Brn3a positive profiles were counted manually using Image J software (NIH, Bethesda, Maryland, USA). Rat no. 4 (treatment group with the CGRP antagonist) was excluded from the final analyses.

Figure 4B:
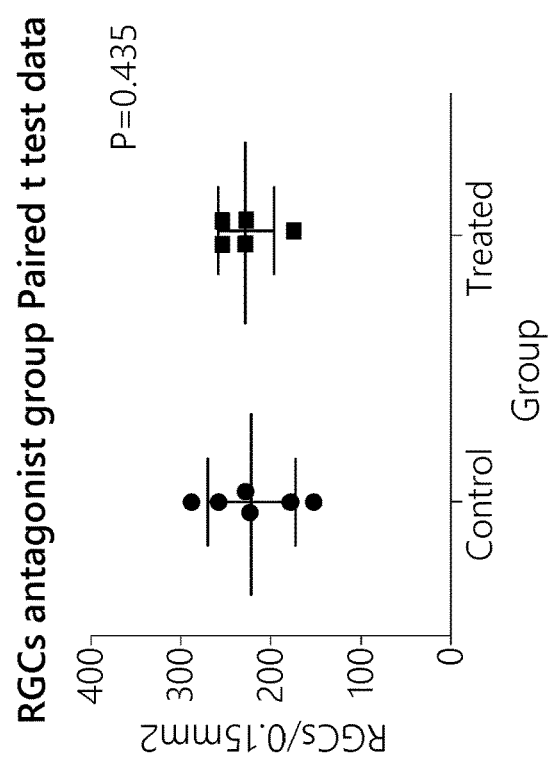
FIGS. 4A and 4B show the measurement of the number of RGCs (Retinol ganglion cells).
Figure 4A:
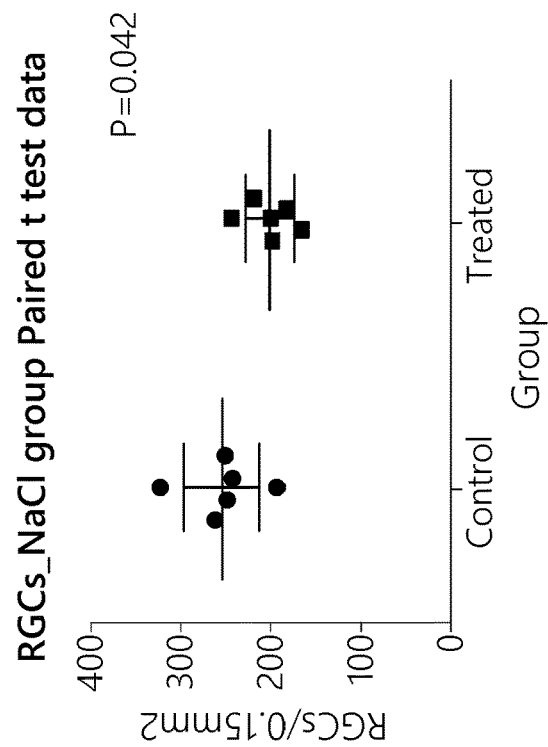

As shown in FIG. 4A, the number of Brn3a positive profiles significantly decreased by 20.3% in the lasered eyes from the vehicle group as compared to contralateral control eyes (paired sample t-test, P=0.042).

As shown in FIG. 4B, the number of Brn3a positive cells increased by 3.0% (P=0.43) in the CGRP antagonist treated group.

The Total Number of Optic Nerve Axons

The total number of optic nerve axons were estimated from 1-µm-thick sections using StereoInvestigator software (MicroBrightfield Inc., Williston, Vermont, USA.

Figure 5B:
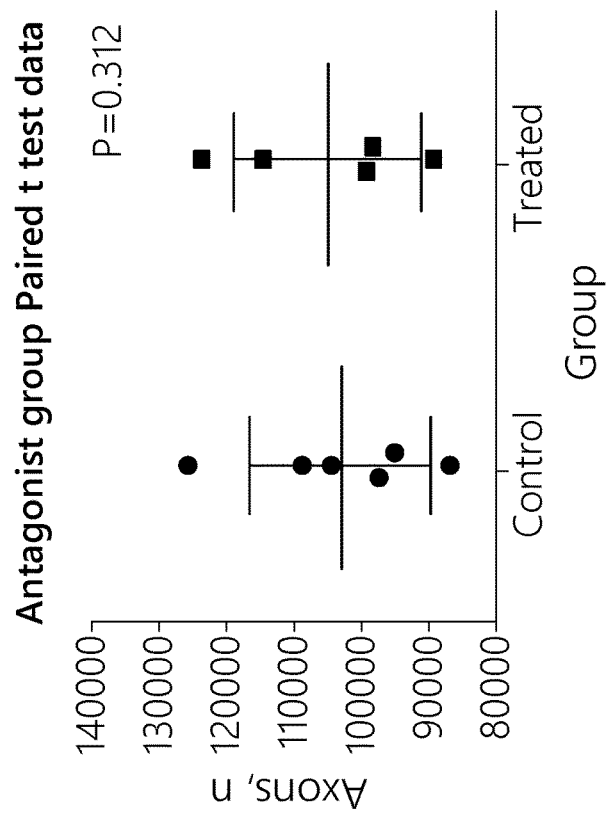
FIGS. 5A and 5B show the experimental data for experiments in which the total number of optic nerve axons were accessed.
Figure 5A:
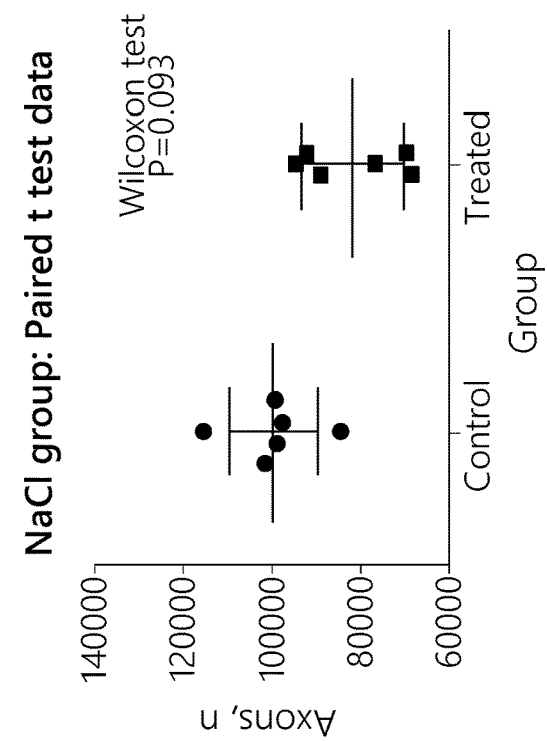

As shown in FIG. 5A, the total number of optic nerve axons was decreased between lasered and contralateral control eyes in the vehicle treatment group. In contrast, the CGRP antagonist group showed a slight increase (FIG. 5B) in the total number of axons as compared to contralateral control eyes (paired sample t-test, P>0.05 in both groups).

Materials and Methods

Processing, Staining and Stereology on Optic Nerve Axons

After the optic nerves were post-fixed in 4% PFA (in 0.1M phosphate buffer, pH 7.4) solution, they were placed in 1% osmium, dehydrated in ascending alcohol concentration and placed in 1% uranyl acetate in 100% ethanol for 1 hour (Cone et al., 2012). Then the optic nerves were embedded in epoxy resin mixture at 60° C. for 48 hours and semi-thin sections (1 µm-thick) of optic nerves were cut (Cone et al., 2012). The total number of axons was estimated using optical fractionator method as previously described (Ragauskas et al., 2014). Briefly, axons were counted manually using the Stereo Investigator software (MicroBrightField, VT, USA). First, the optic nerve section was outlined using CFI Plan Achro 4× objective (N.A. 0.1, W.D. 30). Thereafter, a CFI Plan Fluor 100× oil immersion objective (N.A. 1.30, W.D. 0.20) was used for axon counting.

Immunohistochemistry and Retinal Whole Mount Stereology

Retinal whole mounts were immuno-stained against RGC specific marker Brn3a (dilution 1:1,000; MAB1585, lot no. 2557607; Chemicon, Hayward, California, USA) and GFAP (1:1000; Dako, z0334, lot no. 20005461). The following secondary antibodies were used: goat anti-mouse Alexa Fluor 488 (1:250, A11001, lot no. 1572559; Life Technologies, San Diego, California) and goat anti-rabbit Alexa Fluor 594 (1:250 A11037, lot no. 1588554; Life Technologies, San Diego, California). DAPI (1:1,000, D9542, lot no. 034M4031V; Sigma, St. Louis Missouri, USA) was used as counterstain.

Data Analysis

Quantitative data was graphed, analyzed and presented as mean±standard deviation (SD) or standard error of mean (SEM). Parametric data was analyzed using paired-samples T-test (the contralateral eye of the same animal serves as control). Non-parametric data was analyzed using Mann-Whitney U test (comparison of 2 groups) or Wilcoxon paired-samples T-test. For cell counts, assuming a Gaussian distribution of the data, any data point 2 standard deviations from the columnar mean was excluded. The differences are considered to be statistically significant at the P<0.05 level.

The results show that the number of Brn3a positive cells decreased by approximately 20% in the vehicle treatment group, and increased by approximately 3% in the CGRP antagonist treatment group as compared to naïve eye. Similarly, the total number of optic nerve axons was decreased by 18% in the vehicle group, and increased by 1.7% in the CGRP antagonist treatment group as compared to optic nerves from contralateral control eyes. There were no differences in the total number of retinal astrocytes between the groups.

Conclusion

Systemic administration of a peptide CGRP antagonist in a rat glaucoma model unexpectedly showed neuroprotection both at cellular and optic nerve axon levels.

Embodiment 3. Assessment of the Effect of CGRP Receptor Antagonist Administration on the Levels of LDL in Rats Familial hypercholesterolemia (FH) is a genetic disorder that is characterized by high cholesterol levels, specifically very high levels of low-density lipoprotein (LDL) in the blood, and early cardiovascular disease. Individuals with FH can have high cholesterol levels that are less responsive to standard methods of treatment used to control cholesterol levels. Without being limiting, these types of treatments include statins, selective cholesterol absorption inhibitors, resins (bile acid sequestrants or bile acid-binding drugs) and lipid-lowering therapies. Nevertheless, treatment (including higher statin doses) and lifestyle changes are the standard of treatment employed for patients with FH.

Study

In the course of a routine study of a peptide CGRP antagonist (SEQ ID NO: 1) to evaluate off-target effects of the compound, it was discovered that the test compound advantageously lowered LDL concentrations in blood.

Experimental Summary

Sprague Dawley rats were administered the CGRP antagonist daily via the subcutaneous route for a period of 14 days, resulting in the surprising effect of LDL lowering. Fifty six animals (36 males and 20 females) were distributed into four groups (consisting each of 5 males and 5 females per group and 4 extra males each for testing group as backups). The groups were as follows: G1—Control, G2—Low dose—100 mcg/kg, G3—Intermediate dose—300 mcg/kg, G4—High dose—1000 mcg/kg.

Rats from the treatment groups were dosed subcutaneously with CGRP receptor antagonists (SEQ ID NO: 1) reconstituted with normal saline at different dose levels per treatment group for 14 days. Control animals were dosed with the vehicle alone.

There was no mortality or morbidity and no clinical signs were observed during the entire study period except for four males from the high dose group that showed lethargy on day 10. Out of these four animals, three animals continued showing lethargy on day $11^{th}$ but all animals normalized from day 12.

The food consumption was normal for all the animals from all study groups. Similarly no statistically significant difference was observed in body weight among the groups.

Experimental Procedures

Test System Details/Characterization.

The species used for the studies were of the species Rattus norvegicus (Rat), and strain Sprague Dawley, from the Palamur Biosciences Pvt. Ltd. The weight variation at the time of dosing was about ±20% of mean body weight of each sex. The age at the time of dosing was about 10-12 weeks. The male and female rats were nulliparous and non-pregnant. The number of animals was 56 rats (36 male plus 20 females). 4 male rats were used as extras for each group (total 16) for randomization and animal replacement during acclimatization. Thus, the number of animals per group was 9 males and 5 females.

The acclimatization period was, at a minimum, 7 days. For the randomization, animals were selected and grouped based on stratified randomization by using body weights one day before dosing (day 0) using an Excel program. The route of administration of the antagonist was by a subcutaneous method. The frequency of the administration was daily for fourteen days. The dose volume was set at 5 ml/kg of body weight. The duration of the treatment was fourteen days with administration occurring approximately at the same time each day.

The animals were housed at a temperature of 20.1 to 22.7° C. with a relative humidity of 49 to 59%. The animals were at a photo period or exposure of 12 hours of light and 12 hours of dark. The room air exchanges were at a minimum of 10-15 air exchanges per hour. For caging, the animals were housed in groups in poly propylene rat cages with paddy husk bedding. The bedding material was changed daily. The animals were identified with cage cards and assigned animal identification numbers. The diet of the rats consisted of Amrut rodent feed and RO water, which was provided ad libitum.

Preparation and Administration of Test Item

While preparing the dose formulation, required quantities of test item (i.e. CGRP antagonist) was weighed separately. The required volume of normal saline was added to the test item. A clear solution was obtained after addition of normal saline to test item. The test item was administered subcutaneously at the desired dose level once daily for up to 14 days. Homogeneity of the test item in the vehicle was maintained during administration.

Observations

The following observations were recorded:
1. Clinical Signs

All animals were observed for any visible clinical signs including changes in fur, eyes, occurrence of secretions, excessive grooming, self-mutilation, lacrimation, piloerection, pupil size, changes in gait, posture and response to handling and convulsions.

2. Body Weight

Body weight was recorded on day 1, 7, 11 and 15.

3. Feed Consumption

Feed consumption was recorded daily and reported weekly.

4. Blood Collection and Laboratory Investigations

Blood samples for were collected from all animals on day 15. The animals were fasted overnight before blood sampling but allowed access to water ad libitum for hematology and biochemistry. Blood samples were drawn from the retro-orbital plexus using a micro-hematocrit heparinized glass capillary tube. Blood samples were centrifuged (3500 rpm) and after centrifugation plasma was separated for further analysis.

The following time windows for blood collection were not considered as deviation: ±1 minute for 0.25 hour, ±2 minutes for 0.5 hour and ±5 minutes for 1 to 8 hours and ±15 minutes for 24 hours.

Clinical Biochemistry

Total Cholesterol, Triglycerides, Low-density lipoprotein and High-density lipoprotein parameters are shown in Tables 4 and 5, for male and female rats, respectively. Data from the LDL analysis is shaded. Other non-cholesterol related parameters measured are not shown, but none were significantly different from control.

TABLE 4

Summary of Clinical biochemistry parameters at day 15 in male rats.

| GROUP/DOSE | T. Chol (mg/dL) | Trig (mg/dL) | HDL (U/L) | LDL (U/L) |
|---|---|---|---|---|
| G1 - Control | 78.40 ± 12.18 | 69.00 ± 22.28 | 50.40 ± 8.17 | 14.20 ± 7.49 |
| G2 - 100 mcg/kg b.w. | 78.00 ± 20.95 | 121.40* ± 43.48 | 51.60 ± 13.81 | 2.96 ± 1.16 |
| G3 - 300 mcg/kg b.w. | 69.60 ± 10.55 | 97.20 ± 22.79 | 46.00 ± 6.89 | 4.16 ± 0.85 |
| G4 - 1000 mcg/kg b.w. | 58.20 ± 9.63 | 82.40 ± 23.20 | 37.00 ± 5.52 | 4.72 ± 2.32 |

Data are expressed as Mean ± S.D.(n = 5).
T. chol.—Total Cholesterol, Trig—Tryglycerides, LDL—Low-density lipoprotein, HDL—High-density lipoprotein.

TABLE 5

Summary of Clinical biochemistry parameters at day 15 in female rats.

| GROUP/DOSE | T. Chol (mg/dL) | Trig (mg/dL) | HDL (U/L) | LDL (U/L) |
|---|---|---|---|---|
| G1 - Control | 69.80 ± 13.70 | 61.60 ± 19.40 | 49.20 ± 9.44 | 8.28 ± 6.01 |
| G2 - 100 mcg/kg b.w. | 84.20 ± 25.56 | 70.60 ± 17.11 | 59.00 ± 15.36 | 11.08 ± 8.43 |
| G3 - 300 mcg/kg b.w. | 91.00 ± 25.05 | 84.00 ± 18.68 | 61.60 ± 15.90 | 12.60 ± 8.26 |
| G4 - 1000 mcg/kg b.w. | 80.60 ± 15.40 | 82.00 ± 28.48 | 54.80 ± 9.34 | 9.40 ± 5.78 |

Data are expressed as Mean ± S.D.(n = 5).
T. chol.—Total Cholesterol, Trig—Tryglycerides, LDL—Low-density lipoprotein, HDL—High-density lipoprotein, Lowering of LDL Levels in Rats As shown, the administration of a CGRP receptor antagonist, led to the surprising effect of decreasing LDL levels in rats. As shown in Tables 4 and 5, the substantial LDL lowering can be seen especially in the male rats and at every test dose administered (100 to 1000 mc/kg b.w).

Conclusion

Systemic administration of a peptide CGRP antagonist surprisingly showed a metabolic effect, by lowering the LDL levels in normal rats.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those of skill within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

Any of the features of an embodiment of the first through twelfth aspects is applicable to all aspects and embodiments identified herein. Moreover, any of the features of an embodiment of the first through twelfth aspects is independently combinable, partly or wholly with other embodiments described herein in any way, e.g., one, two, or three or more embodiments may be combinable in whole or in part. Further, any of the features of an embodiment of the first through twelfth aspects may be made optional to other aspects or embodiments.

REFERENCES

1. Ashina M, Bendtsen L, Jensen R, Schifter S, Olesen J. Evidence for increased plasma levels of calcitonin gene-related peptide in migraine outside of attacks. Pain. 2000 May; 86(1-2):133-8.
2. Bundgaard, H. ed., 1985 *Design of Prodrugs*, Elsevier Science Publishers, Amsterdam.
3. Castel D, Sabbag I, Brenner O, Meilin S. Peripheral Neuritis Trauma in Pigs: A Neuropathic Pain Model. J Pain. 2016 January; 17(1):36-49.
4. Chader G J, Key needs and opportunities for treating glaucoma. Invest Ophthalmol Vis Sci. 2012 May 4; 53(5): 2456-60.
5. Christopoulos G, Perry, K J, Morfis M, Tilakaratne, N, Gao Y, Fraser N J, Main M J, Foord S M, and Sexton P M. Multiple Amylin Receptors Arise from Receptor Activity-Modifying Protein Interaction with the Calcitonin Receptor Gene Product. Mol Pharmacol. 1999 July; 56(1):235-42.
6. Cone F E, Steinhart M R, Oglesby E N, Kalesnykas G, Pease M E, Quigley H A (2012) The effects of anesthesia, mouse strain and age on intraocular pressure and an improved murine model of experimental glaucoma. Exp Eye Res. June; 99:27-35.
7. Edvinsson L. 2001, CNS Drugs 15(10):745-53; Williamson, D. J. 2001 *Microsc. Res. Tech.* 53:167-178.
8. Gallai V1, Sarchielli P, Floridi A, Franceschini M, Codini M, Glioti G, Trequattrini A, Palumbo R. Vasoactive peptide levels in the plasma of young migraine patients with and without aura assessed both interictally and ictally. Cephalalgia. 1995 October; 15(5):384-90.
9. Goadsby P J1, Edvinsson L, Ekman R. Vasoactive peptide release in the extracerebral circulation of humans during migraine headache. Ann Neurol. 1990 August; 28(2):183-7.
10. Grant, A D, 2002, *Brit. J Pharmacol.* 135:356-362
11. Gupta, N., and Yucel, Y. H., 2007, Glaucoma as a neurodegenerative disease. Current Opin. Ophthalmol 18:110-114.
12. Hay D L, Smith D M., Knockouts and transgenics confirm the importance of adrenomedullin in the vasculature. Trends Pharmacol Sci. 2001 February; 22(2):57-9.
13. Kalesnykas G, Oglesby E N, Zack D J, Cone F E, Steinhart M R, Tian J, Pease M E, Quigley H A (2012) Retinal ganglion cell morphology after optic nerve crush and experimental glaucoma. Invest Ophthalmol Vis Sci 53(7):3847-3857.
14. Kalesnykas G, Uusitalo H (2007) Comparison of simultaneous readings of intraocular pressure in rabbits using Perkins handheld, Tono-Pen XL, and TonoVet tonometers. Greafes Arch Clin Exp Ophthalmol 245: 761-762.
15. Kalesnykas G, Tuulos T, Uusitalo H, Jolkkonen J (2008). Neurodegeneration and cellular stress in the retina and optic nerve in rat cerebral ischemia and hypo perfusion models. Neuroscience, 155(3):937-47.
16. Lassen L H, Aderslev P A, Jacobsen V B, Iversen H K, Sperling B, Olesen J. CGRP may play a causative role in migraine. Cephalalgia. 2002 February; 22(1):54-61.
17. Marquest de Prado B, Russo A F. CGRP receptor antagonists: A new frontier of anti-migraine medications Drug Discov Today Ther Strateg. 2006 Winter; 3(4): 593-597.
18. McLatchie L M, Fraser N J, Main M J, Wise A, Brown J, Thompson N, Solari R, Lee G M and Foord S M. RAMPs regulate the transport and ligand specificity of the calcitonin-receptor-like receptor. *Nature* 393, 333-339 (28 May 1998).
19. Mimeault M1, Quirion R, Dumont Y, St-Pierre S, Fournier A. Structure-activity study of hCGRP8-37, a calcitonin gene-related peptide receptor antagonist. J Med Chem. 1992 Jun. 12; 35(12):2163-8.
20. Miret J J, Rakhilina L, Silverman L and Oehlen B. Functional Expression of Heteromeric Calcitonin Gene-related Peptide and Adrenomedullin Receptors in Yeast. J Biol Chem. 2002 Mar. 1; 277(9):6881-7. Epub 2001 Dec. 3.
21. Moskowitz M A, Neurogenic versus vascular mechanisms of sumatriptan and ergot alkaloids in migraine. Trends Pharmacol Sci. 1992 August; 13(8):307-11.
22. Mufson E J, Counts S E, Che S, Ginsberg S D. Neuronal gene expression profiling: uncovering the molecular biology of neurodegenerative disease. Progress in Brain Research Volume 158, 2006, Pages 197-222.
23. Mulder H, Gebre-Medhin S, Betsholtz C, Sundler F, Ahrén B. Islet amyloid polypeptide (amylin)-deficient mice develop a more severe form of alloxan-induced diabetes. Am J Physiol Endocrinol Metab. 2000 April; 278(4):E684-91.
24. Nafissi N, Foldvari M, Neuroprotective therapies in glaucoma: II. Genetic nanotechnology tools, Front Neurosci. 2015; 9: 355.
25. Poyner D R. Calcitonin gene-related peptide: multiple actions, multiple receptors. Pharmacol Ther. 1992; 56(1): 23-51.
26. Poyner D R, Sexton P M, Marshall I, Smith D M, Quirion R, et al. International Union of Pharmacology. XXXII. The mammalian calcitonin gene-related peptides, adrenomedullin, amylin, and calcitonin receptors. Pharmacol. Rev. 2002; 54:233-46
27. Ragauskas S, Leinonen H, Puranen J, Rönkkö S, Nymark S, Gurevicius K, Lipponen A, Kontkanen O, Puoliväli J, Tanila H, Kalesnykas G (2014). Early retinal function deficit without prominent morphological changes in the R6/2 mouse model of Huntington's disease. PLoS One. 3; 9(12):e113317. doi:10.1371/journal.pone.0113317.
28. Ragauskas S, Leinonen H, Puranen J, Ronkko S, Nymark S, Gurevicius K, Lipponen A, Kontkanen O, Puolivali J, Tanila H, Kalesnykas G (2014). Early retinal function deficit without prominent morphological changes in the R6/2 mouse model of Huntington's disease. PLoS One. 3; 9(12):e113317. doi:10.1371/journal.pone.0113317.
29. Roh J, Chang C L, Bhalla A, Klein C and Teddy Hsu S Y T. Intermedin Is a Calcitonin/Calcitonin Gene-related Peptide Family Peptide Acting through the Calcitonin Receptor-like Receptor/Receptor Activity-modifying Protein Receptor Complexes. J Biol Chem. 2004 Feb. 20; 279(8):7264-74. Epub 2003 Nov. 13.
30. Rovero P1, Guliani S, Maggi C A. CGRP antagonist activity of short C-terminal fragments of human alpha CGRP, CGRP(23-37) and CGRP(19-37). Peptides. 1992 September-October; 13(5):1025-7.
31. Russo A F, CALCITONIN GENE-RELATED PEPTIDE (CGRP): A New Target for Migraine, *Annu Rev Pharmacol Toxicol*. 2015; 55: 533-552. doi:10.1146/annurev-pharmtox-010814-124701
32. Salmon A M, Damaj I, Sekine S, Picciotto M R, Marubio L, Changeux J P. Modulation of morphine analgesia in alpha CGRP mutant mice. Neuroreport. 1999 Mar. 17; 10(4):849-54.
33. Salmon A M, Damaj M I, Marubio L M, Epping-Jordan M P, Merlo-Pich E, Changeux J P. Altered neuroadaptation in opiate dependence and neurogenic inflammatory nociception in alpha CGRP-deficient mice. Nat Neurosci. 2001 April; 4(4):357-8.
34. Shindo T, Kurihara Y, Nishimatsu H, Moriyama N, Kakoki M, Wang Y, Imai Y, Ebihara A, Kuwaki T, Ju K H, Minamino N, Kangawa K, Ishikawa T, Fukuda M, Akimoto Y, Kawakami H, Imai T, Morita H, Yazaki Y, Nagai R, Hirata Y, Kurihara H. Vascular abnormalities and elevated blood pressure in mice lacking adrenomedullin gene. 2001, *Circulation* 104:1964-1971.
35. Song J, Kim J. Degeneration of Dopaminergic Neurons Due to Metabolic Alterations and Parkinson's Disease. Front Aging Neurosci. 2016 Mar. 30; 8:65.
36. Tilakaratne N, Christopoulos G, Zumpe E T, Foord S M and Sexton P M. Amylin Receptor Phenotypes Derived from Human Calcitonin Receptor/RAMP Coexpression Exhibit Pharmacological Differences Dependent on Receptor Isoform and Host Cell Environment. J Pharmacol Exp Ther. 2000 July; 294(1):61-72.
37. Zhang L, Hoff A O, Wimalawansa S J, Cote G J, Gagel R F, Westlund K N. Arthritic calcitonin/alpha calcitonin gene-related peptide knockout mice have reduced nociceptive hypersensitivity. Pain. 2001 January; 89(2-3):265-73.
38. Zhang Z, Winborn C S, Marquez de Prado B, and Russo A F (2007). Sensitization of Calcitonin Gene-Related Peptide Receptors by Receptor Activity-Modifying Protein-1 in the Trigeminal Ganglion. The Journal of Neuroscience, 7 Mar. 2007, 27(10): 2693-2703; doi: 10.1523/JNEUROSCI.4542-06.2007

What is claimed is:

1. A method of reducing LDL in a patient in need thereof, the method comprising:
administering to the patient in need thereof an effective amount of a calcitonin gene-related peptide (CGRP) receptor antagonist or a pharmaceutically acceptable salt thereof;
wherein the CGRP receptor antagonist is a peptide or a pharmaceutically acceptable salt thereof comprising a structure of Formula I:

$$X^1-Y^1-Z^1 \qquad (I)$$

wherein:
$X^1$ is a modified N-terminal fragment of CGRP comprising from five to seven amino acid residues, wherein only two amino acid residues of the modified N-terminal fragment are cysteine (Cys), wherein the residue at the C-terminal end of the fragment is Cys, and wherein the residue immediately preceding the C-terminal Cys residue of the fragment is a non-threonine substitution of the threonine (Thr) residue of position 6 of human CGRP;
$Y^1$ is a central core region of CGRP wherein at least one amino acid of the central core is arginine (Arg) or lysine (Lys) and the central core region of CGRP comprises an α-helix; and
$Z^1$ is a modified C-terminal fragment of CGRP comprising from five to seven amino acid residues with a C-terminal amide, where at least one amino acid of the modified C-terminal fragment is phenylalanine (Phe), tyrosine (Tyr), proline (Pro) or hydroxyproline (Hyp).

2. The method of claim 1, wherein the CGRP receptor antagonist comprises a sequence selected from the group consisting of: SEQ ID NO: 1 (Ala-Cys-Asp-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$), SEQ ID NO: 2 (Ala-Cys-Asp-Thr-Ala-Ser-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$),
SEQ ID NO: 3 (Ala-Cys-Asp-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$), SEQ ID NO: 4 (Ala-Cys-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$), SEQ ID NO: 5 (Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$), SEQ ID NO: 6 (Ala-Cys-Arg-Phe-Gly-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$), SEQ ID NO: 7 (Ala-Cys-Asn-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$), SEQ ID NO: 8 (Cys-Ser-Asn-Thr-Ala-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$), SEQ ID NO: 9 (Ala-Cys-Asp-Thr-Ala-Leu-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$),
SEQ ID NO: 10 (Ala-Cys-Asp-Thr-Ala-Ile-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$), SEQ ID NO: 11 (Ala-Cys-Asn-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$), SEQ ID NO: 12 (Cys-Ser-Asn-Thr-Ala-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$), SEQ ID NO: 13 (Ala-Cys-Asn-Leu-Ser-Ala-Cys-Val-Leu-Gly-Arg-Leu-Ser-Gln-Glu- Leu-His-Arg-Leu-Gln-Thr-Tyr-Pro-Thr-Asn-Thr-Gly-Ser-Gly-Thr-Pro-NH$_2$), SEQ ID NO: 14 (Ala-Cys-Val-Leu-Gly-Ala-Cys-Val-Leu-Gly-Arg-Leu-Ser-Gln-Glu-Leu-His-Arg-Leu-Gln-Thr-Tyr-Pro-Val-Asp-Pro-Ser-Ser-Pro-His-Ser-Tyr-NH$_2$), SEQ ID NO: 15 (Ala-Cys-Asp-Thr-Ala-Ala-Cys-Val-Thr-His-Arg-Leu-Ala-Gly-Leu-Leu-Ser-Arg-Ser-Gly-Gly-Val-Val-Lys-Asn-Asn-Phe-Val-Pro-Thr-Asn-Val-Gly-Ser-Lys-Ala-Phe-NH$_2$), SEQ ID NO: 57 (Ala-Cys-Asp-Leu-Ser-Ala-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$) and SEQ ID NO: 58 (Ala-Cys-Asp-Leu-Ser-Val-Cys-Val-Leu-Gly-Arg-Leu-Ser-Gln-Glu-Leu-His-Arg-Leu-Gln-Thr-Tyr-Pro-Arg-Thr-Asn-Val-Gly-Ser-Lys-Ala-Phe-NH$_2$), or a pharmaceutically acceptable salt thereof.

3. The method of claim 1, wherein the CGRP receptor antagonist comprises a sequence selected from the group consisting of: SEQ ID NO: 1, 2, 3, 4, 5, 6, 7, 8, 9, 10, 11, 12 and 13.

4. The method of claim 1, wherein the patient in need thereof is suffering from a high LDL concentration in the blood.

5. The method of claim 1, further comprising monitoring or measuring the level or amount of LDL in the patient in need thereof before, during, or after administration of the effective amount of the CGRP receptor antagonist.

6. The method of claim 1, wherein the patient in need thereof is a male.

7. The method of claim 1, wherein the patient in need thereof has familial hypercholesterolemia.

8. The method of claim 1, wherein the CGRP receptor antagonist is administered dermally, intradermally, subcutaneously, via dermal infusion, via subcutaneous infusion, intravenously, buccally, intramuscularly, sublingually or orally.

9. The method of claim 1, wherein the effective amount comprises an amount between about 50 μg and 1000 mg.

10. The method of claim 1, wherein the administering is performed at least four times a day, three times a day, two times a day, or once a day.

* * * * *

UNITED STATES PATENT AND TRADEMARK OFFICE
CERTIFICATE OF CORRECTION

| | |
|---|---|
| PATENT NO. | : 12,103,951 B2 |
| APPLICATION NO. | : 17/806834 |
| DATED | : October 1, 2024 |
| INVENTOR(S) | : Christopher Joseph Soares |

It is certified that error appears in the above-identified patent and that said Letters Patent is hereby corrected as shown below:

On the Title Page

Item (56) Other Publications, Column 2, Line 10, delete "type 1 adrenomedulin receptor" and insert -- type 1 adrenomedullin receptor --.

Item (56) Other Publications, Column 2, Page 2, Line 72, delete "Dipeptide Isoteres, Tetrahedron" and insert -- Dipeptide Isosteres, Tetrahedron --.

In the Specification

Column 1, Line 17, delete "expressly Incorporated by" and insert -- expressly incorporated by --.

Column 3, Line 6-7, delete "by MDBiosciences, levels" and insert -- by MD Biosciences, levels --.

Column 3, Line 42, delete "sclerosis, Creutzfeld-Jakob disease," and insert -- sclerosis, Creutzfeldt-Jakob disease, --.

Column 5, Line 13, delete "Formula I." and insert -- Formula I: --.

Column 6, Line 42, delete "sclerosis, Creutzfeld-Jakob disease," and insert -- sclerosis, Creutzfeldt-Jakob disease, --.

Column 6, Line 53, delete "(i.e. chlorampheticol, Cipro)," and insert -- (i.e. chloramphenicol, Cipro), --.

Column 6, Line 54-55, delete "(i.e. Hydrazaline), anti-seizure" and insert -- (i.e. Hydralazine), anti-seizure --.

Column 8, Line 45, delete "sclerosis, Creutzfeld-Jakob disease," and insert -- sclerosis, Creutzfeldt-Jakob disease, --.

Signed and Sealed this
Thirty-first Day of December, 2024

Derrick Brent
*Acting Director of the United States Patent and Trademark Office*

Column 8, Line 60, delete "(i.e. chlorampheticol, Cipro)," and insert -- (i.e. chloramphenicol, Cipro), --.

Column 8, Line 61, delete "(i.e. Hydrazaline), anti-seizure" and insert -- (i.e. Hydralazine), anti-seizure --.

Column 9, Line 16, delete "Formula I." and insert -- Formula I: --.

Column 10, Line 58-59, delete "(i.e. chlorampheticol, Cipro)," and insert -- (i.e. chloramphenicol, Cipro), --.

Column 10, Line 60, delete "(i.e. Hydrazaline), anti-seizure" and insert -- (i.e. Hydralazine), anti-seizure --.

Column 11, Line 11, delete "Formula I." and insert -- Formula I: --.

Column 17, Line 43, delete "sclerosis, Creutzfeld-Jakob disease," and insert -- sclerosis, Creutzfeldt-Jakob disease, --.

Column 17, Line 55-56, delete "(i.e. chlorampheticol, Cipro)," and insert -- (i.e. chloramphenicol, Cipro), --.

Column 17, Line 57, delete "(i.e. Hydrazaline), anti-seizure" and insert -- (i.e. Hydralazine), anti-seizure --.

Column 20, Line 22, delete "sclerosis, Creutzfeld-Jakob disease," and insert -- sclerosis, Creutzfeldt-Jakob disease, --.

Column 20, Line 44, delete "(i.e. chlorampheticol, Cipro)," and insert -- (i.e. chloramphenicol, Cipro), --.

Column 20, Line 46, delete "(i.e. Hydrazaline), anti-seizure" and insert -- (i.e. Hydralazine), anti-seizure --.

Column 22, Line 65-66, delete "(i.e. chlorampheticol, Cipro)," and insert -- (i.e. chloramphenicol, Cipro), --.

Column 22, Line 67, delete "(i.e. Hydrazaline), anti-seizure" and insert -- (i.e. Hydralazine), anti-seizure --.

Column 29, Line 35, delete "RGCs (Retinol ganglion" and insert -- RGCs (Retinal ganglion --.

Column 29, Line 65, delete "of 20% or 10%, more" and insert -- of ±20% or ±10%, more --.

Column 30, Line 35, delete "acid, menthanesulfonic acid," and insert -- acid, methanesulfonic

CERTIFICATE OF CORRECTION (continued)
U.S. Pat. No. 12,103,951 B2 acid, --.

Column 32, Line 4, delete "meralgia parasthetic (injury" and insert -- meralgia paresthetic (injury --.

Column 32, Line 13, delete "Meralgia parasthetic (injury" and insert -- Meralgia paresthetic (injury --.

Column 32, Line 32, delete "interferon beta-la, interferon" and insert -- interferon beta-1a, interferon --.

Column 35, Line 34, delete "Less that 100" and insert -- Less than 100 --.

Column 38, Line 47, delete "(Ser), tryptophan (Typ) and" and insert -- (Ser), tryptophan (Trp) and --.

Column 38, Line 51, delete "(Ser), tryptophan (Typ) and" and insert -- (Ser), tryptophan (Trp) and --.

Column 39, Line 6, delete "Formula I, $X^{11}$ is" and insert -- Formula 1, $X^{15}$ is --.

Column 39, Line 9, delete "Formula I, $X^{11}$ is" and insert -- Formula I, $X^{15}$ is --.

Column 39, Line 35, delete "to $X^{11}$. In" and insert -- to $X^1$. In --.

Column 41, Line 8, delete "$Z^{13}$—$Z^4$-$Z^{15}$" and insert -- $Z^{13}$—$Z^{14}$—$Z^{15}$ --.

Column 41, Line 22, delete "embodiments, $Z^4$ is" and insert -- embodiments, $Z^{14}$ is --.

Column 41, Line 23, delete "embodiments, $Z^{11}$ is" and insert -- embodiments, $Z^{15}$ is --.

Column 46, Line 8, delete "delivery)" and insert -- delivery). --.

Column 47, Line 14, delete "rate" and insert -- rate. --.

Column 48, Line 1, delete "(i.e. chlorampheticol, Cipro)," and insert -- (i.e. chloramphenicol, Cipro), --.

Column 48, Line 3, delete "(i.e. Hydrazaline), anti-seizure" and insert -- (i.e. Hydralazine), anti-seizure --.

Column 60, Line 15 (approx.), delete "about +20% of" and insert -- about ± 20% of --.

Column 61, Line 41, (TABLE 4), delete "Trig—Tryglycerides, LDL" and insert -- Trig—Triglycerides, LDL --.

Column 61, Line 62 (approx.) (TABLE 5), delete "Trig—Tryglycerides, LDL" and insert -- Trig—Triglycerides, LDL --.

CERTIFICATE OF CORRECTION (continued)
U.S. Pat. No. 12,103,951 B2

Column 61, Line 63 (approx.) (TABLE 5), delete "lipoprotein," and insert -- lipoprotein. --.

Column 63, Line 54, delete "356-362" and insert -- 356-362. --.

Column 64, Line 2, delete "tonometers. Greafes Arch" and insert -- tonometers. Graefes Arch --.

Column 64, Line 50, delete "233-46" and insert -- 233-46. --.

Column 64, Line 58, delete "J, Ronkko S," and insert -- J, Rönkkö S, --.

Column 65, Line 11 (approx.), delete "124701" and insert -- 124701. --.

Column 66, Line 24 (approx.), delete "06.2007" and insert -- 06.2007. --.